United States Patent
Robichaud et al.

(10) Patent No.: US 10,426,837 B2
(45) Date of Patent: Oct. 1, 2019

(54) COMPOSITIONS AND METHODS FOR TREATING CNS DISORDERS

(71) Applicant: Sage Therapeutics, Inc., Cambridge, MA (US)

(72) Inventors: Albert J. Robichaud, Cambridge, MA (US); Gabriel Martinez Botella, Wayland, MA (US); Francesco G. Salituro, Marlborough, MA (US); Boyd L. Harrison, Princeton Junction, NJ (US)

(73) Assignee: Sage Therapeutics, Inc., Cambridge, MA (US)

( * ) Notice: Subject to any disclaimer, the term of this patent is extended or adjusted under 35 U.S.C. 154(b) by 0 days.

(21) Appl. No.: 15/660,114

(22) Filed: Jul. 26, 2017

(65) Prior Publication Data

US 2017/0319695 A1    Nov. 9, 2017

Related U.S. Application Data

(63) Continuation of application No. PCT/US2016/014835, filed on Jan. 26, 2016.

(60) Provisional application No. 62/144,789, filed on Apr. 8, 2015, provisional application No. 62/107,776, filed on Jan. 26, 2015.

(51) Int. Cl.
| | |
|---|---|
| A61K 45/06 | (2006.01) |
| C07J 43/00 | (2006.01) |
| A61K 31/00 | (2006.01) |
| C07J 3/00 | (2006.01) |
| C07J 7/00 | (2006.01) |
| C07J 13/00 | (2006.01) |
| C07J 41/00 | (2006.01) |
| C07J 51/00 | (2006.01) |
| C07J 9/00 | (2006.01) |
| A61K 45/00 | (2006.01) |

(52) U.S. Cl.
CPC .............. *A61K 45/06* (2013.01); *C07J 3/00* (2013.01); *C07J 3/005* (2013.01); *C07J 7/002* (2013.01); *C07J 7/007* (2013.01); *C07J 7/009* (2013.01); *C07J 7/0085* (2013.01); *C07J 13/007* (2013.01); *C07J 41/0044* (2013.01); *C07J 43/003* (2013.01); *C07J 51/00* (2013.01); *A61K 31/00* (2013.01); *A61K 45/00* (2013.01); *C07J 9/00* (2013.01)

(58) Field of Classification Search
CPC ........ A61K 31/00; A61K 31/56; A61K 31/58; A61K 45/00; C07J 3/00; C07J 3/005; C07J 7/002; C07J 7/007; C07J 7/0085; C07J 7/009; C07J 9/00; C07J 13/007; C07J 43/003; C07J 51/00
See application file for complete search history.

(56) References Cited

U.S. PATENT DOCUMENTS

| | | |
|---|---|---|
| 2,856,415 A | 10/1958 | Mihina |
| 3,169,134 A | 2/1965 | Klimstra et al. |
| 3,206,459 A | 9/1965 | Cross |
| 3,580,937 A | 5/1971 | Campbell et al. |
| 3,943,124 A | 3/1976 | Phillipps et al. |
| 3,983,111 A | 9/1976 | Phillipps et al. |
| 3,998,829 A | 12/1976 | Phillips et al. |
| 4,071,625 A | 1/1978 | Grunwell et al. |
| 4,179,336 A | 12/1979 | Weber et al. |
| 4,192,871 A | 3/1980 | Phillipps et al. |
| 4,389,345 A | 6/1983 | Lenz |
| 5,593,983 A | 1/1997 | Campbell |

(Continued)

FOREIGN PATENT DOCUMENTS

| | | |
|---|---|---|
| CN | 1190404 A | 8/1998 |
| CN | 101412742 A | 4/2009 |

(Continued)

OTHER PUBLICATIONS

Hogenkamp et al., Pharmacological profile of a 17beta-heteroaryl-substituted neuroactive steroid. Psychopharmacology, vol. 231, pp. 3517-3524 (Year: 2014).*
International Search Report and Written Opinion for Corresponding International Application No. PCT/US15/56054 dated Feb. 9, 2016.
International Search Report and Written Opinion for Corresponding International Application No. PCT/US2013/076214 dated Aug. 29, 2016.

(Continued)

*Primary Examiner* — Barbara P Badio
(74) *Attorney, Agent, or Firm* — Goodwin Procter LLP

(57) ABSTRACT

Described herein are neuroactive steroids of the Formula (I):

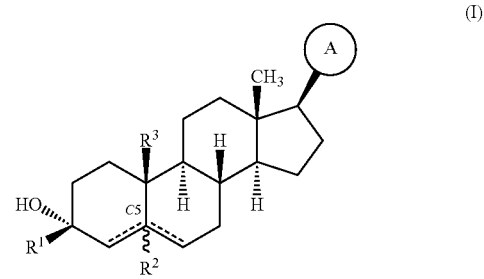

(I)

or a pharmaceutically acceptable salt thereof; wherein ═══, A, $R^1$, $R^2$, and $R^3$ are as defined herein. Such compounds are envisioned, in certain embodiments, to behave as GABA modulators. The present invention also provides pharmaceutical compositions comprising a compound of the present invention and methods of use, e.g., for treating a subject suffering from a disease or disorder described herein.

10 Claims, No Drawings

(56) References Cited

U.S. PATENT DOCUMENTS

| | | |
|---|---|---|
| 5,721,227 A | 2/1998 | Melloni et al. |
| 5,925,630 A | 7/1999 | Upasani et al. |
| 5,935,545 A | 8/1999 | Leary et al. |
| 5,939,545 A | 8/1999 | Upasani et al. |
| 6,133,280 A | 10/2000 | Brodie et al. |
| 6,143,736 A | 11/2000 | Upasani et al. |
| 6,277,838 B1 | 8/2001 | Upasani et al. |
| 6,717,002 B2 | 4/2004 | Yano et al. |
| 6,844,456 B2 | 1/2005 | Covey |
| 7,064,116 B2 | 6/2006 | Calogeropoulou et al. |
| 7,781,421 B2 | 8/2010 | Covey et al. |
| 8,759,330 B2 | 6/2014 | Covey et al. |
| 8,939,545 B2 | 1/2015 | Tunmore et al. |
| 9,156,876 B2 | 10/2015 | Covey |
| 9,365,611 B2 | 6/2016 | Martinez Botella et al. |
| 9,512,165 B2 | 12/2016 | Martinez Botella et al. |
| 9,630,986 B2 | 4/2017 | Covey et al. |
| 9,725,481 B2 | 8/2017 | Martinez Botella et al. |
| 9,765,110 B2 | 9/2017 | Covey |
| 10,246,482 B2 | 4/2019 | Harrison et al. |
| 2002/0091112 A1 | 7/2002 | Menzenbach et al. |
| 2005/0176976 A1 | 8/2005 | Calogeropoulou et al. |
| 2006/0094696 A1 | 5/2006 | Leese et al. |
| 2007/0014719 A1 | 1/2007 | Reading et al. |
| 2008/0269183 A1 | 10/2008 | Mellon et al. |
| 2009/0048218 A1 | 2/2009 | Kuhnke et al. |
| 2010/0152840 A1 | 6/2010 | Seguin et al. |
| 2010/0234335 A1 | 9/2010 | Gravanis et al. |
| 2010/0317638 A1 | 12/2010 | Covey et al. |
| 2011/0152840 A1 | 6/2011 | Lee et al. |
| 2011/0172242 A1 | 7/2011 | Helton et al. |
| 2014/0017675 A1 | 1/2014 | Ito |
| 2014/0050789 A1 | 2/2014 | Rogawski et al. |
| 2014/0094619 A1 | 4/2014 | Runyon et al. |
| 2014/0148412 A1 | 5/2014 | Hogenkamp |
| 2014/0235600 A1 | 8/2014 | Covey et al. |
| 2014/0275241 A1 | 9/2014 | Covey |
| 2015/0291654 A1 | 10/2015 | Upasani et al. |
| 2015/0315230 A1 | 11/2015 | Covey et al. |
| 2016/0068563 A1 | 3/2016 | Martinez Botella et al. |
| 2016/0083418 A1 | 3/2016 | Martinez Botella et al. |
| 2016/0108080 A1 | 4/2016 | Martinez Botella et al. |
| 2016/0229887 A1 | 8/2016 | Martinez Botella et al. |
| 2017/0233433 A1 | 8/2017 | Martinez Botella et al. |
| 2017/0246191 A1 | 8/2017 | Martinez Botella et al. |

FOREIGN PATENT DOCUMENTS

| | | |
|---|---|---|
| CN | 101624414 A | 1/2010 |
| CN | 104136452 A | 11/2014 |
| DE | 2330342 A1 | 1/1974 |
| DE | 2526373 A1 | 12/1976 |
| DE | 2700267 A1 | 7/1977 |
| DE | 2632677 A1 | 1/1978 |
| EP | 0104489 A1 | 4/1984 |
| EP | 0554436 A1 | 8/1993 |
| EP | 0656365 A1 | 6/1995 |
| EP | 0701444 A1 | 3/1996 |
| EP | 1038880 A2 | 9/2000 |
| FR | 1994 M | 9/1963 |
| GB | 1380246 A | 1/1975 |
| GB | 1430942 A | 4/1976 |
| GB | 1570394 A | 7/1980 |
| GB | 1581234 A | 12/1980 |
| RU | 2194712 C2 | 12/2002 |
| RU | 2243232 C2 | 12/2004 |
| RU | 2010100334 A | 7/2011 |
| RU | 2675855 C2 | 12/2018 |
| WO | 1991016897 A1 | 11/1991 |
| WO | 9303732 A1 | 3/1993 |
| WO | 9305786 A1 | 4/1993 |
| WO | 9318053 A1 | 9/1993 |
| WO | 9427608 A1 | 12/1994 |
| WO | 1995021617 A1 | 8/1995 |
| WO | 1996003421 A1 | 2/1996 |
| WO | 1996016076 A1 | 5/1996 |
| WO | 9640043 A2 | 12/1996 |
| WO | 9805337 A1 | 2/1998 |
| WO | 0066614 A1 | 11/2000 |
| WO | 2005051972 A1 | 6/2005 |
| WO | 2005105822 A2 | 11/2005 |
| WO | 2006037016 A2 | 4/2006 |
| WO | 2006131392 A1 | 12/2006 |
| WO | 2008151745 A1 | 12/2008 |
| WO | 2008157460 A1 | 12/2008 |
| WO | 2010003391 A2 | 1/2010 |
| WO | 2010107815 A1 | 9/2010 |
| WO | 2012013816 A1 | 2/2012 |
| WO | 2012083090 A2 | 6/2012 |
| WO | 2012109752 A1 | 8/2012 |
| WO | 2012110010 A1 | 8/2012 |
| WO | 2012116290 A2 | 8/2012 |
| WO | WO2013019711 * | 2/2013 |
| WO | 2013036835 A1 | 3/2013 |
| WO | 2013056181 A1 | 4/2013 |
| WO | 2013188792 A2 | 12/2013 |
| WO | 2014058736 A1 | 4/2014 |
| WO | 2014071449 A1 | 5/2014 |
| WO | 2014100228 A1 | 6/2014 |
| WO | 2014169831 A1 | 10/2014 |
| WO | 2014169832 A1 | 10/2014 |
| WO | 2014169833 A1 | 10/2014 |
| WO | 2014169836 A1 | 10/2014 |
| WO | 2015010054 A2 | 1/2015 |
| WO | 2015027227 A1 | 2/2015 |
| WO | 2015180679 A1 | 12/2015 |
| WO | 2015195962 A1 | 12/2015 |
| WO | 2016061527 A1 | 4/2016 |
| WO | 2016061537 A1 | 4/2016 |
| WO | 2016082789 A1 | 6/2016 |
| WO | 2016123056 A1 | 8/2016 |
| WO | 2016134301 A2 | 8/2016 |
| WO | 2016209847 A1 | 12/2016 |
| WO | 2017044659 A1 | 3/2017 |
| WO | 2017066626 A1 | 4/2017 |
| WO | 2017087864 A1 | 5/2017 |
| WO | 2017156103 A1 | 9/2017 |
| WO | 2017156418 A1 | 9/2017 |
| WO | 2018013613 A1 | 1/2018 |
| WO | 2018013615 A1 | 1/2018 |
| WO | 2018039378 A1 | 3/2018 |
| WO | 2019045121 A1 | 3/2019 |

OTHER PUBLICATIONS

International Search Report and Written Opinion for Corresponding International Application No. PCT/US2014/052417 dated Nov. 19, 2014.

International Search Report and Written Opinion for Corresponding International Application No. PCT/US2014/092369 dated Aug. 25, 2015

International Search Report and Written Opinion for Corresponding International Application No. PCT/US2015/056066 dated Feb. 8, 2016.

International Search Report and Written Opinion for Corresponding International Application No. PCT/US2016/014835 dated Jun. 9, 2016.

International Search Report and Written Opinion for Corresponding International Application No. PCT/US2016/018748 dated Aug. 29, 2016.

International Search Report and Written Opinion for Corresponding International Application No. PCT/US2016/062874 dated Jan. 30, 2017.

International Search Report and Written Opinion for Corresponding International Application No. PCT/US2017/041600 dated Dec. 1, 2017.

International Search Report and Written Opinion for Corresponding International Application No. PCT/US2017/041605 dated Dec. 12, 2017.

International Search Report and Written Opinion for Corresponding International Application No. PCT/US2017/048267 dated Aug. 29, 2016.

(56) References Cited

OTHER PUBLICATIONS

International Search Report and Written Opinion for International Application No. PCT/CN2013/074312 dated Jan. 23, 2014.
International Search Report and Written Opinion for International Application No. PCT/CN2013/074319 dated Jan. 23, 2014.
International Search Report and Written Opinion for International Application No. PCT/CN2013/074323 dated Jan. 30, 2014.
International Search Report and Written Opinion for International Application No. PCT/CN2013/074325 dated Jan. 23, 2014.
International Search Report and Written Opinion for International Application No. PCT/CN2014/075585 dated Aug. 4, 2014.
International Search Report and Written Opinion for International Application No. PCT/CN2014/075593 dated Jul. 22, 2014.
International Search Report and Written Opinion for International Application No. PCT/CN2014/075594 dated Jul. 16, 2014.
International Search Report and Written Opinion for International Application No. PCT/CN2014/075600 dated Jul. 29, 2014.
International Search Report and Written Opinion for International Application No. PCT/US14/47246, dated Jan. 22, 2015.
International Search Report for International Application No. PCT/US2012/060136 dated Mar. 27, 2013.
Jiang et al., "Neurosteroid analogues. 9. Conformationally constrained pregnanes: structure-activity studies of 13,24-cyclo-18, 21-dinorcholane analogues of the GABA modulatory and anesthetic steroids (3a,5a)- and (3a,5a)-3-hydroxypregnan-20-one", Journal of Medicinal Chemistry, 2003, vol. 46, pp. 5334-5348.
Kaji et al., "Synthesis of 3-epi-6, 7-dideoxyxestobergsterol A", Chem. & Pharm. Bulletin, 2000, vol. 48, No. 10, pp. 1480-1483.
Katona et al., "Neurosteroid analogues. 12. Potent enhancement of GABA-mediated chloride currents at GABAA receptors by ent-androgens", European Journal of Medicinal Chemistry, 2008, vol. 43, pp. 107-113.
Knox et al., "Steroids. CCLXXVIII. Reductions of 19-substituted androst-4-en-3-ones and related compounds", Journal of Organic Chemistry, 1965, vol. 30, No. 7, pp. 2198-2205.
Krafft et al., "Synthesis of the C/D/E and A/B Rings of Xestobergsterol—(A)", Journal of Organic Chemistry, American Chemical Society, vol. 64, No. 7, (1999), pp. 2475-2485.
Krishnan et al., "Neurosteroid Analogues. Chapter 17. Inverted Binding Orientations of Androsterone Enantiomers at the Steroid Potentiation Site on y-Aminobutyric Acid Type A Receptors", Journal of Medicinal Chemistry, 2012, vol. 55, No. 3, pp. 1334-1345.
Lan et al., "Neurosteroid Analogues. 4. The Effect of Methyl Substitution at the C-5 and C-10 Positions of Neurosteroids on Electrophysiological Activity at GABAA Receptors", Journal of Medicinal Chemistry, (1996), vol. 39, pp. 4218-4232.
Lewbart et al., "Oxidation of Steroidal a-Ketols to Glyoxals with Cupric Acetate", Journal of Organic Chemistry, (1963), vol. 28, No. 8, pp. 2001-2006.
Li et al., "Neuroactive Steroids and Human Recombinant p1 GABAc Receptors", Journal of Pharmacology and Experimental Therapeutics, (2007), vol. 323, pp. 236-247.
Mangialasche et al., "Alzheimer's disease: clinical trials and drug development", Lance Neurology, vol. 9 (2010), pp. 702-716.
Matsui et al., "Comparative fate of testosterone and testosterone sulfate in female rats: $C19O2$ and $C19O3$ steroid metabolites in the bile", Journal of Steroid Biochemistry, 1977, 8(4), pp. 323-328.
Mok et al., "Evidence that 5a-pregnan-3a-ol-20-one is the metabolite responsible for progesterone anesthesia", Brain Research (1990), 533(1), pp. 42-45.
Morrow et al., "Characterization of Steroid Interactions with gamma-Aminobutyric Acid Receptor-Gated Chloride Ion Channels: Evidence for Multiple Steroid Recognition Sites", 1989, Molecular Pharmacology, 37, pp. 263-270.
Nilsson et al., "Neurosteroid analogues. 6. The synthesis and GABAA receptor pharmacology of enantiomers of dehydroepiandrosterone sulfate, pregnenolone sulfate, and (3a,5b)-3-hydroxypregnan-20-one sulfate", Journal of Medicinal Chemistry, 1998, vol. 41, pp. 2604-2613.

Notification of Transmittal of the International Search Report and the Written Opinion of the International Searching authority, or the Declaration, International Application No. PCT/US13/45933, dated Dec. 3, 2013, 5 Pages.
Paradiso et al., "Steroid Inhibition of Rat Neuronal Nicotinic a4B2 Receptors Expressed in HEK 293 Cells", Journal of Molecular Pharmacology, (2000), vol. 58, pp. 341-351.
Paul et al., "Neuroactive Steroids", The Journal of the Federation of American Societies for Experimental Biology, (1992), pp. 2311-2322.
Peart et al., "Hydroxylation of steroids by Fusarium oxysporum, Exophiala jeanselmei and Ceratocystis paradoxa", Steroids, vol. 76, No. 12, (2011), pp. 1317-1330.
Pechet et al., "Metabolism of 19-hydroxycorticosterone. Isolation and characterization of three metabolites", Journal of Biological Chemistry, Jan. 1, 1961, vol. 236, No. 10, pp. PC68-PC69.
Phillipps et al., "A New Series of Steroidal Antidysrhythmic Agents," J. Steroid Biochem. 19(1):759-765 (1983).
Phillipps et al., "Water-soluble Steroidal Anaesthetics", Journal of Steroid Biochemistry 11:79-86 (1979).
Phillipps, "Structure-Activity Relationships in Steroidal Anaesthetics", Journal of Steroid Biochemistry, (1975), vol. 6, pp. 607-613.
Phillipps, "Structure-Activity Relationships in Steroidal Anaesthetics", Nol. Mech. Gen. Anaesth. Glaxo Symposium, (1974), pp. 32-47.
PubChem-70249446 (2012), entire document.
Purdy et al., "Synthesis, Metabolism, and Pharmacological Activity of 3a-Hydroxy Steroids Which Potentiate GABA-Receptor-Mediated Chloride Ion Uptake in Rat Cerebral Cortical Synaptoneurosomes", Journal of Medicinal Chemistry, (1990), vol. 33, pp. 1572-1581.
Qian et al., "Neurosteroid Analogues, 18. Structure-Activity Studies of ent-Steroid Potentiators of y-Aminobutyric Acid Type A Receptors and Comparison of Their Activities with Those of Alphaxalone and Allopregnanolone", Journal of Medicinal Chemistry, 2014, vol. 57, No. 1, pp. 171-190.
Qian et al., "The efficient and enantiospecific total synthesis of cyclopenta[b]phenanthrenes structurally related to neurosteroids", Adv. Syn. & Cata., 2010, vol. 352, Nos. 11-12, pp. 2057-2061.
Rogawski et al., "Neuroactive steroids for the treatment of status epilepticus", Epilepsia, 54:(2013), pp. 93-98.
Runyon et al., "17b-Nitro-5a-androstan-3a-ol and its 3b-methyl derivative: Neurosteroid analogs with potent anticonvulsant and anxiolytic activities", European Journal of Pharmacology 617, (2009), pp. 68-73.
Ruzicka et al., "Steroids and sex hormones. CXXXIX. The relation between constitution and odor of steroids. Methylandrostane and allopregnane derivatives", Helvetica Chimica Acta, 1947, vol. 30, pp. 867-878.
Rychnovsky et al., "Synthesis of ent-cholesterol, the unnatural enantiomer", Journal of Organic Chemistry, 1992, vol. 57, No. 9, pp. 2732-2736.
Santaniello & Caspi, "Reduction of certain steroidal 19-sulfonic esters with metal hydrides", J. of Ster. Biochem, 1976, vol. 7, No. 3, pp. 223-227.
Sarett., "A new method for the preparation of 17(alpha)-hydroxy-20-ketopregnanes", J. Am. Chem. Soc., 1948, vol. 70, pp. 1454-1458.
Scaglione et al., "Neurosteroid Analogues. 14. Alternative Ring System Scaffolds: GABA Modulatory and Anesthetic Actions of Cyclopenta[b]phenanthrenes and Cyclopenta[b]anthracenes", 2008, Journal of Medicinal Chemistry, vol. 51, pp. 1309-1318.
Shen et al., "Microbial aromatization of 19-hydroxymethylepidehydroandrosterone acetate by Corynebacterium simplex", Huaxue Xuebao, 1983, vol. 41, No. 5, pp. 473-474.
Shu et al., "Characteristics of concatemeric GABM receptors containing alpha4/d subunits expressed in Xenopus oocytes" British Journal of Pharmacology (2012) 165, 2228-2243.
Slavíková et al., "Allopregnanolone (3a-Hydroxy-5a-pregnan-20-one) Derivatives with a Polar Chain in Position 16a: Synthesis and Activity", Journal of Medicinal Chemistry, vol. 52, No. 7, (2009), 2119-2125.

(56) References Cited

OTHER PUBLICATIONS

Spiegel et al., "Use of Nonaqueous Solvents in Parenteral Products", Journal of Pharmaceutical Sciences, 1963, vol. 52, No. 10, pp. 917-927.
Starnes et al., "Thin-Layer Chromatography of 17-Kelosteroid 2,4-Dinitrophenylhydrazones", Journal of Clinical Endocrinology and Metabolism, 1966, vol. 26, No. 11, pp. 1245-1250.
Stastna et al., "Neurosteroid Analogues. 16. A New Explanation for the Lack of Anesthetic Effects in D16—Alphaxalone and Identification of a D17(20) Analogue with Potent Anesthetic Activity", Journal of Medicinal Chemistry, 2011, vol. 54, No. 11, pp. 3926-3934.
Stastna et al., "Stereoselectivity of sodium borohydride reduction of saturated steroidal ketones utilizing conditions of Luche reduction", Steroids, 2010, vol. 75, No. 10, pp. 721-725.
Stastna et al., "Synthesis of C3, C5, and C7 pregnane derivatives and their effect on NMDA receptor responses in cultured rat hippocampal neurons", Steroids, Elsevier Science Publishers, vol. 74, No. 2, (2008), pp. 256-263.
Stastna et al., "The use of symmetry in enantioselective synthesis: Four pairs of chrysene enantiomers prepared from 19-nortestosterone", Org. Biomol. Chem., 2011, vol. 9, pp. 4685-4694.
Supplemental European Search Report, European Patent Application No. 14826212.4, dated Feb. 16, 2017.
Tsai et al., "Synthesis and antiproliferative activity of 3a-hydroxyl-3b-methoxymethyl-5a-pregnan-20-one with a C-21 hydrophilic substituent", Heteroatom Chemistry, (2017), pp. 1-9.
Upasani et al., "3a-Hydroxy-3β-(phenylethynyl)-5β-pregnan-20-ones: Synthesis and Pharmacological Activity of Neuroactive Steroids with High Affinity for GABAA Receptors", J. Med. Chem. (1997) vol. 40, No. 1, pp. 73-84.
Vanover et al., "Behavioral characterization of Co 134444 (3a-hydroxy-21-(1'-imidazolyl)-3b-methoxymethyl-5a-pregnan-20-one), a novel sedative-hypnotic neuroactive steroid", Psychopharmacology (2001), vol. 155, pp. 285-291.
Vanover et al., "Characterization of the Anxiolytic Properties of a Novel Neuroactive Steroid, Co 2-6749 (GMA-839; WAY-141839; 3a, 21-Dihydroxy-3b-trifluoromethyl-19-nor-5b-pregnan-20-one), a Selective Modulator of y-Aminobutyric AcidA Receptors", The Journal of Pharmacology and Experimental Therapeutics, (2000), vol. 295, No. 1, pp. 337-345.
Vanover et al., "Response-Rate Suppression in Operant Paradigm as Predictor of Soporific Potency in Rats and Identification of Three Novel Sedative-Hypnotic Neuroactive Steroids", The Journal of Pharmacology and Experimental Therapeutics, (1999), vol. 291, No. 3, pp. 1317-1323.
Wicha et al., "Transformations of steroidal neopentyl systems. II. Migration of acetate from the 3beta-to the 19- hydroxyl in delta 5 and A/B-trans steroids", Canadian Journal of Chemistry, 1967, vol. 45, No. 7, pp. 707-711.
Wicha et al., "Transformations of steroidal neopentyl systems. IV. Stereochemistry of Products of Reaction of Methyllithium with Steroidal A5-19-aldehydes", Journal of the Chemical Society (Section) C: Organic, 1968, vol. 14, 1740-1746.
Wicha et al., "Transformations of steroidal neopentyl systems. V. Synthesis and proof of the configuration of 19amethyl-19S-alcohols", Journal of the Chemical Society [Section] C: Organic, 1969, vol. 6, pp. 947-951.
Wicha et al., "Transformations of steroidal neopentyl systems. VI. Intramolecular Claisen condensation of 19R-acetoxy-19A-methyl-3-ones of the 5alpha series", Tetrahedron, 1969, vol. 25, No. 17, pp. 3961-3968.
Wicha et al., "Transformations of steroidal neopentyl systems. VII. Mechanism of the transformation of (19R)-(19)-hydroxy-19-methyl-3-oxo-5alpha-to 3alpha-hydroxy-19-methyl-19—oxo-5alpha-analogs", Journal of Organic Chemistry, 1973, vol. 38 No. 7, pp. 1280-1283.
Wu, "A New Classification of Prodrugs: Regulatory Perspectives", Pharmaceuticals, 2009, vol. 2, pp. 77-81.
Zeng et al., "Neurosteroid Analogues. 10. The Effect of Methyl Group Substitution at the C-6 and C-7 Positions on the GABA Modulatory and Anesthetic Actions of (3a,5a) -and (3a, 5b)-3-Hydroxypregnan-20-one", Journal of Medicinal Chemistry, (2005). vol. 48, pp. 3051-3059.
Zonana et al., "The Neurobiology of Postpartum Depression", CNS Spectrums, (2005), pp. 792-799, 805.
Zorumski et al., "Enantioselective Modulation of GABAergic Synaptic Transmission by Steroids and Benz[dindenes in Hippocampal Microcultures", Synapse, (1998), vol. 29, pp. 162-171.
Anderson et al., "Anesthetic Activity of Novel Water-Soluble 2b-Morpholinyl Steroids and Their Modulatory Effects at GABA-A Receptors", Journal of Medicinal Chemistry., 1997, vol. 40, pp. 1668-1681.
Anderson et al., "Conformationally Constrained Anesthetic Steroids That Modulate GABAA Receptors," Journal of Medicinal Chemistry, 2000, vol. 43, No. 22, pp. 4118-4125.
Atack, "Development of Subtype-Selective GABAA Receptor Compounds for the Treatment of Anxiety, Sleep Disorders and Epilepsy", GABA and Sleep. Molecular, Functional and Clinical Aspects. 2010, pp. 25-72.
Banday et al., "D-ring substituted 1,2,3-triazolyl 20-keto pregnenanes as potential anticancer agents: Synthesis and biological evaluation", Steroids, (2010), vol. 75, No. 12, pp. 801-804, Abstract.
Bandyopadhyaya et al., "Neurosteroid Analogs. 15. A Comparative Study of the Anesthetic and GABAergic Actions of Alphaxalone, D16-Alphaxalone and Their Corresponding 17-Carbonitrile Analogs," Bioorganic & Medicinal Chemistry Letters 20:6680-6684 (2010).
Berge et al., J. Pharmaceutical Sciences, 1977, vol. 66, pp. 1-19.
Bernstein, "Rett Syndrome Medication", Medscape, (2017).
Bjorkhem et al., "Steroid hormone metabolism in developing rates", Eur. J.Biochem., 1972, vol. 27, No. 2, pp. 318-326.
Botella et al., "Neuroactive Steroids. 1. Positive Allosteric Modulators of the (g-Aminobutyric Acid)A Receptor: Structure-Activity Relationships of Heterocyclic Substitution at C-21", Journal of Medical Chemistry, 2015, pp. 3500-3511.
Botella et al., "Neuroactive Steroids. 2. 3a-Hydroxy-3b-methyl-21-(4-cyano-1H-pyrazol-1-yl)-19-nor-5b-pregnan-20-one (SAGE-217): A Clinical Next Generation Neuroactive Steroid Positive Allosteric Modulator of the (g-Aminobutyric Acid) A Receptor" Journal of Medical Chemistry, 2017, 10 pp. A-J.
CAS registry No. 1040410-23-8.
CAs registry No. 162882-77-1.
CAS registry No. 162883-68-3.
Caspi et al., "Stereochemistry of 19-hydroxy-19alpha-methyl steroids," Chemical Communications, 1966, vol. 7, pp. 209-210.
Cerny et al., "Syntheses of 19-[O-(carboxymethyl)oxime] haptens of epipregnanolone and pregnanolone", Steroids, 2006, vol. 71(2), pp. 120-128.
Cerny et al., "Synthetic approach to 5alpha-pregnanolone 19-[0-(carboxymethyl) oxime] derivatives", Collection of Czechoslovak Chemical Communications, 2004, vol. 69, No. 9, pp. 1805-1817.
Chodounska et al., "Epalons: Synthesis of 3a, 7a-Dihydroxy-5a-Pregnan-20-One", Collection Symposium Series, vol. 63, No. 10, (1998), pp. 1543-1548.
Database CAPLUS in STN, Acc. No. 1995:986323, Upasani et al., WO 9521617 A1 (Aug. 17, 1995) (abstract). [Upasani, Ravindra B. "Androstanes and pregnanes for allosteric modulation of GABA receptor, and preparation and therapeutic uses of compounds".].
Database CAPLUS in STN, Acc. No. 1998:112239, Lan, WO 9805337 A1 (Feb. 12, 1998) (abstract). [Lan, Nancy C., "Use of GABA agonists and NMDA receptor antagonists for the treatment of migraine headache".].
Deluca et al., "Synthesis of 3b-Hydroxy[21-14C]-5b-pregn-8(14)-en-20-one from Chenodeoxycholic Acid", Helvetica Chemica Acta, vol. 69, (1986), pp. 1844-1850.
Deniau et al., "Synthesis of fluorinated analogues of the neurosteroid GABA receptor antagonist, 17-PA", Journal of Fluorine Chemistry, (2008), vol. 129, No. 9, pp. 881-887.
Dorwald, "Side Reactions in Organic Synthesis", 2005, Wiley-VCH, Preface, p. IX.

(56) References Cited

OTHER PUBLICATIONS

Edgar et al., "CCD-3693: An Orally Bioavailable Analog of the Endogenous Neuroactive Steroid, Pregnanolone, Demonstrates Potent Sedative Hypnotic Actions in the Rat" The Journal of Pharmacology and Experimental Therapeutics (1997) vol. 282, No. 1, pp. 420-429.
Evers et al., "A Synthetic 18-Norsleroid Distinguishes Between Two Neuroactive Steroid Binding Sites on GABAA Receptors", Journal of Pharmacology and Experimental Therapeutics, 2010, vol. 333, No. 2, pp. 404-413.
Extended European Search Report for application PCT/CN2014075593 dated Aug. 26, 2016.
Extended European Search Report for application PCT/CN2014075594 dated Aug. 26, 2016.
Fesik et al., "Geometric Requirements for Membrance Perturbation and Anesthetic Activity", Molecular Pharmacology, 1985, vol. 27, pp. 624-629.
Gasior et al., "Neuroactive steroids: potential therapeutic use in neurological and psychiatric disorders", Trends in Pharmacological Science, (1999), vol. 20, No. 3, pp. 107-112.
Green et al., "The nonfeminizing enantiomer of 17b-estradiol exerts protective effects in neuronal cultures and a rat model of cerebral ischemia", Endocrinology, 2001, vol. 142, pp. 400-406.
Gustafsson et al., "Steroid excretion patterns in urine from ovariectomized and adrenalectomized rats", Biochmica ET Biophysica ACTA—Lipids and Lipid Metabolism, Elsevier Science BV, 1972, vol. 280, No. 1, pp. 182-186.
Gustafsson et al., "Steroids in Germfree and Conventional Rats. 7. Identification of C19 and C21 Steroids in faeces from Conventional Rats", European Journal of Biochemistry, 1968, vol. 6, No. 2, pp. 248-255.
Gyermek et al., "Steroids, CCCX. 1 Structure-Activity Relationship of Some Steroidal Hypnotic Agents", Journal of Medicinal Chemistry, 1968, vol. 11, No. 1, pp. 117-125.
Han et al., "Neurosteroid Analogs. 3. The Synthesis and Electrophysiological Evaluation of Benz[e]indene Congeners of Neuroactive Steroids Having the 5b-Configuration", Journal of of Medicinal Chemistry, 1995, vol. 38, No. 22, pp. 4548-4556.
Harrison et al., "Structure-Activity Relationships for Steroid Interaction with the y-Aminobutyric AcidA Receptor Complex" The Journal of Pharmacology and Experimental Therapeutics (1987) vol. 241, No. 1, pp. 346-353.
Hauser et al., "Steroids. CCV. Fragmentations and intramolecular abstractions of tertiary hydrogen atoms by primary oxy radicals with fixed reaction centers", Helv. Chim. Acta, 1964, vol. 47, pp. 1961-1979.
Hawkinson et al., "3a-Hydroxy-3b-trifluoromethyl-5a-pregnan-20-one (Co Feb. 1970): A Partial Agonist at the Neuroactive Steroid Site of the y-Aminobutyric acidA Receptor" Molecular Pharmacology (1996) vol. 49, pp. 897-906.
Hawkinson et al., "Correlation of Neuroactive Steroid Modulation of [35S]t-Butylbicyclophosphorothionate and [3H] Flunitrazepam Binding and y-Aminobutyric AcidA Receptor Function", Molecular Pharmacology (1994) vol. 46, pp. 977-985.
Hawkinson et al., "Substituted 3b-Phenylethynyl Derivatives of 3a-Hydroxy-5a-pregnan-20-one: Remarkably Potent Neuroactive Steroid Modulators of y-Aminobutyric AcidA Receptors", The Journal of Pharmacology and Experimental Therapeutics(1998), vol. 287, No. 1, pp. 198-207.
Heard et al., "Steroids VII. Preparation of of androstan-3(b)-ol-7-one from from dehydroisoandrosterone", Journal of Biological Chemistry, 1946, vol. 165, pp. 677-685.
Hewett et al., "Amino steroids. Part III. 2- and 3-Amino-5a-androstanes", Journal of the Chemical Society, 1968, vol. 9, pp. 1134-1140.
Hill et al., "Pholochemische Reaktionen. 32 Milleilung. UV-Bestrahlung von gesattigten und bela,gamma-ngesalligten, homoallylisch konjugierten steroidaldehyden", Helvetica Chimica Acta, 1946, vol. 49, No. 1, pp. 292-311.

Hogenkamp et al., "Synthesis and in Vitro Activity of 3b-Substituted-3a-hydroxypregnan-20-ones: Allosteric Modulators of the GABAA Receptor", Journal of Medicinal Chemistry, (1997), vol. 40, pp. 61-72.
Hu et al., "Neurosteroid analogues. Part 5. Enantiomers of neuroactive steroids and benz[e]indenes: total synthesis,18 electrophysiological effects on GABAA receptor function and anesthetic actions in tadpoles", J. Chem. Soc. Perkin Trans 1, 1997, pp. 3665-3671.
Hu et al., "Neurosteroid Analogues: Structure-Activity Studies of Benz(e] indene Modulators of GABAA Receptor Function. 1. The Effect of 6-Melhyl Substitution on the Electrophysiological Activity of 7-Substituted Benz[e]indene-3-carbonitriles", Journal of Medicinal Chemistry, (1993), pp. 3956-3967.
Im et al., "Studies on the Mechanism of Interactions between Anesthetic Steroids and y-Aminobutyric AcidA Receptors", Molecular Pharmacology (1990), 37(3), pp. 429-434.
International Search Report and Written Opinion for Corresponding International Application No. PCT/CN2014/078820 dated Feb. 27, 2015.
International Search Report and Written Opinion for Corresponding International Application No. PCT/CN2015/080216 dated Aug. 3, 2015.
International Search Report and Written Opinion for Corresponding International Application No. PCT/CN2015/095765 dated Mar. 4, 2016.
International Search Report and Written Opinion for Corresponding International Application No. PCT/US15/36500 dated Sep. 11, 2015.
Anonymous: "Archive History for NCT03000530", Aug. 4, 2017, Retrieved from the Internet: <URL:https://www.clinicaltrials.gov/ct2/his> tory/NCT03000530?V-_6=View#StudyPageTop; [retrieved on Nov. 20, 2018].
Chen et al., "The mechanism investigation in substitution of 21-bromo-3a-hydroxy-3b-methoxymethyl-5a-pregnan-20-one with nucleophiles", Steroids, vol. 71, (2006), pp. 942-948.
Database Medline, US National Library of Medicine, Bethesda, MD, 1984, Welling: "Intentions affecting drug absorption", Database accession No. NLM6388952, abstract.
Eimon et al., "Brain activity patterns in high-throughput electrophysiology screen predict both drug efficacies and side effects", Nature Communications, (2018) 9:219, pp. 1-14.
Gottesmann, "GABA Mechanisms and Sleep", Neuroscience, (2002), vol. 111, No. 2, pp. 231-239.
Gunduz-Bruce et al.,"Sage-217 in Subjects with Major Depressive Disorder: Efficacy and Safety Results from Open-Label Part A of a Phase 2a Study", Poster, (Presented on Sep. 2-5, 2017 at the 30th ECNP Congress, Paris, France.
Hawkins et al., "The synthetic neuroactive steroid SGE-516 reduces seizure burden and improves survival in a Dravet syndrome mouse model", Science Reports, (2017), pp. 1-8.
International Search Report and Written Opinion for Corresponding International Application No. PCT/US2018/050012 dated Dec. 7, 2018.
International Search Report and Written Opinion for Corresponding International Application No. PCT/US2018/051048 dated Jan. 11, 2019.
Kanes et al., "A multiple-ascending dose study of the neuroactive steroid Sage-217", Biological Psychiatry, vol. 81, No. 10, 2017, pp. S347.
Kanes et al., "A single-ascending dose study of the neuroactive steroid Sage-217", Biological Psychiatry, vol. 81, No. 10, 2017, pp. S31.
Möhler, "The GABA system in anxiety and depression and its therapeutic potential", Neuropharmacology, (2012) 62; pp. 42-53.
Sage Therapeutics: "Sage Therapeutics Advances SAGE-217 into Placebo-Controlled Phase 2 Clinical Trial in Major Depressive Disorder", Feb. 13, 2017, Retrieved from the Internet: <URL:https://investor.sagerx.com/static-fil>es/80fflf35-fc4c-4eb2-9456-3228ec891a59; [retrieved on Dec. 21, 2018].
Welling, "Interactions affecting drug absorption", Clinical Pharmacokinetics, vol. 9, No. 5, Sep. 1984 (Sep. 1984), pp. 404-434.

* cited by examiner

COMPOSITIONS AND METHODS FOR TREATING CNS DISORDERS

RELATED APPLICATIONS

This application is a continuation of Application PCT/US2016/014835 filed on Jan. 26, 2016, which claims priority under 35 U.S.C. § 119(e) to U.S. Provisional Applications No. 62/107,776 filed Jan. 26, 2015 and 62/144,789 filed Apr. 8, 2015, the entire contents of which are incorporated herein by reference.

BACKGROUND OF THE INVENTION

Brain excitability is defined as the level of arousal of an animal, a continuum that ranges from coma to convulsions, and is regulated by various neurotransmitters. In general, neurotransmitters are responsible for regulating the conductance of ions across neuronal membranes. At rest, the neuronal membrane possesses a potential (or membrane voltage) of approximately −70 mV, the cell interior being negative with respect to the cell exterior. The potential (voltage) is the result of ion ($K^+$, $Na^+$, $Cl^-$, organic anions) balance across the neuronal semipermeable membrane. Neurotransmitters are stored in presynaptic vesicles and are released under the influence of neuronal action potentials. When released into the synaptic cleft, an excitatory chemical transmitter such as acetylcholine will cause membrane depolarization, e.g., a change of potential from −70 mV to −50 mV. This effect is mediated by postsynaptic nicotinic receptors which are stimulated by acetylcholine to increase membrane permeability to $Na^+$ ions. The reduced membrane potential stimulates neuronal excitability in the form of a postsynaptic action potential.

In the case of the GABA receptor complex (GRC), the effect on brain excitability is mediated by GABA, a neurotransmitter. GABA has a profound influence on overall brain excitability because up to 40% of the neurons in the brain utilize GABA as a neurotransmitter. GABA regulates the excitability of individual neurons by regulating the conductance of chloride ions across the neuronal membrane. GABA interacts with its recognition site on the GRC to facilitate the flow of chloride ions down an electrochemical gradient of the GRC into the cell. An intracellular increase in the levels of this anion causes hyperpolarization of the transmembrane potential, rendering the neuron less susceptible to excitatory inputs, i.e., reduced neuron excitability. In other words, the higher the chloride ion concentration in the neuron, the lower the brain excitability and level of arousal.

It is well-documented that the GRC is responsible for the mediation of anxiety, seizure activity, and sedation. Thus, GABA and drugs that act like GABA or facilitate the effects of GABA (e.g., the therapeutically useful barbiturates and benzodiazepines (BZs), such as VALIUM®) produce their therapeutically useful effects by interacting with specific regulatory sites on the GRC. Accumulated evidence has now indicated that in addition to the benzodiazepine and barbiturate binding site, the GRC contains a distinct site for neuroactive steroids. See, e.g., Lan, N. C. et al, Neurochem. Res. (1991) 16:347-356.

Neuroactive steroids can occur endogenously. The most potent endogenous neuroactive steroids are 3α-hydroxy-5-reduced pregnan-20-one and 3α-21-dihydroxy-5-reduced pregnan-20-one, metabolites of hormonal steroids progesterone and deoxycorticosterone, respectively. The ability of these steroid metabolites to alter brain excitability was recognized in 1986 (Majewska, M. D. et al., Science 232: 1004-1007 (1986); Harrison, N. L. et al., J Pharmacol. Exp. Ther. 241:346-353 (1987)).

The ovarian hormone progesterone and its metabolites have been demonstrated to have profound effects on brain excitability (Backstrom, T. et al., Acta Obstet. Gynecol. Scand. Suppl. 130:19-24 (1985); Pfaff, D. W and McEwen, B. S., Science 219:808-814 (1983); Gyermek et al., J Med Chem. 11: 117 (1968); Lambert, J. et al., Trends Pharmacol. Sci. 8:224-227 (1987)). The levels of progesterone and its metabolites vary with the phases of the menstrual cycle. It has been well documented that the levels of progesterone and its metabolites decrease prior to the onset of menses. The monthly recurrence of certain physical symptoms prior to the onset of menses has also been well documented. These symptoms, which have become associated with premenstrual syndrome (PMS), include stress, anxiety, and migraine headaches (Dalton, K., Premenstrual Syndrome and Progesterone Therapy, 2nd edition, Chicago Yearbook, Chicago (1984)). Subjects with PMS have a monthly recurrence of symptoms that are present in premenses and absent in postmenses.

In a similar fashion, a reduction in progesterone has also been temporally correlated with an increase in seizure frequency in female epileptics, i.e., catamenial epilepsy (Laidlaw, J., Lancet, 1235-1237 (1956)). A more direct correlation has been observed with a reduction in progesterone metabolites (Rosciszewska et al., J. Neurol. Neurosurg. Psych. 49:47-51 (1986)). In addition, for subjects with primary generalized petit mal epilepsy, the temporal incidence of seizures has been correlated with the incidence of the symptoms of premenstrual syndrome (Backstrom, T. et al., J. Psychosom. Obstet. Gynaecol. 2:8-20 (1983)). The steroid deoxycorticosterone has been found to be effective in treating subjects with epileptic spells correlated with their menstrual cycles (Aird, R. B. and Gordan, G., J. Amer. Med. Soc. 145:715-719 (1951)).

A syndrome also related to low progesterone levels is postnatal depression (PND). Immediately after birth, progesterone levels decrease dramatically leading to the onset of PND. The symptoms of PND range from mild depression to psychosis requiring hospitalization. PND is also associated with severe anxiety and irritability. PND-associated depression is not amenable to treatment by classic antidepressants, and women experiencing PND show an increased incidence of PMS (Dalton, K., Premenstrual Syndrome and Progesterone Therapy, 2nd edition, Chicago Yearbook, Chicago (1984)).

Collectively, these observations imply a crucial role for progesterone and deoxycorticosterone and more specifically their metabolites in the homeostatic regulation of brain excitability, which is manifested as an increase in seizure activity or symptoms associated with catamenial epilepsy, PMS, and PND. The correlation between reduced levels of progesterone and the symptoms associated with PMS, PND, and catamenial epilepsy (Backstrom, T. et al., *J Psychosom. Obstet. Gynaecol.* 2:8-20 (1983)); Dalton, K., Premenstrual Syndrome and Progesterone Therapy, 2nd edition, Chicago Yearbook, Chicago (1984)) has prompted the use of progesterone in their treatment (Mattson et al., "Medroxyprogesterone therapy of catamenial epilepsy," in *Advances in Epileptology: XVth Epilepsy International Symposium*, Raven Press, New York (1984), pp. 279-282, and Dalton, K., *Premenstrual Syndrome and Progesterone Therapy*, 2nd edition, Chicago Yearbook, Chicago (1984)). However, progesterone is not consistently effective in the treatment of the aforementioned syndromes. For example, no dose-response relationship exists for progesterone in the treatment of PMS (Maddocks et al., *Obstet. Gynecol.* 154:573-581 (1986); Dennerstein et al., *Brit. Med J* 290:16-17 (1986)).

New and improved neuroactive steroids are needed that act as modulating agents for brain excitability, as well as agents for the prevention and treatment of CNS-related diseases. The compounds, compositions, and methods described herein are directed toward this end.

SUMMARY OF THE INVENTION

Provided herein are C17-substituted neuroactive steroids designed, for example, to act as GABA modulators. In certain embodiments, such compounds are envisioned to be useful as therapeutic agents for the inducement of anesthesia and/or sedation in a subject. In some embodiments, such compounds are envisioned to be useful as therapeutic agents for treating a CNS-related disorder (e.g., sleep disorder, a mood disorder, a schizophrenia spectrum disorder, a convulsive disorder, a disorder of memory and/or cognition, a movement disorder (e.g., tremor, for example essential tremor), a personality disorder, autism spectrum disorder, pain, traumatic brain injury, a vascular disease, a substance abuse disorder and/or withdrawal syndrome, or tinnitus) in a subject in need (e.g., a subject with Rett syndrome, Fragile X syndrome, or Angelman syndrome).

In one aspect, provided is a compound of the Formula (I):

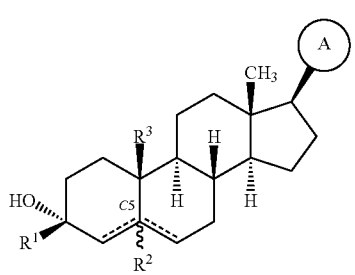

or a pharmaceutically acceptable salt thereof; wherein: Ring A is aryl or heteroaryl; $R^1$ is hydrogen, $C_{1-3}$ alkyl (e.g., unsubstituted $C_{1-3}$ alkyl (e.g., —$CH_3$, —$CH_2CH_3$) or substituted $C_{1-3}$ alkyl (e.g., $C_{1-3}$ haloalkyl (e.g., —$CHF_2$, —$CH_2F$, —$CF_3$), —$CH_2OCH_3$)), $C_{2-6}$ alkenyl, or $C_{3-6}$ carbocylyl; $R^2$ is absent or hydrogen; $R^3$ is hydrogen, alkyl, or —$CH_2OR^{3A}$, wherein $R^{3A}$ is hydrogen, $C_{1-6}$ alkyl, $C_{2-6}$ alkenyl, $C_{2-6}$ alkynyl, aryl, heteroaryl, or $C_{3-6}$ carbocyclyl; ===== represents a single or double bond, wherein when one ===== is a double bond, the other ===== is a single bond; wherein when $R^1$ is —$CH_3$, $R^2$ is hydrogen in the alpha configuration, and $R^3$ is —$CH_3$, then A is aryl.

In some embodiments, when $R^3$ is —$CH_3$, $R^2$ is hydrogen in the beta configuration.

In some embodiments, the compound of Formula (I) is a compound of Formula (I-a):

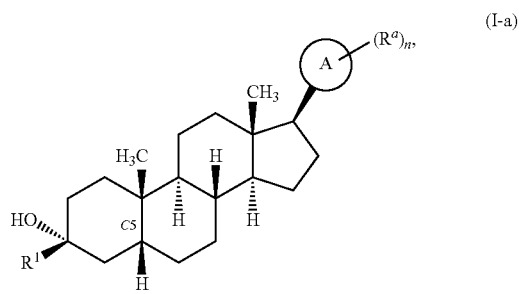

wherein: n is 0, 1, 2, 3, 4, or 5; $R^a$ is halogen, $C_1$-$C_6$ alkyl, $C_2$-$C_6$ alkenyl, $C_2$-$C_6$ alkynyl, carbocyclyl, heterocyclyl, aryl, heteroaryl, —$C(O)R^A$, —$C(O)OR^A$, —$C(O)NR^BR^C$, —$S(O)_2R^D$, or —$OR^Y$, wherein $R^Y$ is hydrogen, $C_1$-$C_6$ alkyl, $C_2$-$C_6$ alkenyl, $C_2$-$C_6$ alkynyl, carbocyclyl, heterocyclyl, aryl, heteroaryl, —$C(O)R^A$, —$C(O)OR^A$, —$C(O)NR^BR^C$, or —$S(O)_2R^D$; $R^A$ is hydrogen, $C_1$-$C_6$ alkyl, carbocyclyl, heterocyclyl, aryl, or heteroaryl; each of $R^B$ and $R^C$ is independently hydrogen, $C_1$-$C_6$ alkyl, carbocyclyl, heterocyclyl, aryl, heteroaryl, or taken together with the atom to which they are attached form a ring (e.g., a 3-7-membered ring, e.g., a 5-7-membered ring; a ring containing at least one heteroatom, e.g., a nitrogen, oxygen, or sulfur atom); and $R^D$ is hydrogen, $C_1$-$C_6$ alkyl, carbocyclyl, heterocyclyl, aryl, or heteroaryl.

In some embodiments, A is a 5-7-membered ring. In some embodiments, A is monocyclic or bicyclic. In some embodiments, A is monocyclic. In some embodiments, A is bicyclic. In some embodiments, A contains at least one nitrogen atom. In some embodiments, A contains two nitrogen atoms. In some embodiments, A is a 5-membered ring. In some embodiments, A is oxazole, pyrazole, or thiazole. In some embodiments, A is a 6-membered ring. In some embodiments, A is an aryl ring. In some embodiments, A is phenyl. In some embodiments, A is a heteroaryl ring. In some embodiments, A is pyridine or pyrimidine.

In some embodiments, n is 0 or 1. In some embodiments, n is 0. In some embodiments, n is 1, and $R^a$ is alkyl (e.g., —$CH_2OH$).

In some embodiments, $R^1$ is unsubstituted $C_{1-3}$ alkyl. In some embodiments, $R^1$ is —$CH_3$.

In some embodiments, the compound of Formula (I-a) is selected from:

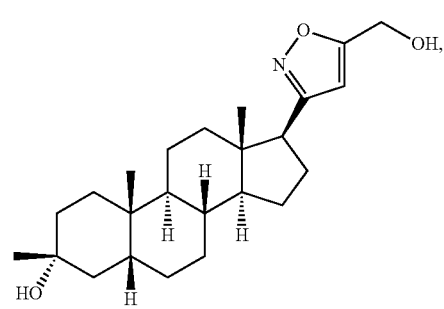

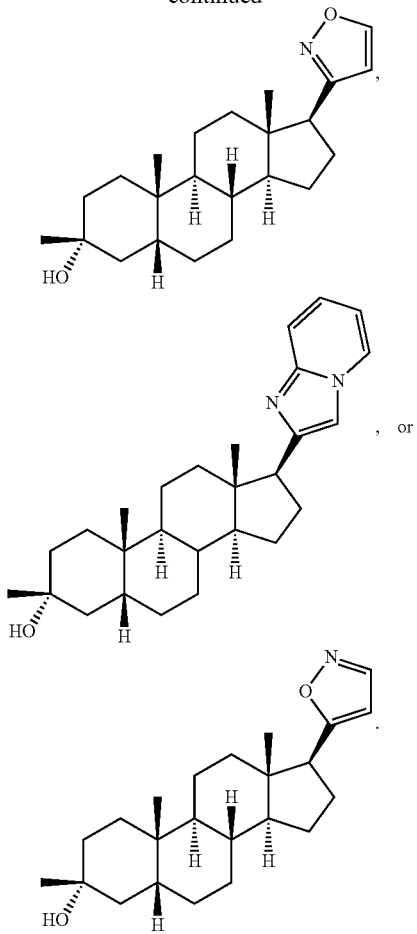

In some embodiments, the compound of Formula (I) is a compound of Formula (I-b):

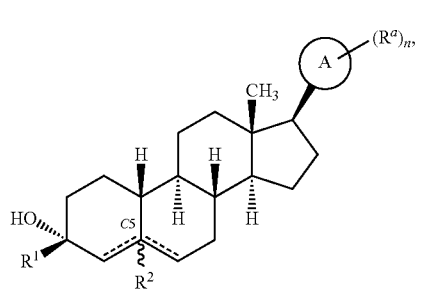

(I-b)

wherein: n is 0, 1, 2, 3, 4, or 5; $R^a$ is halogen, $C_1$-$C_6$ alkyl, $C_2$-$C_6$ alkenyl, $C_2$-$C_6$ alkynyl, carbocyclyl, heterocyclyl, aryl, heteroaryl, —C(O)$R^A$, —C(O)O$R^A$, —C(O)N$R^B R^C$, —S(O)$_2 R^D$, or —O$R^Y$, wherein $R^Y$ is hydrogen, $C_1$-$C_6$ alkyl, $C_2$-$C_6$ alkenyl, $C_2$-$C_6$ alkynyl, carbocyclyl, heterocyclyl, aryl, heteroaryl, —C(O)$R^A$, —C(O)O$R^A$, —C(O)N$R^B R^C$, or —S(O)$_2 R^D$; $R^A$ is hydrogen, $C_1$-$C_6$ alkyl, carbocyclyl, heterocyclyl, aryl, or heteroaryl; each of $R^B$ and $R^C$ is independently hydrogen, $C_1$-$C_6$ alkyl, carbocyclyl, heterocyclyl, aryl, heteroaryl, or taken together with the atom to which they are attached form a ring (e.g., a 3-7-membered ring, e.g., a 5-7-membered ring; a ring containing at least one heteroatom, e.g., a nitrogen, oxygen, or sulfur atom); and $R^D$ is hydrogen, $C_1$-$C_6$ alkyl, carbocyclyl, heterocyclyl, aryl, or heteroaryl.

In some embodiments, the compound of Formula (I-b) is a compound of Formula (I-b-i), (I-b-ii), (I-b-iii), or (I-b-iv):

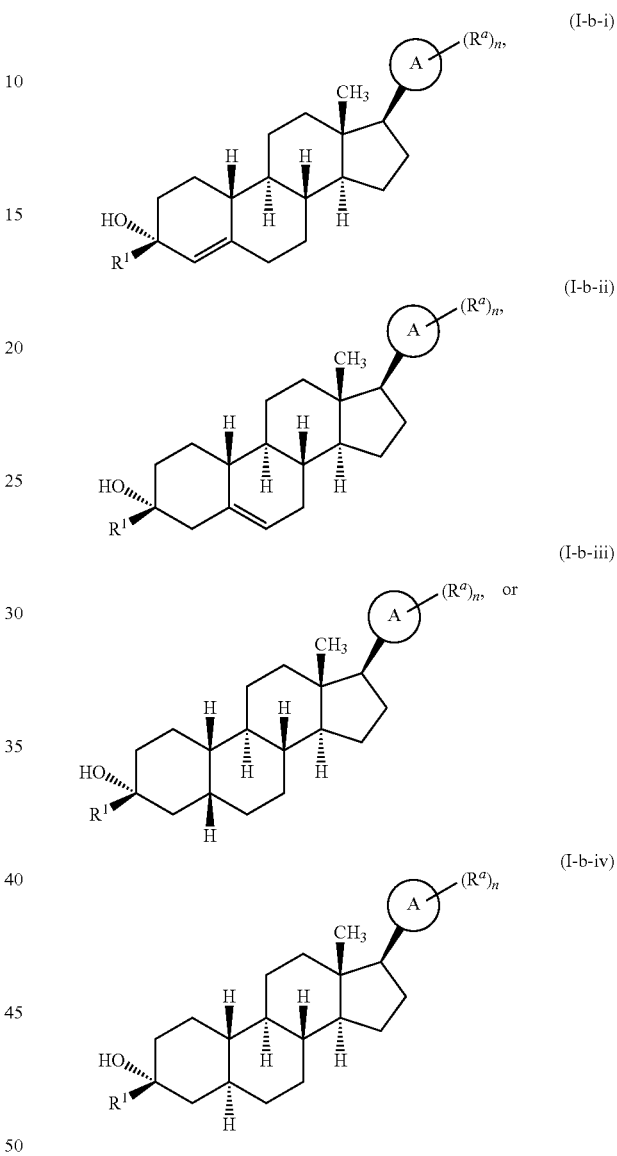

In some embodiments, A is a 5-7-membered ring.

In some embodiments, A is monocyclic or bicyclic. In some embodiments, A is monocyclic. In some embodiments, A is bicyclic. In some embodiments, A contains at least one nitrogen atom. In some embodiments, A contains two nitrogen atoms. In some embodiments, A is a 5-membered ring. In some embodiments, A is oxazole, pyrazole, or thiazole. In some embodiments, A is a 6-membered ring. In some embodiments, A is an aryl ring. In some embodiments, A is phenyl. In some embodiments, A is a heteroaryl ring. In some embodiments, A is pyridine or pyrimidine.

In some embodiments, n is 0 or 1. In some embodiments, n is 0.

In some embodiments, n is 1, and $R^a$ is alkyl (e.g., —CH$_2$OH).

In some embodiments, $R^1$ is unsubstituted $C_{1-3}$ alkyl. In some embodiments, $R^1$ is —CH$_3$. In some embodiments, $R^1$ is —CH$_2$CH$_3$. In some embodiments, R$^1$ is substituted C$_{1-3}$ alkyl. In some embodiments, R$^1$ is C$_{1-3}$ haloalkyl. In some embodiments, R$^1$ is —CHF$_2$, —CH$_2$F, or —CF$_3$. In some embodiments, R$^1$ is —CH$_2$OCH$_3$.

In some embodiments, the compound of Formula (I-b) is selected from:

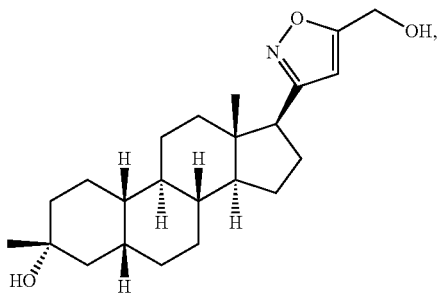

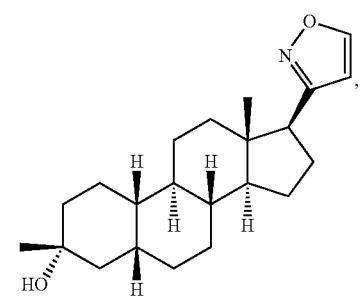

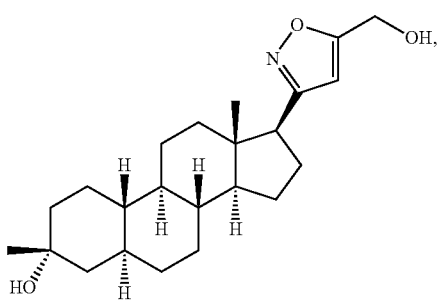

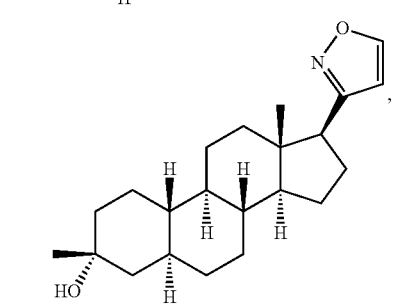

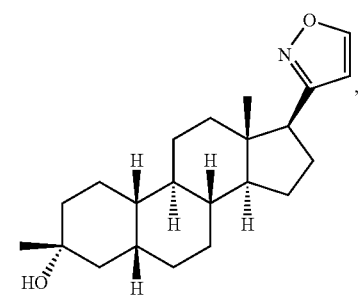

-continued

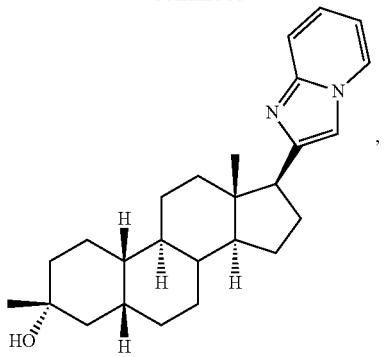

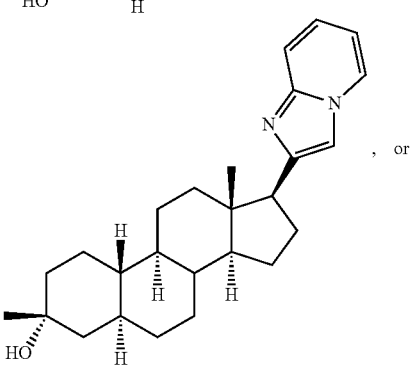

, or

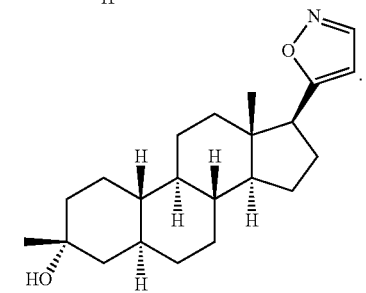

.

In some embodiments, the compound of Formula (I) is a compound of Formula (I-c):

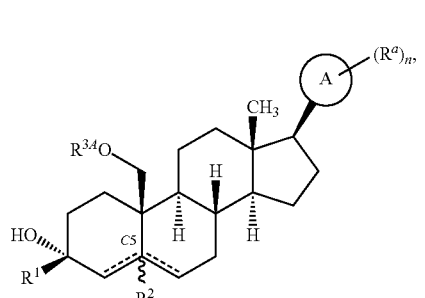

(I-c)

wherein: n is 0, 1, 2, 3, 4, or 5; R$^a$ is halogen, C$_1$-C$_6$ alkyl, C$_2$-C$_6$ alkenyl, C$_2$-C$_6$ alkynyl, carbocyclyl, heterocyclyl, aryl, heteroaryl, —C(O)R$^A$, —C(O)OR$^A$, —C(O)NR$^B$R$^C$, —S(O)$_2$R$^D$, or —OR$^Y$, wherein R$^Y$ is hydrogen, C$_1$-C$_6$ alkyl, C$_2$-C$_6$ alkenyl, C$_2$-C$_6$ alkynyl, carbocyclyl, heterocyclyl, aryl, heteroaryl, —C(O)R$^A$, —C(O)OR$^A$, —C(O)NR$^B$R$^C$, or —S(O)$_2$R$^D$; R$^A$ is hydrogen, C$_1$-C$_6$ alkyl, carbocyclyl, heterocyclyl, aryl, or heteroaryl; each of R$^B$ and R$^C$ is independently hydrogen, C$_1$-C$_6$ alkyl, carbocyclyl, heterocyclyl, aryl, heteroaryl, or taken together with the atom to which they are attached form a ring (e.g., a 3-7-membered ring, e.g., a 5-7-membered ring; a ring containing at least one heteroatom, e.g., a nitrogen, oxygen, or sulfur atom); and $R^D$ is hydrogen, $C_1$-$C_6$ alkyl, carbocyclyl, heterocyclyl, aryl, or heteroaryl.

In some embodiments, the compound of Formula (I-c) is a compound of Formula (I-c-i), (I-c-ii), (I-c-iii), or (I-c-iv):

In some embodiments, A is a 5-7-membered ring. In some embodiments, A is monocyclic or bicyclic. In some embodiments, A is monocyclic. In some embodiments, A is bicyclic. In some embodiments, A contains at least one nitrogen atom. In some embodiments, A contains two nitrogen atoms. In some embodiments, A is a 5-membered ring. In some embodiments, A is oxazole, pyrazole, or thiazole. In some embodiments, A is a 6-membered ring. In some embodiments, A is an aryl ring. In some embodiments, A is phenyl. In some embodiments, A is a heteroaryl ring. In some embodiments, A is pyridine or pyrimidine.

In some embodiments, n is 0 or 1. In some embodiments, n is 0. In some embodiments, n is 1, and $R^a$ is alkyl (e.g., —$CH_2OH$).

In some embodiments, $R^1$ is unsubstituted $C_{1-3}$ alkyl. In some embodiments, $R^1$ is —$CH_3$. In some embodiments, $R^1$ is —$CH_2CH_3$. In some embodiments, $R^1$ is substituted $C_{1-3}$ alkyl. In some embodiments, $R^1$ is $C_{1-3}$ haloalkyl. In some embodiments, $R^1$ is —$CHF_2$, —$CH_2F$, or —$CF_3$. In some embodiments, $R^1$ is —$CH_2OCH_3$.

In some embodiments, the compound of Formula (I-c) is selected from:

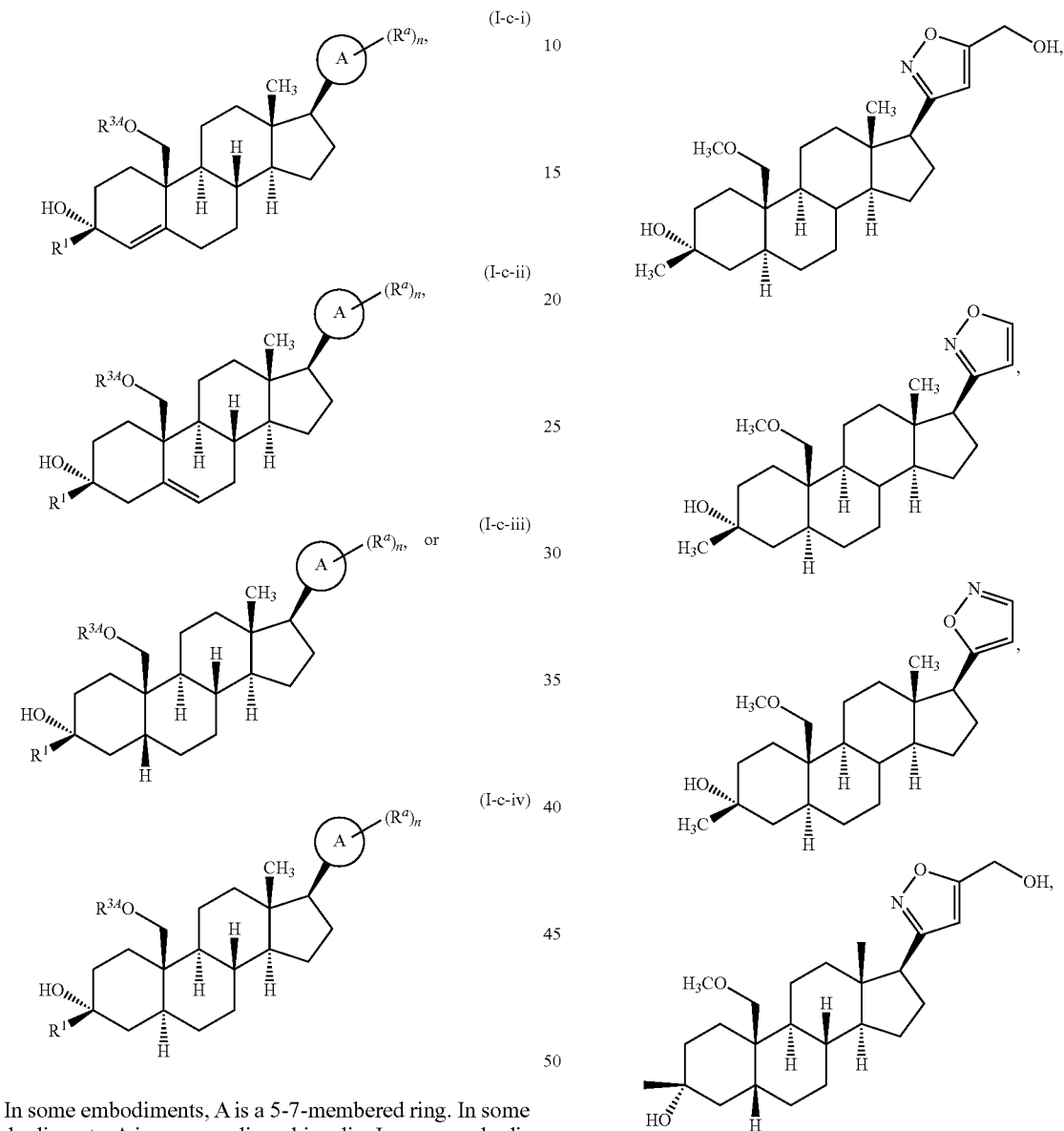

-continued

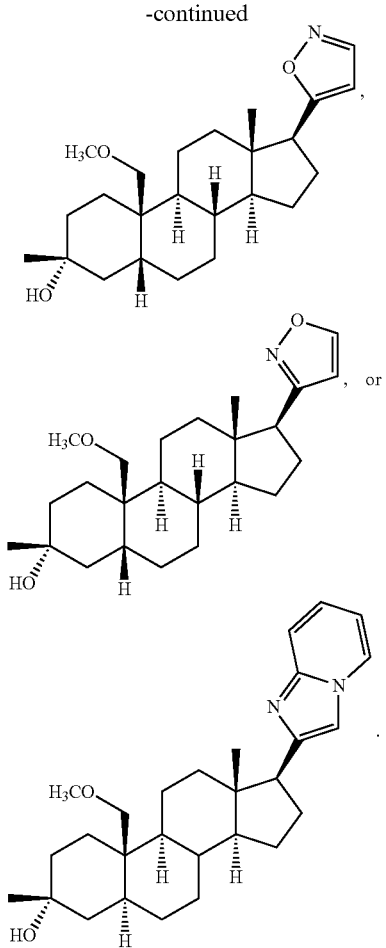

In one aspect, provided is a pharmaceutical composition comprising a compound of any one of the preceding claims and a pharmaceutically acceptable excipient.

In one aspect, provided is a method of inducing sedation and/or anesthesia in a subject, comprising administering to the subject an effective amount of a compound of the Formula (I):

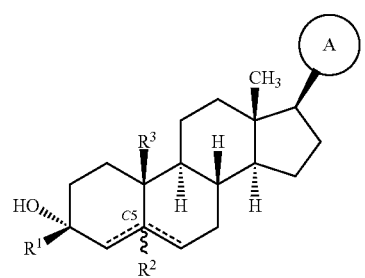

or a pharmaceutically acceptable salt thereof; wherein: Ring A is aryl or heteroaryl; $R^1$ is hydrogen, $C_{1-3}$ alkyl (e.g., unsubstituted $C_{1-3}$ alkyl (e.g., —$CH_3$, —$CH_2CH_3$) or substituted $C_{1-3}$ alkyl (e.g., $C_{1-3}$ haloalkyl (e.g., —$CHF_2$, —$CH_2F$, —$CF_3$), —$CH_2OCH_3$)), $C_{2-6}$ alkenyl, or $C_{3-6}$ carbocylyl; $R^2$ is absent or hydrogen; $R^3$ is hydrogen, alkyl, or —$CH_2OR^{3A}$, wherein $R^{3A}$ is hydrogen, $C_{1-6}$ alkyl, $C_{2-6}$ alkenyl, $C_{2-6}$ alkynyl, aryl, heteroaryl, or $C_{3-6}$ carbocyclyl; ═══ represents a single or double bond, wherein when one ═══ is a double bond, the other ═══ is a single bond; wherein when $R^1$ is —$CH_3$, $R^2$ is hydrogen in the alpha configuration, and $R^3$ is —$CH_3$, then A is aryl.

In some embodiments, when $R^3$ is —$CH_3$, $R^2$ is hydrogen in the beta configuration.

In one aspect, provided is a method of administering an effective amount of a compound, a pharmaceutically acceptable salt thereof, or pharmaceutical composition of a compound described herein (e.g., a compound of Formula (I)), to a subject in need thereof, wherein the subject experiences sedation and/or anesthesia within two hours of administration.

In some embodiments, the subject experiences sedation and/or anesthesia within one hour of administration. In some embodiments, the subject experiences sedation and/or anesthesia instantaneously.

In some embodiments, the compound is administered by intravenous administration.

In some embodiments, the compound is administered chronically.

In some embodiments, the subject is a mammal. In some embodiments, the subject is a human.

In some embodiments, the compound is administered in combination with another therapeutic agent.

In one aspect, provided is a method for treating seizure in a subject, comprising administering to the subject an effective amount of a compound of the Formula (I):

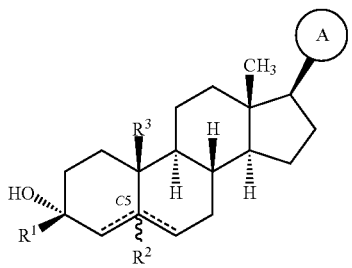

or a pharmaceutically acceptable salt thereof; wherein: Ring A is aryl or heteroaryl; $R^1$ is hydrogen, $C_{1-3}$ alkyl (e.g., unsubstituted $C_{1-3}$ alkyl (e.g., —$CH_3$, —$CH_2CH_3$) or substituted $C_{1-3}$ alkyl (e.g., $C_{1-3}$ haloalkyl (e.g., —$CHF_2$, —$CH_2F$, —$CF_3$), —$CH_2OCH_3$)), $C_{2-6}$ alkenyl, or $C_{3-6}$ carbocylyl; $R^2$ is absent or hydrogen; $R^3$ is hydrogen, alkyl, or —$CH_2OR^{3A}$, wherein $R^{3A}$ is hydrogen, $C_{1-6}$ alkyl, $C_{2-6}$ alkenyl, $C_{2-6}$ alkynyl, aryl, heteroaryl, or $C_{3-6}$ carbocyclyl; ═══ represents a single or double bond, wherein when one ═══ is a double bond, the other ═══ is a single bond; wherein when $R^1$ is —$CH_3$, $R^2$ is hydrogen in the alpha configuration, and $R^3$ is —$CH_3$, then A is aryl.

In some embodiments, when $R^3$ is —$CH_3$, $R^2$ is hydrogen in the beta configuration.

In one aspect, provided is a method for treating epilepsy or status or status epilepticus in a subject, the method comprising administering to the subject an effective amount of a compound of the Formula (I):

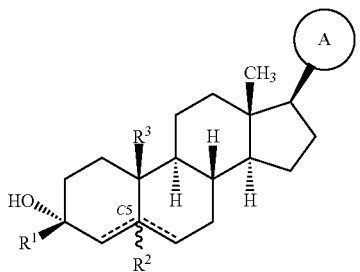

(I)

or a pharmaceutically acceptable salt thereof; wherein: Ring A is aryl or heteroaryl; $R^1$ is hydrogen, $C_{1-3}$ alkyl (e.g., unsubstituted $C_{1-3}$ alkyl (e.g., —$CH_3$, —$CH_2CH_3$) or substituted $C_{1-3}$ alkyl (e.g., $C_{1-3}$ haloalkyl (e.g., —$CHF_2$, —$CH_2F$, —$CF_3$), —$CH_2OCH_3$)), $C_{2-6}$ alkenyl, or $C_{3-6}$ carbocylyl; $R^2$ is absent or hydrogen; $R^3$ is hydrogen, alkyl, or —$CH_2OR^{3A}$, wherein $R^{3A}$ is hydrogen, $C_{1-6}$ alkyl, $C_{2-6}$ alkenyl, $C_{2-6}$ alkynyl, aryl, heteroaryl, or $C_{3-6}$ carbocyclyl; ===== represents a single or double bond, wherein when one ===== is a double bond, the other ===== is a single bond; wherein when $R^1$ is —$CH_3$, $R^2$ is hydrogen in the alpha configuration, and $R^3$ is —$CH_3$, then A is aryl.

In some embodiments, when $R^3$ is —$CH_3$, $R^2$ is hydrogen in the beta configuration.

In one aspect, provided is a method for treating disorders related to GABA function in a subject in need thereof, the method comprising administering to the subject a therapeutically effective amount of a compound, a pharmaceutically acceptable salt thereof, or pharmaceutical composition of one of a compound of Formula (I):

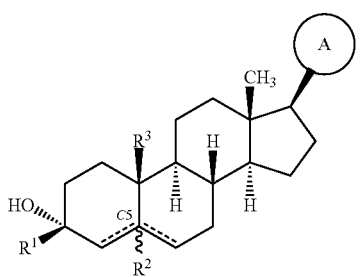

(I)

or a pharmaceutically acceptable salt thereof; wherein: Ring A is aryl or heteroaryl; $R^1$ is hydrogen, $C_{1-3}$ alkyl (e.g., unsubstituted $C_{1-3}$ alkyl (e.g., —$CH_3$, —$CH_2CH_3$) or substituted $C_{1-3}$ alkyl (e.g., $C_{1-3}$ haloalkyl (e.g., —$CHF_2$, —$CH_2F$, —$CF_3$), —$CH_2OCH_3$)), $C_{2-6}$ alkenyl, or $C_{3-6}$ carbocylyl; $R^2$ is absent or hydrogen; $R^3$ is hydrogen, alkyl, or —$CH_2OR^{3A}$, wherein $R^{3A}$ is hydrogen, $C_{1-6}$ alkyl, $C_{2-6}$ alkenyl, $C_{2-6}$ alkynyl, aryl, heteroaryl, or $C_{3-6}$ carbocyclyl; ===== represents a single or double bond, wherein when one ===== is a double bond, the other ===== is a single bond; wherein when $R^1$ is —$CH_3$, $R^2$ is hydrogen in the alpha configuration, and $R^3$ is —$CH_3$, then A is aryl.

In some embodiments, when $R^3$ is —$CH_3$, $R^2$ is hydrogen in the beta configuration.

In one aspect, provided is a method for treating a CNS-related disorder in a subject in need thereof, comprising administering to the subject an effective amount of a compound described herein (e.g., a compound of Formula (I)), or a pharmaceutically acceptable salt thereof.

In some embodiments, the CNS-related disorder is a sleep disorder, a mood disorder, a schizophrenia spectrum disorder, a convulsive disorder, a disorder of memory and/or cognition, a movement disorder (e.g., tremor, for example essential tremor), a personality disorder, autism spectrum disorder, pain, traumatic brain injury, a vascular disease, a substance abuse disorder and/or withdrawal syndrome, or tinnitus.

In some embodiments, the compound is administered orally.

In some embodiments, the compound is administered intramuscularly.

In some embodiments, the subject is a subject with Rett syndrome, Fragile X syndrome, or Angelman syndrome.

In one aspect, provided is a method for treating a human subject suffering from postpartum depression, the method comprising intravenously administering to the subject a therapeutically effective amount of compound of Formula (I):

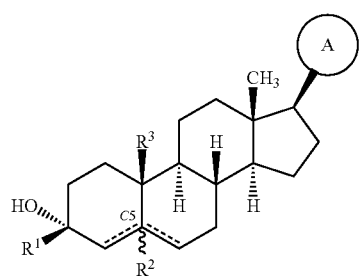

(I)

or a pharmaceutically acceptable salt thereof; wherein: Ring A is aryl or heteroaryl; $R^1$ is hydrogen, $C_{1-3}$ alkyl (e.g., unsubstituted $C_{1-3}$ alkyl (e.g., —$CH_3$, —$CH_2CH_3$) or substituted $C_{1-3}$ alkyl (e.g., $C_{1-3}$ haloalkyl (e.g., —$CHF_2$, —$CH_2F$, —$CF_3$), —$CH_2OCH_3$)), $C_{2-6}$ alkenyl, or $C_{3-6}$ carbocylyl; $R^2$ is absent or hydrogen; $R^3$ is hydrogen, alkyl, or —$CH_2OR^{3A}$, wherein $R^{3A}$ is hydrogen, $C_{1-6}$ alkyl, $C_{2-6}$ alkenyl, $C_{2-6}$ alkynyl, aryl, heteroaryl, or $C_{3-6}$ carbocyclyl; ===== represents a single or double bond, wherein when one ===== is a double bond, the other ===== is a single bond; wherein when $R^1$ is —$CH_3$, $R^2$ is hydrogen in the alpha configuration, and $R^3$ is —$CH_3$, then A is aryl, wherein administering occurs by continuous intravenous infusion.

In some embodiments, when $R^3$ is —$CH_3$, $R^2$ is hydrogen in the beta configuration.

In some embodiments, the subject is a female. In some embodiments, the subject is an adult. In some embodiments, the subject is from 18 to 45 years of age. In some embodiments, the subject is suffering from (e.g., has been diagnosed with) postpartum depression (e.g., severe postpartum depression). In some embodiments, the subject has experienced a Major Depressive Episode in the postpartum period. In some embodiments, the period begins within the first 4 weeks following delivery of a baby.

In one aspect, provided is a method of treating a human subject suffering from tremor, the method comprising administering a therapeutically effective amount of a compound of Formula (I):

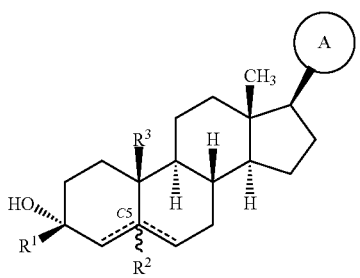

(I)

or a pharmaceutically acceptable salt thereof; wherein: Ring A is aryl or heteroaryl; $R^1$ is hydrogen, $C_{1-3}$ alkyl (e.g., unsubstituted $C_{1-3}$ alkyl (e.g., —$CH_3$, —$CH_2CH_3$) or substituted $C_{1-3}$ alkyl (e.g., $C_{1-3}$ haloalkyl (e.g., —$CHF_2$, —$CH_2F$, —$CF_3$), —$CH_2OCH_3$)), $C_{2-6}$ alkenyl, or $C_{3-6}$ carbocylyl; $R^2$ is absent or hydrogen; $R^3$ is hydrogen, alkyl, or —$CH_2OR^{3A}$, wherein $R^{3A}$ is hydrogen, $C_{1-6}$ alkyl, $C_{2-6}$ alkenyl, $C_{2-6}$ alkynyl, aryl, heteroaryl, or $C_{3-6}$ carbocyclyl; ═══ represents a single or double bond, wherein when one ═══ is a double bond, the other ═══ is a single bond; wherein when $R^1$ is —$CH_3$, $R^2$ is hydrogen in the alpha configuration, and $R^3$ is —$CH_3$, then A is aryl.

In some embodiments, when $R^3$ is —$CH_3$, $R^2$ is hydrogen in the beta configuration.

In some embodiments, the tremor is essential tremor.

In some embodiments, the administering is performed parenterally. In some embodiments, the administering is performed intravenously.

In some embodiments, the administering is performed orally.

In one aspect, provided is a kit comprising a solid composition comprising a compound of Formula (I):

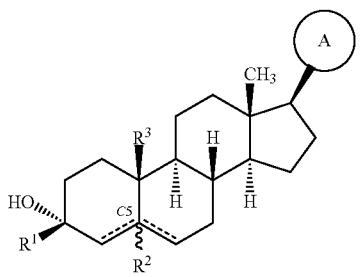

(I)

or a pharmaceutically acceptable salt thereof; wherein: Ring A is aryl or heteroaryl; $R^1$ is hydrogen, $C_{1-3}$ alkyl (e.g., unsubstituted $C_{1-3}$ alkyl (e.g., —$CH_3$, —$CH_2CH_3$) or substituted $C_{1-3}$ alkyl (e.g., $C_{1-3}$ haloalkyl (e.g., —$CHF_2$, —$CH_2F$, —$CF_3$), —$CH_2OCH_3$)), $C_{2-6}$ alkenyl, or $C_{3-6}$ carbocylyl; $R^2$ is absent or hydrogen; $R^3$ is hydrogen, alkyl, or —$CH_2OR^{3A}$, wherein $R^{3A}$ is hydrogen, $C_{1-6}$ alkyl, $C_{2-6}$ alkenyl, $C_{2-6}$ alkynyl, aryl, heteroaryl, or $C_{3-6}$ carbocyclyl; ═══ represents a single or double bond, wherein when one ═══ is a double bond, the other ═══ is a single bond; wherein when $R^1$ is —$CH_3$, $R^2$ is hydrogen in the alpha configuration, and $R^3$ is —$CH_3$, then A is aryl.

In some embodiments, when $R^3$ is —$CH_3$, $R^2$ is hydrogen in the beta configuration.

The present invention also provides pharmaceutical compositions comprising a compound of the present invention and methods of use and treatment, e.g., such as for inducing sedation and/or anesthesia, for treating a CNS-related disorder.

Steroids of Formula (I), sub-genera thereof, and pharmaceutically acceptable salts thereof are collectively referred to herein as "compounds of the present invention."

In another aspect, provided is a pharmaceutical composition comprising a compound of the present invention and a pharmaceutically acceptable excipient. In certain embodiments, the compound of the present invention is provided in an effective amount in the pharmaceutical composition. In certain embodiments, the compound of the present invention is provided in a therapeutically effective amount. In certain embodiments, the compound of the present invention is provided in a prophylactically effective amount.

Compounds of the present invention as described herein, act, in certain embodiments, as GABA modulators, e.g., effecting the $GABA_A$ receptor in either a positive or negative manner. As modulators of the excitability of the central nervous system (CNS), as mediated by their ability to modulate $GABA_A$ receptor, such compounds are expected to have CNS-activity.

Thus, in another aspect, provided are methods of treating a CNS-related disorder in a subject in need thereof, comprising administering to the subject an effective amount of a compound of the present invention. In certain embodiments, the CNS-related disorder is selected from the group consisting of a sleep disorder, a mood disorder, a schizophrenia spectrum disorder, a convulsive disorder, a disorder of memory and/or cognition, a movement disorder (e.g., tremor, for example essential tremor), a personality disorder, autism spectrum disorder, pain, traumatic brain injury, a vascular disease, a substance abuse disorder and/or withdrawal syndrome, and tinnitus. In certain embodiments, the compound is administered orally, subcutaneously, intravenously, or intramuscularly. In certain embodiments, the compound is administered chronically. In certain embodiments, the compound is administered continuously, e.g., by continuous intravenous infusion.

Other objects and advantages will become apparent to those skilled in the art from a consideration of the ensuing Detailed Description, Examples, and Claims.

Definitions

Chemical Definitions

Definitions of specific functional groups and chemical terms are described in more detail below. The chemical elements are identified in accordance with the Periodic Table of the Elements, CAS version, *Handbook of Chemistry and Physics*, 75th Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, 5th Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3rd Edition, Cambridge University Press, Cambridge, 1987.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, N Y, 1962); and Wilen, *Tables of Resolving Agents and Optical Resolutions* p. 268 (E. L. Eliel, Ed., Univ. of Notre Dame Press, Notre Dame, Ind. 1972). The invention additionally encompasses compounds described herein as individual isomers substantially free of other isomers, and alternatively, as mixtures of various isomers.

As used herein a pure enantiomeric compound is substantially free from other enantiomers or stereoisomers of the compound (i.e., in enantiomeric excess). In other words, an "S" form of the compound is substantially free from the "R" form of the compound and is, thus, in enantiomeric excess of the "R" form. The term "enantiomerically pure" or "pure enantiomer" denotes that the compound comprises more than 75% by weight, more than 80% by weight, more than 85% by weight, more than 90% by weight, more than 91% by weight, more than 92% by weight, more than 93% by weight, more than 94% by weight, more than 95% by weight, more than 96% by weight, more than 97% by weight, more than 98% by weight, more than 98.5% by weight, more than 99% by weight, more than 99.2% by weight, more than 99.5% by weight, more than 99.6% by weight, more than 99.7% by weight, more than 99.8% by weight or more than 99.9% by weight, of the enantiomer. In certain embodiments, the weights are based upon total weight of all enantiomers or stereoisomers of the compound.

In the compositions provided herein, an enantiomerically pure compound can be present with other active or inactive ingredients. For example, a pharmaceutical composition comprising enantiomerically pure R-compound can comprise, for example, about 90% excipient and about 10% enantiomerically pure R-compound. In certain embodiments, the enantiomerically pure R-compound in such compositions can, for example, comprise, at least about 95% by weight R-compound and at most about 5% by weight S-compound, by total weight of the compound. For example, a pharmaceutical composition comprising enantiomerically pure S-compound can comprise, for example, about 90% excipient and about 10% enantiomerically pure S-compound. In certain embodiments, the enantiomerically pure S-compound in such compositions can, for example, comprise, at least about 95% by weight S-compound and at most about 5% by weight R-compound, by total weight of the compound. In certain embodiments, the active ingredient can be formulated with little or no excipient or carrier.

Compound described herein may also comprise one or more isotopic substitutions. For example, H may be in any isotopic form, including $^1H$, $^2H$ (D or deuterium), and $^3H$ (T or tritium); C may be in any isotopic form, including $^{12}C$, $^{13}C$, and $^{14}C$; O may be in any isotopic form, including 16O and $^{18}O$; and the like.

The articles "a" and "an" may be used herein to refer to one or to more than one (i.e. at least one) of the grammatical objects of the article. By way of example "an analogue" means one analogue or more than one analogue.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

The following terms are intended to have the meanings presented therewith below and are useful in understanding the description and intended scope of the present invention.

"Alkyl" refers to a radical of a straight-chain or branched saturated hydrocarbon group having from 1 to 20 carbon atoms ("$C_{1-20}$ alkyl"). In some embodiments, an alkyl group has 1 to 12 carbon atoms ("$C_{1-12}$ alkyl"). In some embodiments, an alkyl group has 1 to 8 carbon atoms ("$C_{1-8}$ alkyl"). In some embodiments, an alkyl group has 1 to 6 carbon atoms ("$C_{1-6}$ alkyl", also referred to herein as "lower alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. Unless otherwise specified, each instance of an alkyl group is independently optionally substituted, i.e., unsubstituted (an "unsubstituted alkyl") or substituted (a "substituted alkyl") with one or more substituents; e.g., for instance from 1 to 5 substituents, 1 to 3 substituents, or 1 substituent. In certain embodiments, the alkyl group is unsubstituted $C_{1-10}$ alkyl (e.g., —$CH_3$). In certain embodiments, the alkyl group is substituted $C_{1-10}$ alkyl. Common alkyl abbreviations include Me (—$CH_3$), Et (—$CH_2CH_3$), iPr (—$CH(CH_3)_2$), nPr (—$CH_2CH_2CH_3$), n-Bu (—$CH_2CH_2CH_2CH_3$), or i-Bu (—$CH_2CH(CH_3)_2$).

"Alkenyl" refers to a radical of a straight-chain or branched hydrocarbon group having from 2 to 20 carbon atoms, one or more carbon-carbon double bonds, and no triple bonds ("$C_{2-20}$ alkenyl"). In some embodiments, an alkenyl group has 2 to 10 carbon atoms ("$C_{2-10}$ alkenyl"). In some embodiments, an alkenyl group has 2 to 8 carbon atoms ("$C_{2-8}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently optionally substituted, i.e., unsubstituted (an "unsubstituted alkenyl") or substituted (a "substituted alkenyl") with one or more substituents e.g., for instance from 1 to 5 substituents, 1 to 3 substituents, or 1 substituent. In certain embodiments, the alkenyl group is unsubstituted $C_{2-10}$ alkenyl. In certain embodiments, the alkenyl group is substituted $C_{2-10}$ alkenyl.

"Alkynyl" refers to a radical of a straight-chain or branched hydrocarbon group having from 2 to 20 carbon atoms, one or more carbon-carbon triple bonds, and optionally one or more double bonds ("$C_{2-20}$ alkynyl"). In some embodiments, an alkynyl group has 2 to 10 carbon atoms ("$C_{2-10}$ alkynyl"). In some embodiments, an alkynyl group has 2 to 8 carbon atoms ("$C_{2-8}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently optionally substituted, i.e., unsubstituted (an "unsubstituted alkynyl") or substituted (a "substituted alkynyl") with one or more substituents; e.g., for instance from 1 to 5 substituents, 1 to 3 substituents, or 1 substituent. In certain embodiments, the alkynyl group is unsubstituted $C_{2-10}$ alkynyl. In certain embodiments, the alkynyl group is substituted $C_{2-10}$ alkynyl.

"Aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Aryl groups include, but are not limited to, phenyl, naphthyl, indenyl, and tetrahydronaphthyl. Unless otherwise specified, each instance of an aryl group is independently optionally substituted, i.e., unsubstituted (an "unsubstituted aryl") or substituted (a "substituted aryl") with one or more substituents. In certain embodiments, the aryl group is unsubstituted $C_{6-14}$ aryl. In certain embodiments, the aryl group is substituted $C_{6-14}$ aryl.

In certain embodiments, an aryl group substituted with one or more of groups selected from halo, $C_1$-$C_8$ alkyl, $C_1$-$C_8$ haloalkyl, cyano, hydroxy, $C_1$-$C_8$ alkoxy, and amino.

Examples of representative substituted aryls include the following

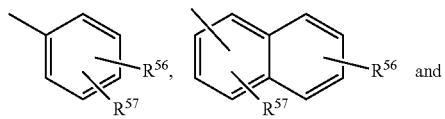

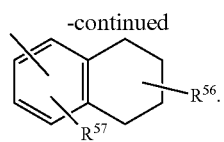

wherein one of $R^{56}$ and $R^{57}$ may be hydrogen and at least one of $R^{56}$ and $R^{57}$ is each independently selected from $C_1$-$C_8$ alkyl, $C_1$-$C_8$ haloalkyl, 4-10 membered heterocyclyl, alkanoyl, $C_1$-$C_8$ alkoxy, heteroaryloxy, alkylamino, arylamino, heteroarylamino, $NR^{58}COR^{59}$, $NR^{58}SOR^{59}$ $NR^{58}SO_2R^{59}$, COOalkyl, COOaryl, $CONR^{58}R^{59}$, $CONR^{58}OR^{59}$, $NR^{58}R^{59}$ $SO_2NR^{58}R^{59}$, S-alkyl, SOalkyl, $SO_2$alkyl, Saryl, SOaryl, $SO_2$aryl; or $R^{56}$ and $R^{57}$ may be joined to form a cyclic ring (saturated or unsaturated) from 5 to 8 atoms, optionally containing one or more heteroatoms selected from the group N, O, or S. $R^{60}$ and $R^{61}$ are independently hydrogen, $C_1$-$C_8$ alkyl, $C_1$-$C_4$ haloalkyl, $C_3$-$C_{10}$ cycloalkyl, 4-10 membered heterocyclyl, $C_6$-$C_{10}$ aryl, substituted $C_6$-$C_{10}$ aryl, 5-10 membered heteroaryl, or substituted 5-10 membered heteroaryl.

Other representative aryl groups having a fused heterocyclyl group include the following:

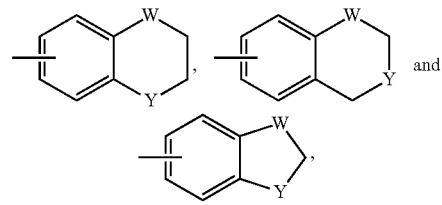

wherein each W is selected from $C(R^{66})_2$, $NR^{66}$, O, and S; and each Y is selected from carbonyl, $NR^{66}$, O and S; and $R^{66}$ is independently hydrogen, $C_1$-$C_8$ alkyl, $C_3$-$C_{10}$ cycloalkyl, 4-10 membered heterocyclyl, $C_6$-$C_{10}$ aryl, and 5-10 membered heteroaryl.

"Halo" or "halogen," independently or as part of another substituent, mean, unless otherwise stated, a fluorine (F), chlorine (Cl), bromine (Br), or iodine (I) atom. The term "halide" by itself or as part of another substituent, refers to a fluoride, chloride, bromide, or iodide atom. In certain embodiments, the halo group is either fluorine or chlorine.

"Haloalkyl" and "haloalkoxy" can include alkyl and alkoxy structures that are substituted with one or more halo groups or with combinations thereof. For example, the terms "fluoroalkyl" and "fluoroalkoxy" include haloalkyl and haloalkoxy groups, respectively, in which the halo is fluorine.

"Heteroaryl" refers to a radical of a 5-10 membered monocyclic or bicyclic 4n+2 aromatic ring system (e.g., having 6 or 10 π electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently optionally substituted, i.e., unsubstituted (an "unsubstituted heteroaryl") or substituted (a "substituted heteroaryl") with one or more substituents. In certain embodiments, the heteroaryl group is unsubstituted 5-14 membered heteroaryl. In certain embodiments, the heteroaryl group is substituted 5-14 membered heteroaryl.

Exemplary 5-membered heteroaryl groups containing one heteroatom include, without limitation, pyrrolyl, furanyl and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

Examples of representative heteroaryls include the following formulae:

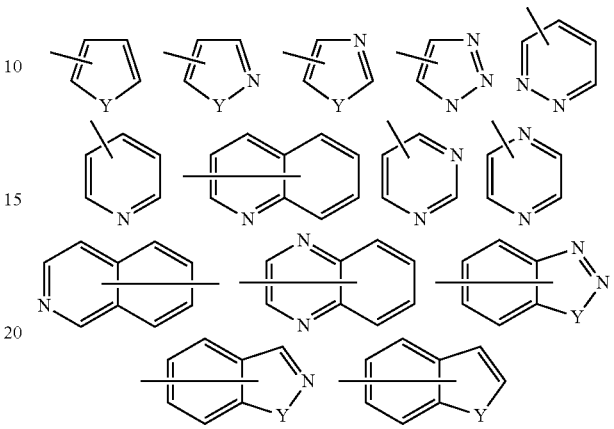

wherein each Y is selected from carbonyl, N, NR$^{65}$, O, and S; and R$^{65}$ is independently hydrogen, $C_1$-$C_8$ alkyl, $C_3$-$C_{10}$ cycloalkyl, 4-10 membered heterocyclyl, $C_6$-$C_{10}$ aryl, and 5-10 membered heteroaryl.

"Carbocyclyl" or "carbocyclic" refers to a radical of a non-aromatic cyclic hydrocarbon group having from 3 to 10 ring carbon atoms ("$C_{3-10}$ carbocyclyl") and zero heteroatoms in the non-aromatic ring system. In some embodiments, a carbocyclyl group has 3 to 8 ring carbon atoms ("$C_{3-8}$ carbocyclyl"). In some embodiments, a carbocyclyl group has 3 to 6 ring carbon atoms ("$C_{3-6}$ carbocyclyl"). In some embodiments, a carbocyclyl group has 3 to 6 ring carbon atoms ("$C_{3-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{38}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or contain a fused, bridged or spiro ring system such as a bicyclic system ("bicyclic carbocyclyl") and can be saturated or can be partially unsaturated. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently optionally substituted, i.e., unsubstituted (an "unsubstituted carbocyclyl") or substituted (a "substituted carbocyclyl") with one or more substituents. In certain embodiments, the carbocyclyl group is unsubstituted $C_{3-10}$ carbocyclyl. In certain embodiments, the carbocyclyl group is a substituted $C_{3-10}$ carbocyclyl.

In some embodiments, "carbocyclyl" is a monocyclic, saturated carbocyclyl group having from 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{56}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is unsubstituted $C_{3-10}$ cycloalkyl. In certain embodiments, the cycloalkyl group is substituted $C_{3-10}$ cycloalkyl.

"Heterocyclyl" or "heterocyclic" refers to a radical of a 3- to 10-membered non-aromatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged or spiro ring system such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently optionally substituted, i.e., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, sulfur, boron, phosphorus, and silicon ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, azirdinyl, oxiranyl, thiorenyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, dioxanyl. Exemplary 6-membered heterocyclyl groups containing two heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

Particular examples of heterocyclyl groups are shown in the following illustrative examples:

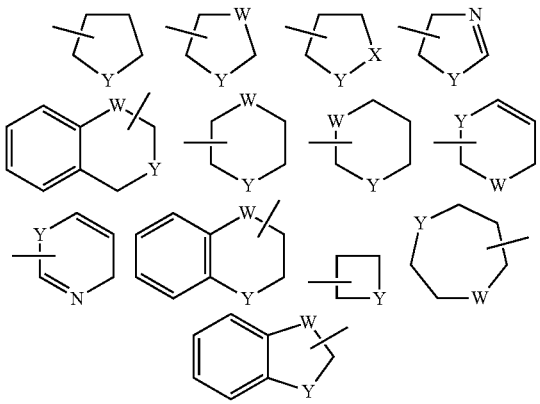

wherein each W is selected from $CR^{67}$, $C(R^{67})_2$, $NR^{67}$, O, and S; and each Y is selected from $NR^{67}$, O, and S; and $R^{67}$ is independently hydrogen, $C_1$-$C_8$ alkyl, $C_3$-$C_{10}$ cycloalkyl, 4-10 membered heterocyclyl, $C_6$-$C_{10}$ aryl, and 5-10-membered heteroaryl. These heterocyclyl rings may be optionally substituted with one or more groups selected from the group consisting of acyl, acylamino, acyloxy, alkoxy, alkoxycarbonyl, alkoxycarbonylamino, amino, substituted amino, aminocarbonyl (e.g., amido), aminocarbonylamino, aminosulfonyl, sulfonylamino, aryl, aryloxy, azido, carboxyl, cyano, cycloalkyl, halogen, hydroxy, keto, nitro, thiol, —S-alkyl, —S-aryl, —S(O)-alkyl, —S(O)-aryl, —S(O)$_2$-alkyl, and —S(O)$_2$-aryl. Substituting groups include carbonyl or thiocarbonyl which provide, for example, lactam and urea derivatives.

"Acyl" refers to a radical —C(O)R$^{20}$, where R$^{20}$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, as defined herein. "Alkanoyl" is an acyl group wherein R$^{20}$ is a group other than hydrogen. Representative acyl groups include, but are not limited to, formyl (—CHO), acetyl (—C(=O)CH$_3$), cyclohexylcarbonyl, cyclohexylmethylcarbonyl, benzoyl (—C(=O)Ph), benzylcarbonyl (—C(=O)CH$_2$Ph), —C(O)—$C_1$-$C_5$ alkyl, —C(O)—(CH$_2$)$_t$($C_6$-$C_{10}$ aryl), —C(O)—(CH$_2$)$_t$(5-10 membered heteroaryl), —C(O)—(CH$_2$)$_t$($C_3$-$C_{10}$ cycloalkyl), and —C(O)—(CH$_2$)$_t$(4-10 membered heterocyclyl), wherein t is an integer from 0 to 4. In certain embodiments, R$^{21}$ is $C_1$-$C_8$ alkyl, substituted with halo or hydroxy; or $C_3$-$C_{10}$ cycloalkyl, 4-10 membered heterocyclyl, $C_6$-$C_{10}$ aryl, arylalkyl, 5-10 membered heteroaryl or heteroarylalkyl, each of which is substituted with unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy.

"Acylamino" refers to a radical —NR$^{22}$C(O)R$^{23}$, where each instance of R$^{22}$ and R$^{23}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, as defined herein, or R$^{22}$ is an amino protecting group. Exemplary "acylamino" groups include, but are not limited to, formylamino, acetylamino, cyclohexylcarbonylamino, cyclohexylmethyl-carbonylamino, benzoylamino and benzylcarbonylamino. Particular exemplary "acylamino" groups are —NR$^{24}$C(O)—$C_1$-$C_8$ alkyl, —NR$^{24}$C(O)—(CH$_2$)$_t$($C_6$-$C_1$ aryl), —NR$^{24}$C(O)—(CH$_2$)$_t$(5-10 membered heteroaryl), —NR$^{24}$C(O)—(CH$_2$)$_t$($C_3$-$C_{10}$ cycloalkyl), and —NR$^{24}$C(O)—(CH$_2$)$_t$(4-10 membered heterocyclyl), wherein t is an integer from 0 to 4, and each R$^{24}$ independently represents hydrogen or $C_1$-$C_8$ alkyl. In certain embodiments, R$^{25}$ is H, $C_1$-$C_8$ alkyl, substituted with halo or hydroxy; $C_3$-$C_{10}$ cycloalkyl, 4-10 membered heterocyclyl, $C_6$-$C_{10}$ aryl, arylalkyl, 5-10 membered heteroaryl or heteroarylalkyl, each of which is substituted with unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy; and R$^{26}$ is H, $C_1$-$C_8$ alkyl, substituted with halo or hydroxy; $C_3$-$C_{10}$ cycloalkyl, 4-10-membered heterocyclyl, $C_6$-$C_{10}$ aryl, arylalkyl, 5-10 membered heteroaryl or heteroarylalkyl, each of which is substituted with unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy; provided at least one of R$^{25}$ and R$^{26}$ is other than H.

"Acyloxy" refers to a radical —OC(O)R$^{27}$, where R$^{27}$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, as defined herein. Representative examples include, but are not limited to, formyl, acetyl, cyclohexylcarbonyl, cyclohexylmethylcarbonyl, benzoyl, and benzylcarbonyl. In certain embodiments, R$^{28}$ is $C_1$-$C_8$ alkyl, substituted with halo or hydroxy; $C_3$-$C_{10}$ cycloalkyl, 4-10-membered heterocyclyl, $C_6$-$C_{10}$ aryl, arylalkyl, 5-10-membered heteroaryl or heteroarylalkyl, each of which is substituted with unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy.

"Alkoxy" refers to the group —OR$^{29}$ where R$^{29}$ is substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl. Particular alkoxy groups are methoxy, ethoxy, n-propoxy, isopropoxy, n-butoxy, tert-butoxy, sec-butoxy, n-pentoxy, n-hexoxy, and 1,2-dimethylbutoxy. Particular alkoxy groups are lower alkoxy, i.e., with between 1 and 6 carbon atoms. Further particular alkoxy groups have between 1 and 4 carbon atoms.

In certain embodiments, R$^{29}$ is a group that has 1 or more substituents, for instance from 1 to 5 substituents, and particularly from 1 to 3 substituents, in particular 1 substituent, selected from the group consisting of amino, substituted amino, $C_6$-$C_{10}$ aryl, aryloxy, carboxyl, cyano, $C_3$-$C_{10}$ cycloalkyl, 4-10 membered heterocyclyl, halogen, 5-10 membered heteroaryl, hydroxy, nitro, thioalkoxy, thioaryloxy, thiol, alkyl—S(O)—, aryl—S(O)—, alkyl—S(O)$_2$— and aryl—S(O)$_2$—. Exemplary "substituted alkoxy" groups include, but are not limited to, —O—(CH$_2$)$_t$($C_6$-$C_{10}$ aryl), —O—(CH$_2$)$_t$(5-10 membered heteroaryl), —O—(CH$_2$)$_t$($C_3$-$C_{10}$ cycloalkyl), and —O—(CH$_2$)$_t$(4-10 membered heterocyclyl), wherein t is an integer from 0 to 4 and any aryl, heteroaryl, cycloalkyl or heterocyclyl groups present, may themselves be substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy. Particular exemplary 'substituted alkoxy' groups are —OCF$_3$, —OCH$_2$CF$_3$, —OCH$_2$Ph, —OCH$_2$-cyclopropyl, —OCH$_2$CH$_2$OH, and —OCH$_2$CH$_2$NMe$_2$.

"Amino" refers to the radical —NH$_2$.

"Substituted amino" refers to an amino group of the formula —N(R$^{38}$)$_2$ wherein R$^{38}$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or an amino protecting group, wherein at least one of R$^{38}$ is not a hydrogen. In certain embodiments, each R$^{38}$ is independently selected from hydrogen, $C_1$-$C_8$ alkyl, $C_3$-$C_8$ alkenyl, $C_3$-$C_8$ alkynyl, $C_6$-$C_{10}$ aryl, 5-10 membered heteroaryl, 4-10 membered heterocyclyl, or $C_3$-$C_{10}$ cycloalkyl; or $C_1$-$C_8$ alkyl, substituted with halo or hydroxy; $C_3$-$C_8$ alkenyl, substituted with halo or hydroxy; $C_3$-$C_8$ alkynyl, substituted with halo or hydroxy, or —(CH$_2$)$_t$($C_6$-$C_{10}$ aryl), —(CH$_2$)$_t$(5-10 membered heteroaryl), —(CH$_2$)$_t$($C_3$-$C_{10}$ cycloalkyl), or —(CH$_2$)$_t$(4-10 membered heterocyclyl), wherein t is an integer between 0 and 8, each of which is substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy; or both $R^{38}$ groups are joined to form an alkylene group.

Exemplary "substituted amino" groups include, but are not limited to, —$NR^{39}$—$C_1$-$C_8$ alkyl, —$NR^{39}$—$(CH_2)_t(C_6$-$C_{10}$ aryl), —$NR^{39}$—$(CH_2)_t$(5-10 membered heteroaryl), —$NR^{39}$—$(CH_2)_t(C_3$-$C_{10}$ cycloalkyl), and —$NR^{39}$—$(CH_2)_t$ (4-10 membered heterocyclyl), wherein t is an integer from 0 to 4, for instance 1 or 2, each $R^{39}$ independently represents hydrogen or $C_1$-$C_8$ alkyl; and any alkyl groups present, may themselves be substituted by halo, substituted or unsubstituted amino, or hydroxy; and any aryl, heteroaryl, cycloalkyl, or heterocyclyl groups present, may themselves be substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy. For the avoidance of doubt the term 'substituted amino' includes the groups alkylamino, substituted alkylamino, alkylarylamino, substituted alkylarylamino, arylamino, substituted arylamino, dialkylamino, and substituted dialkylamino as defined below. Substituted amino encompasses both monosubstituted amino and disubstituted amino groups.

"Azido" refers to the radical —$N_3$.

"Carbamoyl" or "amido" refers to the radical —$C(O)NH_2$.

"Substituted carbamoyl" or "substituted amido" refers to the radical —$C(O)N(R^{62})_2$ wherein each $R^{62}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or an amino protecting group, wherein at least one of $R^{62}$ is not a hydrogen. In certain embodiments, $R^{62}$ is selected from H, $C_1$-$C_8$ alkyl, $C_3$-$C_{10}$ cycloalkyl, 4-10 membered heterocyclyl, $C_6$-$C_{10}$ aryl, and 5-10 membered heteroaryl; or $C_1$-$C_8$ alkyl substituted with halo or hydroxy; or $C_3$-$C_{10}$ cycloalkyl, 4-10 membered heterocyclyl, $C_6$-$C_{10}$ aryl, or 5-10 membered heteroaryl, each of which is substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy; provided that at least one $R^{62}$ is other than H.

"Carboxy" refers to the radical —C(O)OH.

"Cyano" refers to the radical —CN.

"Hydroxy" refers to the radical —OH.

"Nitro" refers to the radical —$NO_2$.

"Ethenyl" refers to substituted or unsubstituted —(C≡C)—. "Ethylene" refers to substituted or unsubstituted —(C—C)—. "Ethynyl" refers to —(C≡C)—.

"Nitrogen-containing heterocyclyl" group means a 4- to 7-membered non-aromatic cyclic group containing at least one nitrogen atom, for example, but without limitation, morpholine, piperidine (e.g. 2-piperidinyl, 3-piperidinyl and 4-piperidinyl), pyrrolidine (e.g. 2-pyrrolidinyl and 3-pyrrolidinyl), azetidine, pyrrolidone, imidazoline, imidazolidinone, 2-pyrazoline, pyrazolidine, piperazine, and N-alkyl piperazines such as N-methyl piperazine. Particular examples include azetidine, piperidone and piperazone.

Alkyl, alkenyl, alkynyl, carbocyclyl, heterocyclyl, aryl, and heteroaryl groups, as defined herein, are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety.

Exemplary carbon atom substituents include, but are not limited to, halogen, —CN, —$NO_2$, —$N_3$, —$SO_2H$, —$SO_3H$, —OH, —$OR^{aa}$, —$ON(R^{bb})_2$, —$N(R^{bb})_2$, —$N(R^{bb})_3^+X^-$, —$N(OR^{cc})R^{bb}$, —SH, —$SR^{aa}$, —$SSR^{cc}$, —$C(=O)R^{aa}$, —$CO_2H$, —CHO, —$C(OR^{cc})_2$, —$CO_2R^{aa}$, —$OC(=O)R^{aa}$, —$OCO_2R^{aa}$, —$C(=O)N(R^{bb})_2$, —$OC(=O)N(R^{bb})_2$, —$NR^{bb}C(=O)R^{aa}$, —$NR^{bb}CO_2R^{aa}$, —$NR^{bb}C(=O)N(R^{bb})_2$, —$C(=NR^{bb})R^{aa}$, —$C(=NR^{bb})OR^{aa}$, —$OC(=NR^{bb})R^{aa}$, —$OC(=NR^{bb})OR^{aa}$, —$C(=NR^{bb})N(R^{bb})_2$, —$OC(=NR^{bb})N(R^{bb})_2$, —$NR^{bb}C(=NR^{bb})N(R^{bb})_2$, —$C(=O)NR^{bb}SO_2R^{aa}$, —$NR^{bb}SO_2R^{aa}$, —$SO_2N(R^{bb})_2$, —$SO_2R^{aa}$, —$SO_2OR$, —$OSO_2R$, —$S(=O)R^{aa}$, —$OS(=O)R^{aa}$, —$Si(R^{aa})_3$, —$OSi(R^{aa})_3$, —$C(=S)N(R^{bb})_2$, —$C(=O)SR^{aa}$, —$C(=S)SR^{aa}$, —$SC(=S)SR^{aa}$, —$SC(=O)SR^{aa}$, —$OC(=O)SR^{aa}$, —$SC(=O)OR^{aa}$, —$SC(=O)R^{aa}$, —$P(=O)_2R$, —$OP(=O)_2R$, —$P(=O)(R^{aa})_2$, —$OP(=O)(R^{aa})_2$, —$OP(=O)(OR^{cc})_2$, —$P(=O)_2N(R^{bb})_2$, —$OP(=O)_2N(R^{bb})_2$, —$P(=O)(NR^{bb})_2$, —$OP(=O)(NR^{bb})_2$, —$NR^{bb}P(=O)(OR^{cc})_2$, —$NR^{bb}P(=O)(NR^{bb})_2$, —$P(R^{cc})_2$, —$P(R^{cc})_3$, —$OP(R^{cc})_2$, —$OP(R^{cc})_3$, —$B(R^{aa})_2$, —$B(OR^{cc})_2$, —$BR^{aa}(OR^{cc})$, $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 $R^{dd}$ groups;

each instance of $R^{aa}$ is, independently, selected from $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{aa}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups;

each instance of $R^{bb}$ is, independently, selected from hydrogen, —OH, —$OR^{aa}$, —$N(R^{cc})_2$, —CN, —$C(=O)R^{aa}$, —$C(=O)N(R^{cc})_2$, —$CO_2R^{aa}$, —$SO_2R^{aa}$, —$C(=NR^{cc})OR^{aa}$, —$C(=NR^{cc})N(R^{cc})_2$, —$SO_2N(R^{cc})_2$, —$SO_2R^{cc}$, —$SO_2OR^{cc}$, —$SOR^{aa}$, —$C(=S)N(R^{cc})_2$, —$C(=O)SR^{cc}$, —$C(=S)SR^{cc}$, —$P(=O)_2R^{aa}$, —$P(=O)(R^{aa})_2$, —$P(=O)_2N(R^{cc})_2$, —$P(=O)(NR^{cc})_2$, $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{bb}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups;

each instance of $R^{cc}$ is, independently, selected from hydrogen, $C_{1-10}$alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{cc}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups;

each instance of $R^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3$$^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)$_2$R$^{ee}$, —P(=O)(R$^{ee}$)$_2$, —OP(=O)(R$^{ee}$)$_2$, —OP(=O)(OR$^{ee}$)$_2$, $C_{1-6}$ alkyl, $C_{1-6}$ perhaloalkyl, $C_{2-6}$ alkenyl, $C_{2-6}$ alkynyl, $C_{3-10}$ carbocyclyl, 3-10 membered heterocyclyl, $C_{6-10}$ aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 $R^{gg}$ groups;

each instance of $R^{ee}$ is, independently, selected from $C_{1-6}$ alkyl, $C_1$— perhaloalkyl, $C_{2-6}$ alkenyl, $C_{2-6}$ alkynyl, $C_{3-10}$ carbocyclyl, $C_{6-10}$ aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 $R^{gg}$ groups;

each instance of $R^{ff}$ is, independently, selected from hydrogen, $C_{1-6}$ alkyl, $C_{1-6}$ perhaloalkyl, $C_{2-6}$ alkenyl, $C_{2-6}$ alkynyl, $C_{3-10}$ carbocyclyl, 3-10 membered heterocyclyl, $C_{6-10}$ aryl and 5-10 membered heteroaryl, or two $R^{ff}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{gg}$ groups; and each instance of $R^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$$^+$X$^-$, —NH(C$_{1-6}$ alkyl)$_2$$^+$X$^-$, —NH$_2$(C$_{1-6}$ alkyl)$^+$X$^-$, —NH$_3$$^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$alkyl, —SO$_2$OC$_{1-6}$ alkyl, —OSO$_2$C$_{1-6}$alkyl, —SOC$_{1-6}$ alkyl, —Si(C$_{1-6}$ alkyl)$_3$, —OSi(C$_{1-6}$ alkyl)$_3$-C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)$_2$(C$_{1-6}$ alkyl), —P(=O)(C$_{1-6}$ alkyl)$_2$, —OP(=O)(C$_{1-6}$ alkyl)$_2$, —OP(=O)(OC$_{1-6}$ alkyl)$_2$, $C_{1-6}$ alkyl, $C_{1-6}$ perhaloalkyl, $C_{2-6}$ alkenyl, $C_{2-6}$ alkynyl, $C_{3-10}$ carbocyclyl, $C_{6-10}$ aryl, 3-10 membered heterocyclyl, 5-10 membered heteroaryl; wherein X$^-$ is a counterion.

A "counterion" or "anionic counterion" is a negatively charged group associated with a cationic quaternary amino group in order to maintain electronic neutrality. Exemplary counterions include halide ions (e.g., F$^-$, C$^-$, Br$^-$, I$^-$), NO$_3$$^-$, ClO$_4$$^-$, OH$^-$, H$_2$PO$_4$$^-$, HSO$_4$$^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), and carboxylate ions (e.g., acetate, ethanoate, propanoate, benzoate, glycerate, lactate, tartrate, glycolate, and the like).

Nitrogen atoms can be substituted or unsubstituted as valency permits, and include primary, secondary, tertiary, and quarternary nitrogen atoms. Exemplary nitrogen atom substitutents include, but are not limited to, hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R, —P(=O)(R$^{aa}$)$_2$, —P(=O)$_2$N(R$^{cc}$)$_2$, —P(=O)(NR$^{cc}$)$_2$, $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14-membered heteroaryl, or two $R^{cc}$ groups attached to a nitrogen atom are joined to form a 3-14-membered heterocyclyl or 5-14-membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined above.

In certain embodiments, the substituent present on a nitrogen atom is an amino protecting group (also referred to herein as a nitrogen protecting group). Amino protecting groups include, but are not limited to, —OH, —OR, —N(R$^{cc}$)$_2$, —C(=O)R$^{aa}$, —C(=O)OR$^{aa}$, —C(=O)N(R$^{cc}$)$_2$, —S(=O)$_2$R$^{aa}$, —C(=NR$^{cc}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, $C_{1-10}$alkyl, $C_{2-10}$ alkenyl, $C_{2-10}$ alkynyl, $C_{3-10}$ carbocyclyl, 3-14-membered heterocyclyl, $C_{6-14}$ aryl, and 5-14-membered heteroaryl groups, wherein each alkyl, alkenyl, alkynyl, carbocyclyl, heterocyclyl, aryl, and heteroaryl is independently substituted with 0, 1, 2, 3, 4, or 5 $R^{dd}$ groups, and wherein $R^{aa}$, $R^{bb}$ $R^{cc}$ and $R^{dd}$ are as defined herein. Amino protecting groups are well known in the art and include those described in detail in *Protecting Groups in Organic Synthesis*, T. W. Greene and P. G. M. Wuts, 3rd edition, John Wiley & Sons, 1999, incorporated herein by reference.

Exemplary amino protecting groups include, but are not limited to amide groups (e.g., —C(=O)R$^{aa}$), which include, but are not limited to, formamide and acetamide; carbamate groups (e.g., —C(=O)OR$^{aa}$), which include, but are not limited to, 9-fluorenylmethyl carbamate (Fmoc), t-butyl carbamate (BOC), and benzyl carbamate (Cbz); sulfonamide groups (e.g., —S(=O)$_2$R$^{aa}$), which include, but are not limited to, p-toluenesulfonamide (Ts), methanesulfonamide (Ms), and N-[2-(trimethylsilyl)ethoxy]methylamine (SEM).

In certain embodiments, the substituent present on an oxygen atom is an oxygen protecting group (also referred to as a hydroxyl protecting group). Oxygen protecting groups include, but are not limited to, —$R^{aa}$, —$N(R^{bb})_2$, —C(=O)$SR^{aa}$, —C(=O)$R^{aa}$, —$CO_2R^{aa}$, —C(=O)$N(R^{bb})_2$, —C(=$NR^{bb}$)$R^{aa}$, —C(=$NR^{bb}$)$OR^{aa}$, —C(=$NR^{bb}$)$N(R^{bb})_2$, —S(=O)$R^{aa}$, —$SO_2R^{aa}$, —Si$(R^{aa})_3$, —P$(R^{cc})_2$, —P$(R^{cc})_3$, —P(=O)$_2R^{aa}$, —P(=O)$(R^{aa})_2$, —P(=O)$(OR^{cc})_2$, —P(=O)$_2N(R^{bb})_2$, and —P(=O)$(NR^{bb})_2$, wherein $R^{aa}$, $R^{bb}$, and $R^{cc}$ are as defined herein. Oxygen protecting groups are well known in the art and include those described in detail in *Protecting Groups in Organic Synthesis*, T. W. Greene and P. G. M. Wuts, 3rd edition, John Wiley & Sons, 1999, incorporated herein by reference.

Exemplary oxygen protecting groups include, but are not limited to, methyl, methoxylmethyl (MOM), 2-methoxyethoxymethyl (MEM), benzyl (Bn), triisopropylsilyl (TIPS), t-butyldimethylsilyl (TBDMS), t-butylmethoxyphenylsilyl (TBMPS), methanesulfonate (mesylate), and tosylate (Ts).

In certain embodiments, the substituent present on an sulfur atom is an sulfur protecting group (also referred to as a thiol protecting group). Sulfur protecting groups include, but are not limited to, —$R^{aa}$, —$N(R^{bb})_2$, —C(=O)$SR^{aa}$, —C(=O)$R^{aa}$, —$CO_2R^{aa}$, —C(=O)$N(R^{bb})_2$, —C(=$NR^{bb}$)$R^{aa}$, —C(=$NR^{bb}$)$OR^{aa}$, —C(=$NR^{bb}$)$N(R^{bb})_2$, —S(=O)$R^{aa}$, —$SO_2R$, —Si$(R^{aa})_3$, —P$(R^{cc})_2$, —P$(R^{cc})_3$, —P(=O)$_2R^{aa}$, —P(=O)$(R^{aa})_2$, —P(=O)$(OR^{cc})_2$, —P(=O)$_2N(R^{bb})_2$, and —P(=O)$(NR^{bb})_2$, wherein $R^{aa}$, $R^{bb}$, and $R^{cc}$ are as defined herein. Sulfur protecting groups are well known in the art and include those described in detail in *Protecting Groups in Organic Synthesis*, T. W. Greene and P. G. M. Wuts, 3rd edition, John Wiley & Sons, 1999, incorporated herein by reference.

These and other exemplary substituents are described in more detail in the Detailed Description, Examples, and Claims. The invention is not intended to be limited in any manner by the above exemplary listing of substituents.

Other Definitions

As used herein, the term "modulation" refers to the inhibition or potentiation of GABA receptor function. A "modulator" (e.g., a modulator compound) may be, for example, an agonist, partial agonist, antagonist, or partial antagonist of the GABA receptor.

"Pharmaceutically acceptable" means approved or approvable by a regulatory agency of the Federal or a state government or the corresponding agency in countries other than the United States, or that is listed in the U.S. Pharmacopoeia or other generally recognized pharmacopoeia for use in animals, and more particularly, in humans.

"Pharmaceutically acceptable salt" refers to a salt of a compound of the invention that is pharmaceutically acceptable and that possesses the desired pharmacological activity of the parent compound. In particular, such salts are non-toxic may be inorganic or organic acid addition salts and base addition salts. Specifically, such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethanedisulfonic acid, 2-hydroxyethanesulfonic acid, benzenesulfonicacid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine and the like. Salts further include, by way of example only, sodium, potassium, calcium, magnesium, ammonium, tetraalkylammonium, and the like; and when the compound contains a basic functionality, salts of non-toxic organic or inorganic acids, such as hydrochloride, hydrobromide, tartrate, mesylate, acetate, maleate, oxalate and the like. The term "pharmaceutically acceptable cation" refers to an acceptable cationic counterion of an acidic functional group. Such cations are exemplified by sodium, potassium, calcium, magnesium, ammonium, tetraalkylammonium cations, and the like. See, e.g., Berge, et al., *J. Pharm. Sci.* (1977) 66(1): 1-79.

"Solvate" refers to forms of the compound that are associated with a solvent or water (also referred to as "hydrate"), usually by a solvolysis reaction. This physical association includes hydrogen bonding. Conventional solvents include water, ethanol, acetic acid, and the like. The compounds of the invention may be prepared e.g. in crystalline form and may be solvated or hydrated. Suitable solvates include pharmaceutically acceptable solvates, such as hydrates, and further include both stoichiometric solvates and non-stoichiometric solvates. In certain instances the solvate will be capable of isolation, for example when one or more solvent molecules are incorporated in the crystal lattice of the crystalline solid. "Solvate" encompasses both solution-phase and isolable solvates. Representative solvates include hydrates, ethanolates and methanolates.

As used herein, the term "isotopic variant" refers to a compound that contains unnatural proportions of isotopes at one or more of the atoms that constitute such compound. For example, an "isotopic variant" of a compound can contain one or more non-radioactive isotopes, such as for example, deuterium ($^2$H or D), carbon-13 ($^{13}$C), nitrogen-15 ($^{15}$N), or the like. It will be understood that, in a compound where such isotopic substitution is made, the following atoms, where present, may vary, so that for example, any hydrogen may be $^2$H/D, any carbon may be $^{13}$C, or any nitrogen may be 15N, and that the presence and placement of such atoms may be determined within the skill of the art. Likewise, the invention may include the preparation of isotopic variants with radioisotopes, in the instance for example, where the resulting compounds may be used for drug and/or substrate tissue distribution studies. The radioactive isotopes tritium, i.e., $^3$H, and carbon-14, i.e., $^{14}$C, are particularly useful for this purpose in view of their ease of incorporation and ready means of detection. Further, compounds may be prepared that are substituted with positron emitting isotopes, such as $^{11}$C, $^{18}$F, $^{15}$O, and $^{13}$N, and would be useful in Positron Emission Topography (PET) studies for examining substrate receptor occupancy. All isotopic variants of the compounds provided herein, radioactive or not, are intended to be encompassed within the scope of the invention.

"Stereoisomers": It is also to be understood that compounds that have the same molecular formula but differ in the nature or sequence of bonding of their atoms or the arrangement of their atoms in space are termed "isomers." Isomers that differ in the arrangement of their atoms in space are termed "stereoisomers." Stereoisomers that are not mirror images of one another are termed "diastereomers" and those that are non-superimposable mirror images of each other are termed "enantiomers." When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

"Tautomers" refer to compounds that are interchangeable forms of a particular compound structure, and that vary in the displacement of hydrogen atoms and electrons. Thus, two structures may be in equilibrium through the movement of π electrons and an atom (usually H). For example, enols and ketones are tautomers because they are rapidly interconverted by treatment with either acid or base. Another example of tautomerism is the aci- and nitro-forms of phenylnitromethane, that are likewise formed by treatment with acid or base. Tautomeric forms may be relevant to the attainment of the optimal chemical reactivity and biological activity of a compound of interest.

A "subject" to which administration is contemplated includes, but is not limited to, humans (i.e., a male or female of any age group, e.g., a pediatric subject (e.g, infant, child, adolescent) or adult subject (e.g., young adult, middle-aged adult or senior adult)) and/or a non-human animal, e.g., a mammal such as primates (e.g., cynomolgus monkeys, rhesus monkeys), cattle, pigs, horses, sheep, goats, rodents, cats, and/or dogs. In certain embodiments, the subject is a human. In certain embodiments, the subject is a non-human animal. The terms "human," "patient," and "subject" are used interchangeably herein.

Disease, disorder, and condition are used interchangeably herein.

As used herein, and unless otherwise specified, the terms "treat," "treating" and "treatment" contemplate an action that occurs while a subject is suffering from the specified disease, disorder or condition, which reduces the severity of the disease, disorder or condition, or retards or slows the progression of the disease, disorder or condition ("therapeutic treatment"), and also contemplates an action that occurs before a subject begins to suffer from the specified disease, disorder or condition ("prophylactic treatment").

In general, the "effective amount" of a compound refers to an amount sufficient to elicit the desired biological response, e.g., to treat a CNS-related disorder, is sufficient to induce anesthesia or sedation. As will be appreciated by those of ordinary skill in this art, the effective amount of a compound of the invention may vary depending on such factors as the desired biological endpoint, the pharmacokinetics of the compound, the disease being treated, the mode of administration, and the age, weight, health, and condition of the subject. An effective amount encompasses therapeutic and prophylactic treatment.

As used herein, and unless otherwise specified, a "therapeutically effective amount" of a compound is an amount sufficient to provide a therapeutic benefit in the treatment of a disease, disorder or condition, or to delay or minimize one or more symptoms associated with the disease, disorder or condition. A therapeutically effective amount of a compound means an amount of therapeutic agent, alone or in combination with other therapies, which provides a therapeutic benefit in the treatment of the disease, disorder or condition. The term "therapeutically effective amount" can encompass an amount that improves overall therapy, reduces or avoids symptoms or causes of disease or condition, or enhances the therapeutic efficacy of another therapeutic agent.

As used herein, and unless otherwise specified, a "prophylactically effective amount" of a compound is an amount sufficient to prevent a disease, disorder or condition, or one or more symptoms associated with the disease, disorder or condition, or prevent its recurrence. A prophylactically effective amount of a compound means an amount of a therapeutic agent, alone or in combination with other agents, which provides a prophylactic benefit in the prevention of the disease, disorder or condition. The term "prophylactically effective amount" can encompass an amount that improves overall prophylaxis or enhances the prophylactic efficacy of another prophylactic agent.

DETAILED DESCRIPTION OF CERTAIN EMBODIMENTS OF THE INVENTION

As generally described herein, the present invention provides C17-substituted neuroactive steroids designed, for example, to act as GABA modulators. In certain embodiments, such compounds are envisioned to be useful as therapeutic agents for the inducement of anesthesia and/or sedation in a subject. In certain embodiments, such compounds are envisioned to be useful as therapeutic agents for treating a CNS-related disorder.

Compounds

In one aspect, provided is a compound of the Formula (I):

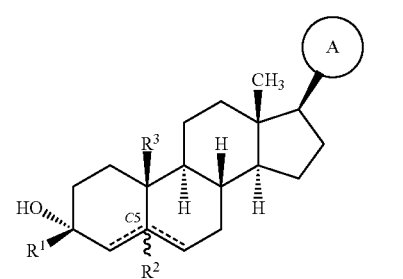

(I)

or a pharmaceutically acceptable salt thereof; wherein: Ring A is aryl or heteroaryl; $R^1$ is hydrogen, $C_{1-3}$ alkyl (e.g., unsubstituted $C_{1-3}$ alkyl (e.g., —$CH_3$, —$CH_2CH_3$) or substituted $C_{1-3}$ alkyl (e.g., $C_{1-3}$ haloalkyl (e.g., —$CHF_2$, —$CH_2F$, —$CF_3$), —$CH_2OCH_3$)), $C_{2-6}$ alkenyl, or $C_{3-6}$ carbocyclyl; $R^2$ is absent or hydrogen; $R^3$ is hydrogen, alkyl, or —$CH_2OR^{3A}$, wherein $R^{3A}$ is hydrogen, $C_{1-6}$ alkyl, $C_{2-6}$ alkenyl, $C_{2-6}$ alkynyl, aryl, heteroaryl, or $C_{3-6}$ carbocyclyl; ═══ represents a single or double bond, wherein when one ═══ is a double bond, the other ═══ is a single bond; wherein when $R^1$ is —$CH_3$, $R^2$ is hydrogen in the alpha configuration, and $R^3$ is —$CH_3$, then A is aryl.

In some embodiments, when $R^3$ is —$CH_3$, $R^2$ is hydrogen in the beta configuration.

In some embodiments, the compound of Formula (I) is a compound of Formula (I-a):

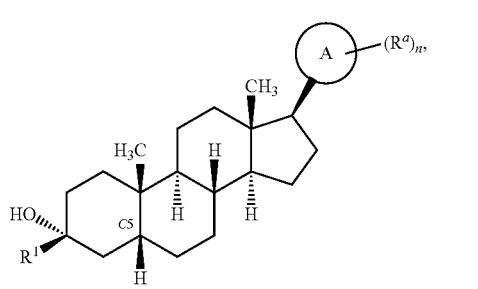

(I-a)

wherein: n is 0, 1, 2, 3, 4, or 5; $R^a$ is halogen, $C_1$-$C_6$ alkyl, $C_2$-$C_6$ alkenyl, $C_2$-$C_6$ alkynyl, carbocyclyl, heterocyclyl, aryl, heteroaryl, —C(O)$R^A$, —C(O)O$R^A$, —C(O)N$R^B R^C$, —S(O)$_2 R^D$, or —O$R^Y$, wherein $R^Y$ is hydrogen, $C_1$-$C_6$ alkyl, $C_2$-$C_6$ alkenyl, $C_2$-$C_6$ alkynyl, carbocyclyl, heterocyclyl, aryl, heteroaryl, —C(O)$R^A$, —C(O)O$R^A$, —C(O)N$R^B R^C$, or —S(O)$_2 R^D$; $R^A$ is hydrogen, $C_1$-$C_6$ alkyl, carbocyclyl, heterocyclyl, aryl, or heteroaryl; each of $R^B$ and $R^C$ is independently hydrogen, $C_1$-$C_6$ alkyl, carbocyclyl, heterocyclyl, aryl, heteroaryl, or taken together with the atom to which they are attached form a ring (e.g., a 3-7-membered ring, e.g., a 5-7-membered ring; a ring containing at least one heteroatom, e.g., a nitrogen, oxygen, or sulfur atom); and $R^D$ is hydrogen, $C_1$-$C_6$ alkyl, carbocyclyl, heterocyclyl, aryl, or heteroaryl.

In some embodiments, A is a 5-7-membered ring. In some embodiments, A is monocyclic or bicyclic. In some embodiments, A is monocyclic. In some embodiments, A is bicyclic. In some embodiments, A contains at least one nitrogen atom. In some embodiments, A contains two nitrogen atoms. In some embodiments, A is a 5-membered ring. In some embodiments, A is oxazole, pyrazole, or thiazole. In some embodiments, A is a 6-membered ring. In some embodiments, A is an aryl ring. In some embodiments, A is phenyl. In some embodiments, A is a heteroaryl ring. In some embodiments, A is pyridine or pyrimidine.

In some embodiments, n is 0 or 1. In some embodiments, n is 0. In some embodiments, n is 1, and $R^a$ is alkyl (e.g., —CH$_2$OH).

In some embodiments, $R^1$ is unsubstituted $C_{1-3}$ alkyl. In some embodiments, $R^1$ is —CH$_3$.

In some embodiments, the compound of Formula (I-a) is selected from:

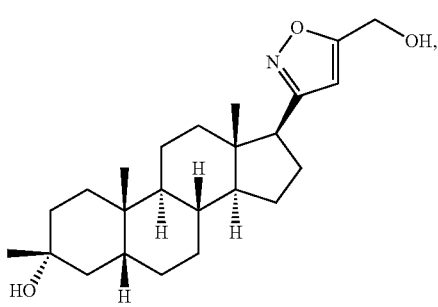

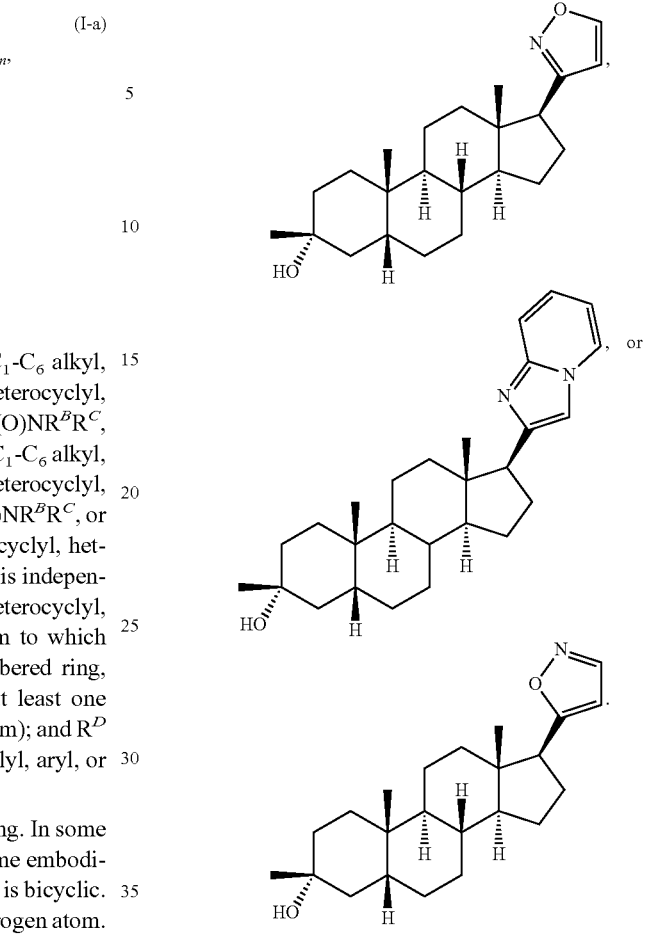

In some embodiments, the compound of Formula (I) is a compound of Formula (I-b):

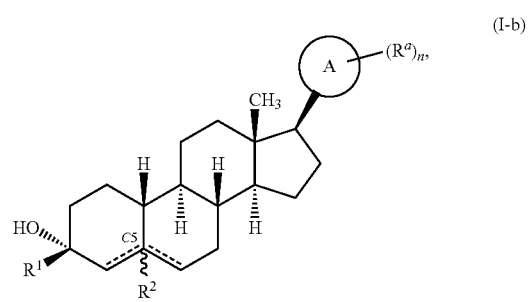

(I-b)

wherein: n is 0, 1, 2, 3, 4, or 5; $R^a$ is halogen, $C_1$-$C_6$ alkyl, $C_2$-$C_6$ alkenyl, $C_2$-$C_6$ alkynyl, carbocyclyl, heterocyclyl, aryl, heteroaryl, —C(O)$R^A$, —C(O)O$R^A$, —C(O)N$R^B R^C$, —S(O)$_2 R^D$, or —O$R^Y$, wherein $R^Y$ is hydrogen, $C_1$-$C_6$ alkyl, $C_2$-$C_6$ alkenyl, $C_2$-$C_6$ alkynyl, carbocyclyl, heterocyclyl, aryl, heteroaryl, —C(O)$R^A$, —C(O)O$R^A$, —C(O)N$R^B R^C$, or —S(O)$_2 R^D$; $R^A$ is hydrogen, $C_1$-$C_6$ alkyl, carbocyclyl, heterocyclyl, aryl, or heteroaryl; each of $R^B$ and $R^C$ is independently hydrogen, $C_1$-$C_6$ alkyl, carbocyclyl, heterocyclyl, aryl, heteroaryl, or taken together with the atom to which they are attached form a ring (e.g., a 3-7-membered ring, e.g., a 5-7-membered ring; a ring containing at least one heteroatom, e.g., a nitrogen, oxygen, or sulfur atom); and $R^D$ is hydrogen, $C_1$-$C_6$ alkyl, carbocyclyl, heterocyclyl, aryl, or heteroaryl.

In some embodiments, the compound of Formula (I-b) is a compound of Formula (I-b-i), (I-b-ii), (I-b-iii), or (I-b-iv):

In some embodiments, n is 1, and $R^a$ is alkyl (e.g., —CH$_2$OH).

In some embodiments, $R^1$ is unsubstituted $C_{1-3}$ alkyl. In some embodiments, $R^1$ is —CH$_3$. In some embodiments, $R^1$ is —CH$_2$CH$_3$. In some embodiments, $R^1$ is substituted $C_{1-3}$ alkyl. In some embodiments, $R^1$ is $C_{1-3}$ haloalkyl. In some embodiments, $R^1$ is —CHF$_2$, —CH$_2$F, or —CF$_3$. In some embodiments, $R^1$ is —CH$_2$OCH$_3$.

In some embodiments, the compound of Formula (I-b) is selected from:

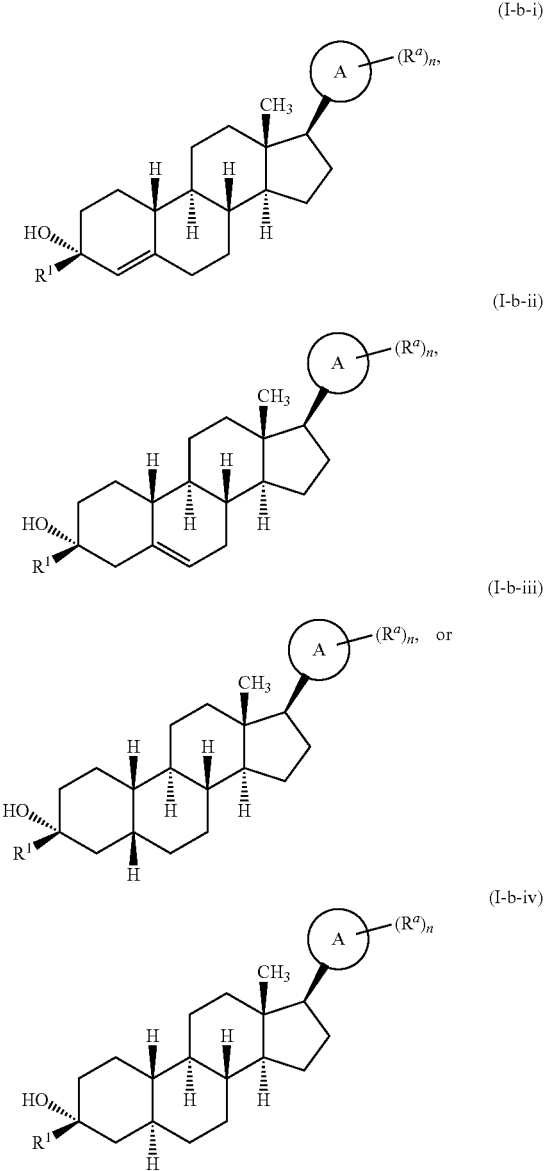

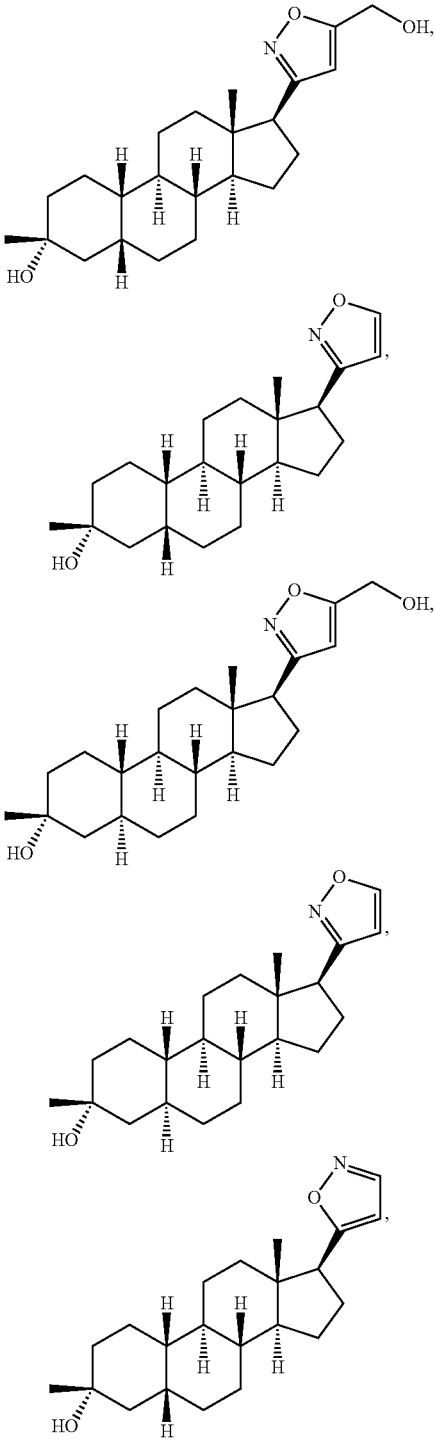

In some embodiments, A is a 5-7-membered ring.

In some embodiments, A is monocyclic or bicyclic. In some embodiments, A is monocyclic. In some embodiments, A is bicyclic. In some embodiments, A contains at least one nitrogen atom. In some embodiments, A contains two nitrogen atoms. In some embodiments, A is a 5-membered ring. In some embodiments, A is oxazole, pyrazole, or thiazole. In some embodiments, A is a 6-membered ring. In some embodiments, A is an aryl ring. In some embodiments, A is phenyl. In some embodiments, A is a heteroaryl ring. In some embodiments, A is pyridine or pyrimidine.

In some embodiments, n is 0 or 1. In some embodiments, n is 0.

-continued

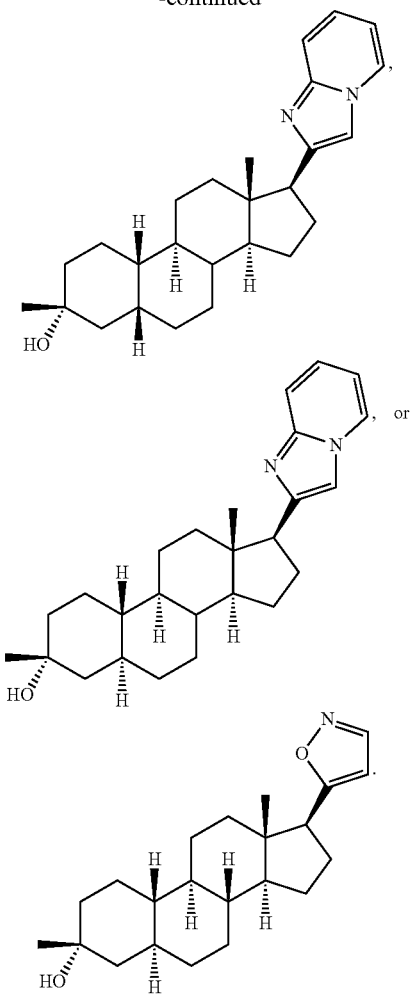

In some embodiments, the compound of Formula (I) is a compound of Formula (I-c):

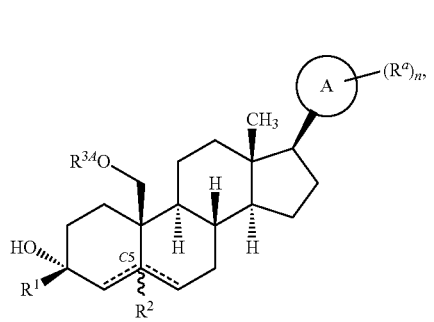

(I-c)

wherein: n is 0, 1, 2, 3, 4, or 5; $R^a$ is halogen, $C_1$-$C_6$ alkyl, $C_2$-$C_6$ alkenyl, $C_2$-$C_6$ alkynyl, carbocyclyl, heterocyclyl, aryl, heteroaryl, —C(O)$R^A$, —C(O)O$R^A$, —C(O)N$R^B R^C$, —S(O)$_2 R^D$, or —O$R^Y$, wherein $R^Y$ is hydrogen, $C_1$-$C_6$ alkyl, $C_2$-$C_6$ alkenyl, $C_2$-$C_6$ alkynyl, carbocyclyl, heterocyclyl, aryl, heteroaryl, —C(O)$R^A$, —C(O)O$R^A$, —C(O)N$R^B R^C$, or —S(O)$_2 R^D$; $R^A$ is hydrogen, $C_1$-$C_6$ alkyl, carbocyclyl, heterocyclyl, aryl, or heteroaryl; each of $R^B$ and $R^C$ is independently hydrogen, $C_1$-$C_6$ alkyl, carbocyclyl, heterocyclyl, aryl, heteroaryl, or taken together with the atom to which they are attached form a ring (e.g., a 3-7-membered ring, e.g., a 5-7-membered ring; a ring containing at least one heteroatom, e.g., a nitrogen, oxygen, or sulfur atom); and $R^D$ is hydrogen, $C_1$-$C_6$ alkyl, carbocyclyl, heterocyclyl, aryl, or heteroaryl.

In some embodiments, the compound of Formula (I-c) is a compound of Formula (I-c-i), (I-c-ii), (I-c-iii), or (I-c-iv):

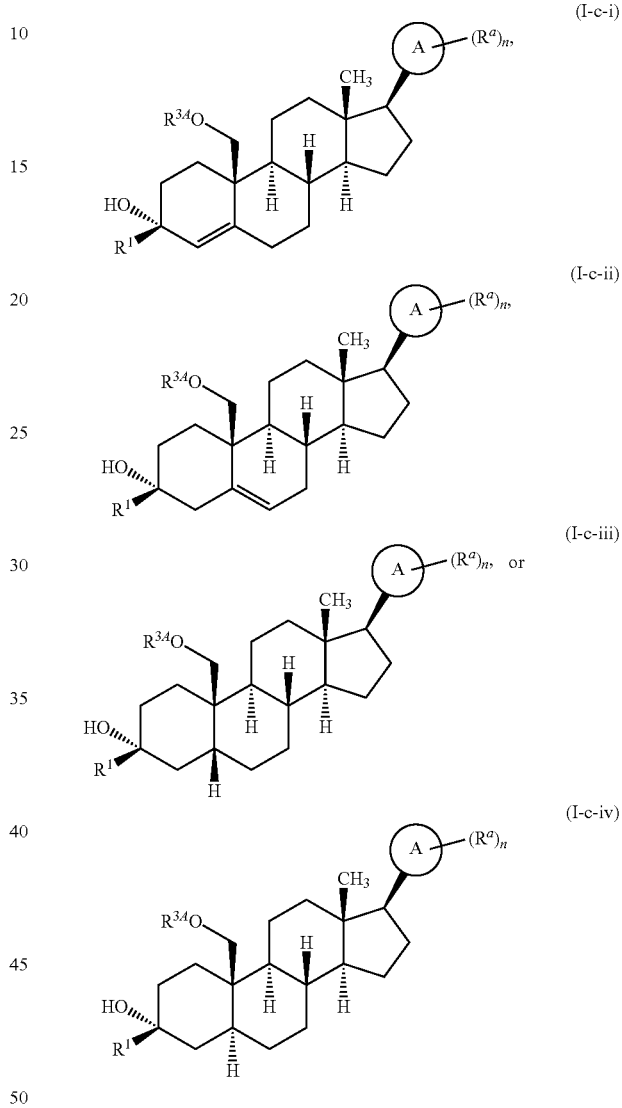

In some embodiments, A is a 5-7-membered ring. In some embodiments, A is monocyclic or bicyclic. In some embodiments, A is monocyclic. In some embodiments, A is bicyclic. In some embodiments, A contains at least one nitrogen atom. In some embodiments, A contains two nitrogen atoms. In some embodiments, A is a 5-membered ring. In some embodiments, A is oxazole, pyrazole, or thiazole. In some embodiments, A is a 6-membered ring. In some embodiments, A is an aryl ring. In some embodiments, A is phenyl. In some embodiments, A is a heteroaryl ring. In some embodiments, A is pyridine or pyrimidine.

In some embodiments, n is 0 or 1. In some embodiments, n is 0. In some embodiments, n is 1, and $R^a$ is alkyl. In some embodiments, $R^a$ is —CH$_3$ or —CH$_2$CH$_3$. In some embodiments, $R^a$ is —CH$_2$OH. In some embodiments, $R^a$ is —CH$_2$—Z; wherein Z is a substituted or unsubstituted 5-12-membered ring. In some embodiments, Z is monocyclic or bicyclic. In some embodiments, Z is a nitrogen-containing heterocyclyl or heteroaryl ring. In some aspects of these embodiments, Z is attached through a nitrogen atom. In some embodiments, Z is a heteroaryl. In some embodiments, Z is pyrazole, triazole, tetrazole, benzopyrazole, benzotriazole. In some embodiments, Z is heterocyclyl. In some embodiments, Z is pyrrolidine, morpholine, piperidine.

In some embodiments, $R^1$ is unsubstituted $C_{1-3}$ alkyl. In some embodiments, $R^1$ is —$CH_3$. In some embodiments, $R^1$ is —$CH_2CH_3$. In some embodiments, $R^1$ is substituted $C_{1-3}$ alkyl. In some embodiments, $R^1$ is $C_{1-3}$ haloalkyl. In some embodiments, $R^1$ is —$CHF_2$, —$CH_2F$, or —$CF_3$. In some embodiments, $R^1$ is —$CH_2OCH_3$.

In some embodiments, the compound of Formula (I-c) is selected from:

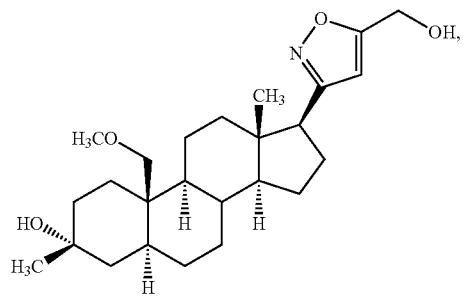

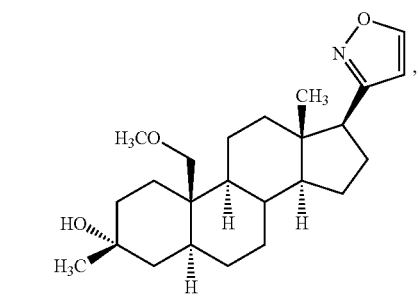

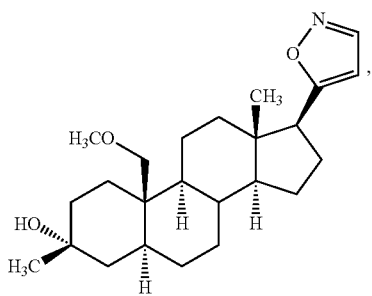

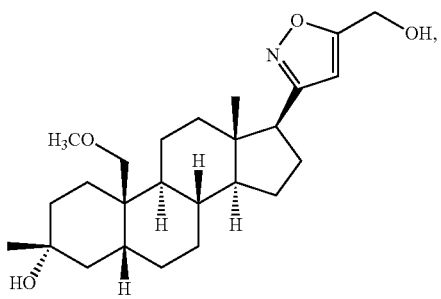

-continued

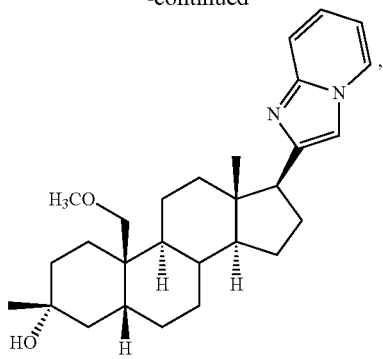

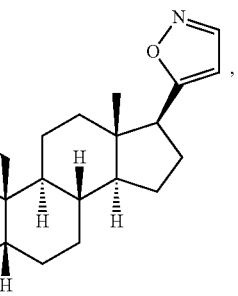

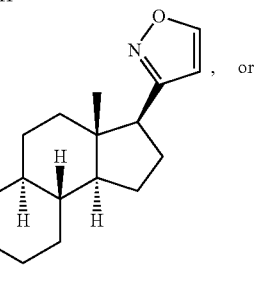

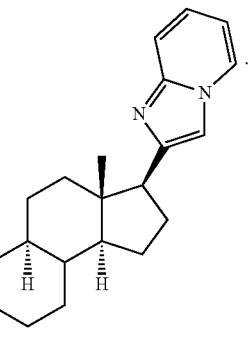

Pharmaceutical Compositions

In one aspect, the invention provides a pharmaceutical composition comprising a compound of the present invention (also referred to as the "active ingredient") and a pharmaceutically acceptable excipient. In certain embodiments, the pharmaceutical composition comprises an effective amount of the active ingredient. In certain embodiments, the pharmaceutical composition comprises a therapeutically effective amount of the active ingredient. In certain embodiments, the pharmaceutical composition comprises a prophylactically effective amount of the active ingredient.

The pharmaceutical compositions provided herein can be administered by a variety of routes including, but not limited to, oral (enteral) administration, parenteral (by injection) administration, rectal administration, transdermal administration, intradermal administration, intrathecal administration, subcutaneous (SC) administration, intravenous (IV) administration, intramuscular (IM) administration, and intranasal administration.

Generally, the compounds provided herein are administered in an effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

When used to prevent the onset of a CNS-disorder, the compounds provided herein will be administered to a subject at risk for developing the condition, typically on the advice and under the supervision of a physician, at the dosage levels described above. Subjects at risk for developing a particular condition generally include those that have a family history of the condition, or those who have been identified by genetic testing or screening to be particularly susceptible to developing the condition.

The pharmaceutical compositions provided herein can also be administered chronically ("chronic administration"). Chronic administration refers to administration of a compound or pharmaceutical composition thereof over an extended period of time, e.g., for example, over 3 months, 6 months, 1 year, 2 years, 3 years, 5 years, etc, or may be continued indefinitely, for example, for the rest of the subject's life. In certain embodiments, the chronic administration is intended to provide a constant level of the compound in the blood, e.g., within the therapeutic window over the extended period of time.

The pharmaceutical compostions of the present invention may be further delivered using a variety of dosing methods. For example, in certain embodiments, the pharmaceutical composition may be given as a bolus, e.g., in order to raise the concentration of the compound in the blood to an effective level. The placement of the bolus dose depends on the systemic levels of the active ingredient desired throughout the body, e.g., an intramuscular or subcutaneous bolus dose allows a slow release of the active ingredient, while a bolus delivered directly to the veins (e.g., through an IV drip) allows a much faster delivery which quickly raises the concentration of the active ingredient in the blood to an effective level. In other embodiments, the pharmaceutical composition may be administered as a continuous infusion, e.g., by IV drip, to provide maintenance of a steady-state concentration of the active ingredient in the subject's body. Furthermore, in still yet other embodiments, the pharmaceutical composition may be administered as first as a bolus dose, followed by continuous infusion.

The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules or the like in the case of solid compositions. In such compositions, the compound is usually a minor component (from about 0.1 to about 50% by weight or preferably from about 1 to about 40% by weight) with the remainder being various vehicles or excipients and processing aids helpful for forming the desired dosing form.

With oral dosing, one to five and especially two to four and typically three oral doses per day are representative regimens. Using these dosing patterns, each dose provides from about 0.01 to about 20 mg/kg of the compound provided herein, with preferred doses each providing from about 0.1 to about 10 mg/kg, and especially about 1 to about 5 mg/kg.

Transdermal doses are generally selected to provide similar or lower blood levels than are achieved using injection doses, generally in an amount ranging from about 0.01 to about 20% by weight, preferably from about 0.1 to about 20% by weight, preferably from about 0.1 to about 10% by weight, and more preferably from about 0.5 to about 15% by weight.

Injection dose levels range from about 0.1 mg/kg/hour to at least 20 mg/kg/hour, all for from about 1 to about 120 hours and especially 24 to 96 hours. A preloading bolus of from about 0.1 mg/kg to about 10 mg/kg or more may also be administered to achieve adequate steady state levels. The maximum total dose is not expected to exceed about 5 g/day for a 40 to 80 kg human patient.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable excipients known in the art. As before, the active compound in such compositions is typically a minor component, often being from about 0.05 to 10% by weight with the remainder being the injectable excipient and the like.

Transdermal compositions are typically formulated as a topical ointment or cream containing the active ingredient(s). When formulated as a ointment, the active ingredients will typically be combined with either a paraffinic or a water-miscible ointment base. Alternatively, the active ingredients may be formulated in a cream with, for example an oil-in-water cream base. Such transdermal formulations are well-known in the art and generally include additional ingredients to enhance the dermal penetration of stability of the active ingredients or Formulation. All such known transdermal formulations and ingredients are included within the scope provided herein.

The compounds provided herein can also be administered by a transdermal device.

Accordingly, transdermal administration can be accomplished using a patch either of the reservoir or porous membrane type, or of a solid matrix variety.

The above-described components for orally administrable, injectable or topically administrable compositions are merely representative. Other materials as well as processing techniques and the like are set forth in Part 8 of *Remington's Pharmaceutical Sciences,* 17th edition, 1985, Mack Publishing Company, Easton, Pa., which is incorporated herein by reference.

The compounds of the present invention can also be administered in sustained release forms or from sustained release drug delivery systems. A description of representative sustained release materials can be found in *Remington's Pharmaceutical Sciences*.

The present invention also relates to the pharmaceutically acceptable acid addition salt of a compound of the present invention. The acid which may be used to prepare the pharmaceutically acceptable salt is that which forms a non-toxic acid addition salt, i.e., a salt containing pharmacologically acceptable anions such as the hydrochloride, hydroiodide, hydrobromide, nitrate, sulfate, bisulfate, phosphate, acetate, lactate, citrate, tartrate, succinate, maleate, fumarate, benzoate, para-toluenesulfonate, and the like.

In another aspect, the invention provides a pharmaceutical composition comprising a compound of the present invention and a pharmaceutically acceptable excipient, e.g., a composition suitable for injection, such as for intravenous (IV) administration.

Pharmaceutically acceptable excipients include any and all diluents or other liquid vehicles, dispersion or suspension aids, surface active agents, isotonic agents, preservatives, lubricants and the like, as suited to the particular dosage form desired, e.g., injection. General considerations in the formulation and/or manufacture of pharmaceutical compositions agents can be found, for example, in *Remington's Pharmaceutical Sciences*, Sixteenth Edition, E. W. Martin (Mack Publishing Co., Easton, Pa., 1980), and *Remington: The Science and Practice of Pharmacy*, 21$^{st}$ Edition (Lippincott Williams & Wilkins, 2005).

For example, injectable preparations, such as sterile injectable aqueous suspensions, can be formulated according to the known art using suitable dispersing or wetting agents and suspending agents. Exemplary excipients that can be employed include, but are not limited to, water, sterile saline or phosphate-buffered saline, or Ringer's solution.

In certain embodiments, the pharmaceutical composition further comprises a cyclodextrin derivative. The most common cyclodextrins are α-, β- and γ- cyclodextrins consisting of 6, 7 and 8 α- 1,4- linked glucose units, respectively, optionally comprising one or more substituents on the linked sugar moieties, which include, but are not limited to, substituted or unsubstituted methylated, hydroxyalkylated, acylated, and sulfoalkylether substitution. In certain embodiments, the cyclodextrin is a sulfoalkyl ether β-cyclodextrin, e.g., for example, sulfobutyl ether β-cyclodextrin, also known as CAPTISOL®. See, e.g., U.S. 5,376,645. In certain embodiments, the composition comprises hexapropyl- β-cyclodextrin. In a more particular embodiment, the composition comprises hexapropyl- β-cyclodextrin (10-50% in water).

The injectable composition can be sterilized, for example, by filtration through a bacterial-retaining filter, or by incorporating sterilizing agents in the form of sterile solid compositions which can be dissolved or dispersed in sterile water or other sterile injectable medium prior to use.

Generally, the compounds provided herein are administered in an effective amount. The amount of the compound actually administered will typically be determined by a physician, in the light of the relevant circumstances, including the condition to be treated, the chosen route of administration, the actual compound administered, the age, weight, response of the individual patient, the severity of the patient's symptoms, and the like.

The compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include pre-filled, pre-measured ampules or syringes of the liquid compositions. In such compositions, the compound is usually a minor component (from about 0.1% to about 50% by weight or preferably from about 1% to about 40% by weight) with the remainder being various vehicles or carriers and processing aids helpful for forming the desired dosing form.

The compounds provided herein can be administered as the sole active agent, or they can be administered in combination with other active agents. In one aspect, the present invention provides a combination of a compound of the present invention and another pharmacologically active agent. Administration in combination can proceed by any technique apparent to those of skill in the art including, for example, separate, sequential, concurrent, and alternating administration.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation. General considerations in the formulation and/or manufacture of pharmaceutical compositions can be found, for example, in *Remington: The Science and Practice of Pharmacy* 21$^{st}$ ed., Lippincott Williams & Wilkins, 2005.

Methods of Use and Treatment

As generally described herein, the present invention is directed to C17-substituted neuroactive steroids designed, for example, to act as GABA modulators. In certain embodiments, such compounds are envisioned to be useful as therapeutic agents for the inducement of anesthesia and/or sedation in a subject. In some embodiments, such compounds are envisioned to be useful as therapeutic agents for treating a CNS-related disorder (e.g., sleep disorder, a mood disorder (e.g., depression, for example severe depression or postpartum depression; or anxiety disorders), a schizophrenia spectrum disorder, a convulsive disorder, a disorder of memory and/or cognition, a movement disorder (e.g., tremor, for example essential tremor), a personality disorder, autism spectrum disorder, pain, traumatic brain injury, a vascular disease, a substance abuse disorder and/or withdrawal syndrome, or tinnitus) in a subject in need (e.g., a subject with Rett syndrome, Fragile X syndrome, or Angelman syndrome).

Thus, in one aspect, the present invention provides a method of inducing sedation and/or anesthesia in a subject, comprising administering to the subject an effective amount of a compound of the present invention or a composition thereof. In certain embodiments, the compound is administered by intravenous administration.

Earlier studies (see, e.g., Gee et al., *European Journal of Pharmacology*, 136:419-423 (1987)) demonstrated that certain 3α-hydroxylated steroids are orders of magnitude more potent as modulators of the GABA receptor complex (GRC) than others had reported (see, e.g., Majewska et al., Science 232:1004-1007 (1986); Harrison et al., *J Pharmacol. Exp. Ther.* 241:346-353 (1987)). Majewska et al. and Harrison et al. taught that 3α-hydroxylated-5-reduced steroids are only capable of much lower levels of effectiveness. In vitro and in vivo experimental data have now demonstrated that the high potency of these steroids allows them to be therapeutically useful in the modulation of brain excitability via the GRC (see, e.g., Gee et al., *European Journal of Pharmacology*, 136:419-423 (1987); Wieland et al., *Psychopharmacology* 118(1):65-71 (1995)).

Various synthetic steroids have also been prepared as neuroactive steroids. See, for example, U.S. Pat. No. 5,232,917, which discloses neuroactive steroid compounds useful in treating stress, anxiety, insomnia, seizure disorders, and mood disorders, that are amenable to GRC-active agents, such as depression, in a therapeutically beneficial manner. Furthermore, it has been previously demonstrated that these steroids interact at a unique site on the GRC which is distinct from other known sites of interaction (e.g., barbiturates, benzodiazepines, and GABA) where therapeutically beneficial effects on stress, anxiety, sleep, mood disorders and seizure disorders have been previously elicited (see, e.g., Gee, K. W. and Yamamura, H. I., "Benzodiazepines and Barbiturates: Drugs for the Treatment of Anxiety, Insomnia and Seizure Disorders," in *Central Nervous System Disorders*, Horvell, ed., Marcel-Dekker, New York (1985), pp. 123-147; Lloyd, K. G. and Morselli, P. L., "Psychopharmacology of GABAergic Drugs," in *Psychopharmacology: The Third Generation of Progress*, H. Y. Meltzer, ed., Raven Press, N.Y. (1987), pp. 183-195; and Gee et al., *European Journal of Pharmacology*, 136:419-423 (1987). These compounds are desirable for their duration, potency, and oral activity (along with other forms of administration).

Compounds of the present invention, as described herein, are generally designed to modulate GABA function, and therefore to act as neuroactive steroids for the treatment and prevention of CNS-related conditions in a subject. Modulation, as used herein, refers to the inhibition or potentiation of GABA receptor function. Accordingly, the compounds and pharmaceutical compositions provided herein find use as therapeutics for preventing and/or treating CNS conditions in mammals including humans and non-human mammals. Thus, and as stated earlier, the present invention includes within its scope, and extends to, the recited methods of treatment, as well as to the compounds for such methods, and to the use of such compounds for the preparation of medicaments useful for such methods.

Exemplary CNS conditions related to GABA-modulation include, but are not limited to, sleep disorders [e.g., insomnia], mood disorders [e.g., depression, dysthymic disorder (e.g., mild depression), bipolar disorder (e.g., I and/or II), anxiety disorders (e.g., generalized anxiety disorder (GAD), social anxiety disorder), stress, post-traumatic stress disorder (PTSD), compulsive disorders (e.g., obsessive compulsive disorder (OCD))], schizophrenia spectrum disorders [e.g., schizophrenia, schizoaffective disorder], convulsive disorders [e.g., epilepsy (e.g., status epilepticus (SE)), seizures], disorders of memory and/or cognition [e.g., attention disorders (e.g., attention deficit hyperactivity disorder (ADHD)), dementia (e.g., Alzheimer's type dementia, Lewis body type dementia, vascular type dementia], movement disorders [e.g., Huntington's disease, Parkinson's disease, tremor (e.g., essential tremor)], personality disorders [e.g., anti-social personality disorder, obsessive compulsive personality disorder], autism spectrum disorders (ASD) [e.g., autism, monogenetic causes of autism such as synaptophathy's, e.g., Rett syndrome, Fragile X syndrome, Angelman syndrome], pain [e.g., neuropathic pain, injury related pain syndromes, acute pain, chronic pain], traumatic brain injury (TBI), vascular diseases [e.g., stroke, ischemia, vascular malformations], substance abuse disorders and/or withdrawal syndromes [e.g., addition to opiates, cocaine, and/or alcohol], and tinnitus.

In yet another aspect, provided is a combination of a compound of the present invention and another pharmacologically active agent. The compounds provided herein can be administered as the sole active agent or they can be administered in combination with other agents. Administration in combination can proceed by any technique apparent to those of skill in the art including, for example, separate, sequential, concurrent and alternating administration.

In another aspect, provided is a method of treating or preventing brain excitability in a subject susceptible to or afflicted with a condition associated with brain excitability, comprising administering to the subject an effective amount of a compound of the present invention to the subject.

In yet another aspect, provided is a method of treating or preventing stress or anxiety in a subject, comprising administering to the subject in need of such treatment an effective amount of a compound of the present invention, or a composition thereof.

In yet another aspect, provided is a method of alleviating or preventing movement disorder (e.g., tremor, for example essential tremor) in a subject, comprising administering to the subject in need of such treatment an effective amount of a compound of the present invention. In certain embodiments the movement disorder is tremor. In certain embodiments the tremor is essential tremor.

In yet another aspect, provided is a method of alleviating or preventing seizure activity in a subject, comprising administering to the subject in need of such treatment an effective amount of a compound of the present invention.

In yet another aspect, provided is a method of alleviating or preventing insomnia in a subject, comprising administering to the subject in need of such treatment an effective amount of a compound of the present invention, or a composition thereof.

In yet another aspect, provided is a method of inducing sleep and maintaining substantially the level of REM sleep that is found in normal sleep, wherein substantial rebound insomnia is not induced, comprising administering an effective amount of a compound of the present invention.

In yet another aspect, provided is a method of alleviating or preventing PMS or PND in a subject, comprising administering to the subject in need of such treatment an effective amount of a compound of the present invention.

In yet another aspect, provided is a method of treating or preventing mood disorders in a subject, comprising administering to the subject in need of such treatment an effective amount of a compound of the present invention. In certain embodiments the mood disorder is an anxiety disorder. In certain embodiments the mood disorder is depression. In certain embodiments the depression is severe depression. In certain embodiment the depression is post-partum depression.

In yet another aspect, provided is a method of inducing anesthesia in a subject, comprising administering to the subject an effective amount of a compound of the present invention.

In yet another aspect, provided is a method of cognition enhancement or treating memory disorder by administering to the subject a therapeutically effective amount of a compound of the present invention. In certain embodiments, the disorder is Alzheimer's disease. In certain embodiments, the disorder is Rett syndrome.

In yet another aspect, provided is a method of treating attention disorders by administering to the subject a therapeutically effective amount of a compound of the present invention. In certain embodiments, the attention disorder is ADHD.

In certain embodiments, the compound is administered to the subject chronically. In certain embodiments, the compound is administered to the subject orally, subcutaneously, intramuscularly, or intravenously.

Anesthesia/Sedation

Anesthesia is a pharmacologically induced and reversible state of amnesia, analgesia, loss of responsiveness, loss of skeletal muscle reflexes, decreased stress response, or all of these simultaneously. These effects can be obtained from a single drug which alone provides the correct combination of effects, or occasionally with a combination of drugs (e.g., hypnotics, sedatives, paralytics, analgesics) to achieve very specific combinations of results. Anesthesia allows patients to undergo surgery and other procedures without the distress and pain they would otherwise experience.

Sedation is the reduction of irritability or agitation by administration of a pharmacological agent, generally to facilitate a medical procedure or diagnostic procedure.

Sedation and analgesia include a continuum of states of consciousness ranging from minimal sedation (anxiolysis) to general anesthesia.

Minimal sedation is also known as anxiolysis. Minimal sedation is a drug-induced state during which the patient responds normally to verbal commands. Cognitive function and coordination may be impaired. Ventilatory and cardiovascular functions are typically unaffected.

Moderate sedation/analgesia (conscious sedation) is a drug-induced depression of consciousness during which the patient responds purposefully to verbal command, either alone or accompanied by light tactile stimulation. No interventions are usually necessary to maintain a patent airway. Spontaneous ventilation is typically adequate. Cardiovascular function is usually maintained.

Deep sedation/analgesia is a drug-induced depression of consciousness during which the patient cannot be easily aroused, but responds purposefully (not a reflex withdrawal from a painful stimulus) following repeated or painful stimulation. Independent ventilatory function may be impaired and the patient may require assistance to maintain a patent airway. Spontaneous ventilation may be inadequate. Cardiovascular function is usually maintained.

General anesthesia is a drug-induced loss of consciousness during which the patient is not arousable, even to painful stimuli. The ability to maintain independent ventilatory function is often impaired and assistance is often required to maintain a patent airway. Positive pressure ventilation may be required due to depressed spontaneous ventilation or drug-induced depression of neuromuscular function. Cardiovascular function may be impaired.

Sedation in the intensive care unit (ICU) allows the depression of patients' awareness of the environment and reduction of their response to external stimulation. It can play a role in the care of the critically ill patient, and encompasses a wide spectrum of symptom control that will vary between patients, and among individuals throughout the course of their illnesses. Heavy sedation in critical care has been used to facilitate endotracheal tube tolerance and ventilator synchronization, often with neuromuscular blocking agents.

In some embodiments, sedation (e.g., long-term sedation, continuous sedation) is induced and maintained in the ICU for a prolonged period of time (e.g., 1 day, 2 days, 3 days, 5 days, 1 week, 2 week, 3 weeks, 1 month, 2 months). Long-term sedation agents may have long duration of action. Sedation agents in the ICU may have short elimination half-life.

Procedural sedation and analgesia, also referred to as conscious sedation, is a technique of administering sedatives or dissociative agents with or without analgesics to induce a state that allows a subject to tolerate unpleasant procedures while maintaining cardiorespiratory function.

Neuroendocrine Disorders and Dysfunction

Provided herein are methods that can be used for treating neuroendocrine disorders and dysfunction. As used herein, "neuroendocrine disorder" or "neuroendocrine dysfunction" refers to a variety of conditions caused by imbalances in the body's hormone production directly related to the brain. Neuroendocrine disorders involve interactions between the nervous system and the endocrine system. Because the hypothalamus and the pituitary gland are two areas of the brain that regulate the production of hormones, damage to the hypothalamus or pituitary gland, e.g., by traumatic brain injury, may impact the production of hormones and other neuroendocrine functions of the brain.

Symptoms of neuroendocrine disorder include, but are not limited to, behavioral, emotional, and sleep-related symptoms, symptoms related to reproductive function, and somatic symptoms; including but not limited to fatigue, poor memory, anxiety, depression, weight gain or loss, emotional lability, lack of concentration, attention difficulties, loss of lipido, infertility, amenorrhea, loss of muscle mass, increased belly body fat, low blood pressure, reduced heart rate, hair loss, anemia, constipation, cold intolerance, and dry skin.

Neurodegenerative Diseases and Disorders

Provided herein are methods that can be used for treating neurodegenerative diseases and disorders. The term "neurodegenerative disease" includes diseases and disorders that are associated with the progressive loss of structure or function of neurons, or death of neurons. Neurodegenerative diseases and disorders include, but are not limited to, Alzheimer's disease (including the associated symptoms of mild, moderate, or severe cognitive impairment); amyotrophic lateral sclerosis (ALS); anoxic and ischemic injuries; ataxia and convulsion (including for the treatment and prevention and prevention of seizures that are caused by schizoaffective disorder or by drugs used to treat schizophrenia); benign forgetfulness; brain edema; cerebellar ataxia including McLeod neuroacanthocytosis syndrome (MLS); closed head injury; coma; contusive injuries (e.g., spinal cord injury and head injury); dementias including multi-infarct dementia and senile dementia; disturbances of consciousness; Down syndrome; drug-induced or medication-induced Parkinsonism (such as neuroleptic-induced acute akathisia, acute dystonia, Parkinsonism, or tardive dyskinesia, neuroleptic malignant syndrome, or medication-induced postural tremor); epilepsy; fragile X syndrome; Gilles de la Tourette's syndrome; head trauma; hearing impairment and loss; Huntington's disease; Lennox syndrome; levodopa-induced dyskinesia; mental retardation; movement disorders including akinesias and akinetic (rigid) syndromes (including basal ganglia calcification, corticobasal degeneration, multiple system atrophy, Parkinsonism-ALS dementia complex, Parkinson's disease, postencephalitic parkinsonism, and progressively supranuclear palsy); muscular spasms and disorders associated with muscular spasticity or weakness including chorea (such as benign hereditary chorea, drug-induced chorea, hemiballism, Huntington's disease, neuroacanthocytosis, Sydenham's chorea, and symptomatic chorea), dyskinesia (including tics such as complex tics, simple tics, and symptomatic tics), myoclonus (including generalized myoclonus and focal cyloclonus), tremor (such as rest tremor, postural tremor, essential tremor and intention tremor) and dystonia (including axial dystonia, dystonic writer's cramp, hemiplegic dystonia, paroxysmal dystonia, and focal dystonia such as blepharospasm, oromandibular dystonia, and spasmodic dysphonia and torticollis); neuronal damage including ocular damage, retinopathy or macular degeneration of the eye; neurotoxic injury which follows cerebral stroke, thromboembolic stroke, hemorrhagic stroke, cerebral ischemia, cerebral vasospasm, hypoglycemia, amnesia, hypoxia, anoxia, perinatal asphyxia and cardiac arrest; Parkinson's disease; seizure; status epilecticus; stroke; tinnitus; tubular sclerosis, and viral infection induced neurodegeneration (e.g., caused by acquired immunodeficiency syndrome (AIDS) and encephalopathies). Neurodegenerative diseases also include, but are not limited to, neurotoxic injury which follows cerebral stroke, thromboembolic stroke, hemorrhagic stroke, cerebral ischemia, cerebral vasospasm, hypoglycemia, amnesia, hypoxia, anoxia, perinatal asphyxia and cardiac arrest. Methods of treating or preventing a neurodegenerative disease also include treating or preventing loss of neuronal function characteristic of neurodegenerative disorder.

Epilepsy

Epilepsy is a brain disorder characterized by repeated seizures over time. Types of epilepsy can include, but are not limited to generalized epilepsy, e.g., childhood absence epilepsy, juvenile nyoclonic epilepsy, epilepsy with grand-mal seizures on awakening, West syndrome, Lennox-Gastaut syndrome, partial epilepsy, e.g., temporal lobe epilepsy, frontal lobe epilepsy, benign focal epilepsy of childhood.

Status epilepticus (SE)

Status epilepticus (SE) can include, e.g., convulsive status epilepticus, e.g., early status epilepticus, established status epilepticus, refractory status epilepticus, super-refractory status epilepticus; non-convulsive status epilepticus, e.g., generalized status epilepticus, complex partial status epilepticus; generalized periodic epileptiform discharges; and periodic lateralized epileptiform discharges. Convulsive status epilepticus is characterized by the presence of convulsive status epileptic seizures, and can include early status epilepticus, established status epilepticus, refractory status epilepticus, super-refractory status epilepticus. Early status epilepticus is treated with a first line therapy. Established status epilepticus is characterized by status epileptic seizures which persist despite treatment with a first line therapy, and a second line therapy is administered. Refractory status epilepticus is characterized by status epileptic seizures which persist despite treatment with a first line and a second line therapy, and a general anesthetic is generally administered. Super refractory status epilepticus is characterized by status epileptic seizures which persist despite treatment with a first line therapy, a second line therapy, and a general anesthetic for 24 hours or more.

Non-convulsive status epilepticus can include, e.g., focal non-convulsive status epilepticus, e.g., complex partial non-convulsive status epilepticus, simple partial non-convulsive status epilepticus, subtle non-convulsive status epilepticus; generalized non-convulsive status epilepticus, e.g., late onset absence non-convulsive status epilepticus, atypical absence non-convulsive status epilepticus, or typical absence non-convulsive status epilepticus.

Compositions described herein can also be administered as a prophylactic to a subject having a CNS disorder e.g., a traumatic brain injury, status epilepticus, e.g., convulsive status epilepticus, e.g., early status epilepticus, established status epilepticus, refractory status epilepticus, super-refractory status epilepticus; non-convulsive status epilepticus, e.g., generalized status epilepticus, complex partial status epilepticus; generalized periodic epileptiform discharges; and periodic lateralized epileptiform discharges; prior to the onset of a seizure.

Seizure

A seizure is the physical findings or changes in behavior that occur after an episode of abnormal electrical activity in the brain. The term "seizure" is often used interchangeably with "convulsion." Convulsions are when a person's body shakes rapidly and uncontrollably. During convulsions, the person's muscles contract and relax repeatedly.

Based on the type of behavior and brain activity, seizures are divided into two broad categories: generalized and partial (also called local or focal). Classifying the type of seizure helps doctors diagnose whether or not a patient has epilepsy.

Generalized seizures are produced by electrical impulses from throughout the entire brain, whereas partial seizures are produced (at least initially) by electrical impulses in a relatively small part of the brain. The part of the brain generating the seizures is sometimes called the focus.

There are six types of generalized seizures. The most common and dramatic, and therefore the most well known, is the generalized convulsion, also called the grand-mal seizure. In this type of seizure, the patient loses consciousness and usually collapses. The loss of consciousness is followed by generalized body stiffening (called the "tonic" phase of the seizure) for 30 to 60 seconds, then by violent jerking (the "clonic" phase) for 30 to 60 seconds, after which the patient goes into a deep sleep (the "postictal" or after-seizure phase). During grand-mal seizures, injuries and accidents may occur, such as tongue biting and urinary incontinence.

Absence seizures cause a short loss of consciousness (just a few seconds) with few or no symptoms. The patient, most often a child, typically interrupts an activity and stares blankly. These seizures begin and end abruptly and may occur several times a day. Patients are usually not aware that they are having a seizure, except that they may be aware of "losing time."

Myoclonic seizures consist of sporadic jerks, usually on both sides of the body. Patients sometimes describe the jerks as brief electrical shocks. When violent, these seizures may result in dropping or involuntarily throwing objects.

Clonic seizures are repetitive, rhythmic jerks that involve both sides of the body at the same time.

Tonic seizures are characterized by stiffening of the muscles.

Atonic seizures consist of a sudden and general loss of muscle tone, particularly in the arms and legs, which often results in a fall.

Seizures described herein can include epileptic seizures; acute repetitive seizures; cluster seizures; continuous seizures; unremitting seizures; prolonged seizures; recurrent seizures; status epilepticus seizures, e.g., refractory convulsive status epilepticus, non-convulsive status epilepticus seizures; refractory seizures; myoclonic seizures; tonic seizures; tonic-clonic seizures; simple partial seizures; complex partial seizures; secondarily generalized seizures; atypical absence seizures; absence seizures; atonic seizures; benign Rolandic seizures; febrile seizures; emotional seizures; focal seizures; gelastic seizures; generalized onset seizures; infantile spasms; Jacksonian seizures; massive bilateral myoclonus seizures; multifocal seizures; neonatal onset seizures; nocturnal seizures; occipital lobe seizures; post traumatic seizures; subtle seizures; Sylvan seizures; visual reflex seizures; or withdrawal seizures.

Movement Disorders

Also described herein are methods for treating a movement disorder. As used herein, "movement disorders" refers to a variety of diseases and disorders that are associated with hyperkinetic movement disorders and related abnormalities in muscle control. Exemplary movement disorders include, but are not limited to, Parkinson's disease and parkinsonism (defined particularly by bradykinesia), dystonia, chorea and Huntington's disease, ataxia, tremor (e.g., essential tremor), myoclonus and startle, tics and Tourette syndrome, Restless legs syndrome, stiff person syndrome, and gait disorders.

Tremor

The methods described herein can be used to treat tremor, for example cerebellar tremor or intention tremor, dystonic tremor, essential tremor, orthostatic tremor, parkinsonian tremor, physiological tremor, psychogenic tremor, or rubral tremor. Tremor includes hereditary, degenerative, and idiopathic disorders such as Wilson's disease, Parkinson's disease, and essential tremor, respectively; metabolic diseases (e.g., thyoid-parathyroid-, liver disease and hypoglycemia); peripheral neuropathies (associated with Charcot-Marie-Tooth, Roussy-Levy, diabetes mellitus, complex regional pain syndrome); toxins (nicotine, mercury, lead, CO, Manganese, arsenic, toluene); drug-induced (narcoleptics, tricyclics, lithium, cocaine, alcohol, adrenaline, bronchodilators, theophylline, caffeine, steroids, valproate, amiodarone, thyroid hormones, vincristine); and psychogenic disorders. Clinical tremor can be classified into physiologic tremor, enhanced physiologic tremor, essential tremor syndromes (including classical essential tremor, primary orthostatic tremor, and task- and position-specific tremor), dystonic tremor, parkinsonian tremor, cerebellar tremor, Holmes' tremor (i.e., rubral tremor), palatal tremor, neuropathic tremor, toxic or drug-induced tremor, and psychogenic tremor.

Tremor is an involuntary, at times rhythmic, muscle contraction and relaxation that can involve oscillations or twitching of one or more body parts (e.g., hands, arms, eyes, face, head, vocal folds, trunk, legs).

Cerebellar tremor or intention tremor is a slow, broad tremor of the extremities that occurs after a purposeful movement. Cerebellar tremor is caused by lesions in or damage to the cerebellum resulting from, e.g., tumor, stroke, disease (e.g., multiple sclerosis, an inherited degenerative disorder).

Dystonic tremor occurs in individuals affected by dystonia, a movement disorder in which sustained involuntary muscle contractions cause twisting and repetitive motions and/or painful and abnormal postures or positions. Dystonic tremor may affect any muscle in the body. Dystonic tremors occurs irregularly and often can be relieved by complete rest.

Essential tremor or benign essential tremor is the most common type of tremor. Essential tremor may be mild and nonprogressive in some, and may be slowly progressive, starting on one side of the body but affect both sides within 3 years. The hands are most often affected, but the head, voice, tongue, legs, and trunk may also be involved. Tremor frequency may decrease as the person ages, but severity may increase. Heightened emotion, stress, fever, physical exhaustion, or low blood sugar may trigger tremors and/or increase their severity. Symptoms generally evolve over time and can be both visible and persistent following onset.

Orthostatic tremor is characterized by fast (e.g., greater than 12 Hz) rhythmic muscle contractions that occurs in the legs and trunk immediately after standing. Cramps are felt in the thighs and legs and the patient may shake uncontrollably when asked to stand in one spot. Orthostatic tremor may occurs in patients with essential tremor.

Parkinsonian tremor is caused by damage to structures within the brain that control movement. Parkinsonian tremor is often a precursor to Parkinson's disease and is typically seen as a "pill-rolling" action of the hands that may also affect the chin, lips, legs, and trunk. Onset of parkinsonian tremor typically begins after age 60. Movement starts in one limb or on one side of the body and can progress to include the other side.

Physiological tremor can occur in normal individuals and have no clinical significance. It can be seen in all voluntary muscle groups. Physiological tremor can be caused by certain drugs, alcohol withdrawal, or medical conditions including an overactive thyroid and hypoglycemia. The tremor classically has a frequency of about 10 Hz.

Psychogenic tremor or hysterical tremor can occur at rest or during postural or kinetic movement. Patient with psychogenic tremor may have a conversion disorder or another psychiatric disease.

Rubral tremor is characterized by coarse slow tremor which can be present at rest, at posture, and with intention. The tremor is associated with conditions that affect the red nucleus in the midbrain, classical unusual strokes.

Parkinson's Disease affects nerve cells in the brain that produce dopamine. Symptoms include muscle rigidity, tremors, and changes in speech and gait. Parkinsonism is characterized by tremor, bradykinesia, rigidity, and postural instability. Parkinsonism shares symptoms found in Parkinson's Disease, but is a symptom complex rather than a progressive neurodegenerative disease.

Dystonia is a movement disorder characterized by sustained or intermittent muscle contractions causing abnormal, often repetitive movements or postures. Dystonic movements can be patterned, twisting, and may be tremulous. Dystonia is often initiated or worsened by voluntary action and associated with overflow muscle activation.

Chorea is a neurological disorder characterized by jerky involuntary movements typically affecting the shoulders, hips, and face. Huntington's Disease is an inherited disease that causes nerve cells in the brain to waste away. Symptoms include uncontrolled movements, clumsiness, and balance problems. Huntington's disease can hinder walk, talk, and swallowing.

Ataxia refers to the loss of full control of bodily movements, and may affect the fingers, hands, arms, legs, body, speech, and eye movements.

Myloclonus and Startle is a response to a sudden and unexpected stimulus, which can be acoustic, tactile, visual, or vestibular.

Tics are an involuntary movement usually onset suddenly, brief, repetitive, but non-rhythmical, typically imitating normal behavior and often occurring out of a background of normal activity. Tics can be classified as motor or vocal, motor tics associated with movements while vocal tics associated with sound. Tics can be characterized as simple or complex. For example simple motor tics involve only a few muscles restricted to a specific body part. Tourette Syndrome is an inherited neuropsychiatric disorder with onset in childhood, characterized by multiple motor tics and at least one vocal tic.

Restless Legs Syndrome is a neurologic sensorimotor disorder characterized by an overwhelming urge to move the legs when at rest.

Stiff Person Syndrome is a progressive movement disorder characterized by involuntary painful spasms and rigidity of muscles, usually involving the lower back and legs. Stiff-legged gait with exaggerated lumbar hyperlordosis typically results. Characteristic abnormality on EMG recordings with continuous motor unit activity of the paraspinal axial muscles is typically observed. Variants include "stiff-limb syndrome" producing focal stiffness typically affecting distal legs and feet.

Gait disorders refer to an abnormalitiy in the manner or style of walking, which results from neuromuscular, arthritic, or other body changes. Gait is classified according to the system responsible for abnormal locomotion, and include hemiplegic gait, diplegic gait, neuropathic gait, myopathic gait, parkinsonian gait, choreiform gait, ataxic gait, and sensory gait.

Mood Disorders

Clinical depression is also known as major depression, major depressive disorder (MDD), unipolar depression, unipolar disorder, and recurrent depression, and refers to a mental disorder characterized by pervasive and persistent low mood that is accompanied by low self-esteem and loss of interest or pleasure in normally enjoyable activities. Some people with clinical depression have trouble sleeping, lose weight, and generally feel agitated and irritable. Clinical depression affects how an individual feels, thinks, and behaves and may lead to a variety of emotional and physical problems. Individuals with clinical depression may have trouble doing day-to-day activities and make an individual feel as if life is not worth living.

Postnatal depression (PND) is also referred to as postpartum depression (PPD), and refers to a type of clinical depression that affects women after childbirth. Symptoms can include sadness, fatigue, changes in sleeping and eating habits, reduced sexual desire, crying episodes, anxiety, and irritability.

Atypical depression (AD) is characterized by mood reactivity (e.g., paradoxical anhedonia) and positivity, significant weight gain or increased appetite. Patients suffering from AD also may have excessive sleep or somnolence (hypersomnia), a sensation of limb heaviness, and significant social impairment as a consequence of hypersensitivity to perceived interpersonal rejection.

Melancholic depression is characterized by loss of pleasure (anhedonia) in most or all activities, failures to react to pleasurable stimuli, depressed mood more pronounced than that of grief or loss, excessive weight loss, or excessive guilt.

Psychotic major depression (PMD) or psychotic depression refers to a major depressive episode, in particular of melancholic nature, where the individual experiences psychotic symptoms such as delusions and hallucinations.

Catatonic depression refers to major depression involving disturbances of motor behavior and other symptoms. An individual may become mute and stuporose, and either is immobile or exhibits purposeless or bizarre movements.

Seasonal affective disorder (SAD) refers to a type of seasonal depression wherein an individual has seasonal patterns of depressive episodes coming on in the fall or winter.

Dysthymia refers to a condition related to unipolar depression, where the same physical and cognitive problems are evident. They are not as severe and tend to last longer (e.g., at least 2 years).

Double depression refers to fairly depressed mood (dysthymia) that lasts for at least 2 years and is punctuated by periods of major depression.

Depressive Personality Disorder (DPD) refers to a personality disorder with depressive features.

Recurrent Brief Depression (RBD) refers to a condition in which individuals have depressive episodes about once per month, each episode lasting 2 weeks or less and typically less than 2-3 days.

Minor depressive disorder or minor depression refers to a depression in which at least 2 symptoms are present for 2 weeks.

Bipolar disorder or manic depressive disorder causes extreme mood swings that include emotional highs (mania or hypomania) and lows (depression). During periods of mania the individual may feel or act abnormally happy, energetic, or irritable. They often make poorly thought out decisions with little regard to the consequences. The need for sleep is usually reduced. During periods of depression there may be crying, poor eye contact with others, and a negative outlook on life. The risk of suicide among those with the disorder is high at greater than 6% over 20 years, while self harm occurs in 30-40%. Other mental health issues such as anxiety disorder and substance use disorder are commonly associated with bipolar disorder.

Depression caused by chronic medical conditions refers to depression caused by chronic medical conditions such as cancer or chronic pain, chemotherapy, chronic stress.

Treatment-resistant depression refers to a condition where the individuals have been treated for depression, but the symptoms do not improve. For example, antidepressants or physchological counseling (psychotherapy) do not ease depression symptoms for individuals with treatment-resistant depression. In some cases, individuals with treatment-resistant depression improve symptoms, but come back. Refractory depression occurs in patients suffering from depression who are resistant to standard pharmacological treatments, including tricyclic antidepressants, MAOIs, SSRIs, and double and triple uptake inhibitors and/or anxiolytic drugs, as well as non-pharmacological treatments (e.g., psychotherapy, electroconvulsive therapy, vagus nerve stimulation and/or transcranial magnetic stimulation).

Suicidality, suicidal ideation, suicidal behavior refers to the tendency of an individual to commit suicide. Suicidal ideation concerns thoughts about or an unusual preoccupation with suicide. The range of suicidal ideation varies greatly, from e.g., fleeting thoughts to extensive thoughts, detailed planning, role playing, incomplete attempts. Symptoms include talking about suicide, getting the means to commit suicide, withdrawing from social contact, being preoccupied with death, feeling trapped or hopeless about a situation, increasing use of alcohol or drugs, doing risky or self-destructive things, saying goodbye to people as if they won't be seen again.

Symptoms of depression include persistent anxious or sad feelings, feelings of helplessness, hopelessness, pessimism, worthlessness, low energy, restlessness, difficulty sleeping, sleeplessness, irritability, fatigue, motor challenges, loss of interest in pleasurable activities or hobbies, loss of concentration, loss of energy, poor self-esteem, absence of positive thoughts or plans, excessive sleeping, overeating, appetite loss, insomnia, self-harm, thoughts of suicide, and suicide attempts. The presence, severity, frequency, and duration of symptoms may vary on a case to case basis. Symptoms of depression, and relief of the same, may be ascertained by a physician or psychologist (e.g., by a mental state examination).

Anxiety Disorders

Provided herein are methods for treating anxiety disorders. Anxiety disorder is a blanket term covering several different forms of abnormal and pathological fear and anxiety. Current psychiatric diagnostic criteria recognize a wide variety of anxiety disorders.

Generalized anxiety disorder is a common chronic disorder characterized by long-lasting anxiety that is not focused on any one object or situation. Those suffering from generalized anxiety experience non-specific persistent fear and worry and become overly concerned with everyday matters. Generalized anxiety disorder is the most common anxiety disorder to affect older adults.

In panic disorder, a person suffers from brief attacks of intense terror and apprehension, often marked by trembling, shaking, confusion, dizziness, nausea, difficulty breathing. These panic attacks, defined by the APA as fear or discomfort that abruptly arises and peaks in less than ten minutes, can last for several hours and can be triggered by stress, fear, or even exercise; although the specific cause is not always apparent. In addition to recurrent unexpected panic attacks, a diagnosis of panic disorder also requires that said attacks have chronic consequences: either worry over the attacks' potential implications, persistent fear of future attacks, or significant changes in behavior related to the attacks. Accordingly, those suffering from panic disorder experience symptoms even outside of specific panic episodes. Often, normal changes in heartbeat are noticed by a panic sufferer, leading them to think something is wrong with their heart or they are about to have another panic attack. In some cases, a heightened awareness (hypervigilance) of body functioning occurs during panic attacks, wherein any perceived physiological change is interpreted as a possible life threatening illness (i.e. extreme hypochondriasis).

Obsessive compulsive disorder is a type of anxiety disorder primarily characterized by repetitive obsessions (distressing, persistent, and intrusive thoughts or images) and compulsions (urges to perform specific acts or rituals). The OCD thought pattern may be likened to superstitions insofar as it involves a belief in a causative relationship where, in reality, one does not exist. Often the process is entirely illogical; for example, the compulsion of walking in a certain pattern may be employed to alleviate the obsession of impending harm. And in many cases, the compulsion is entirely inexplicable, simply an urge to complete a ritual triggered by nervousness. In a minority of cases, sufferers of OCD may only experience obsessions, with no overt compulsions; a much smaller number of sufferers experience only compulsions.

The single largest category of anxiety disorders is that of phobia, which includes all cases in which fear and anxiety is triggered by a specific stimulus or situation. Sufferers typically anticipate terrifying consequences from encountering the object of their fear, which can be anything from an animal to a location to a bodily fluid.

Post-traumatic stress disorder or PTSD is an anxiety disorder which results from a traumatic experience. Post-traumatic stress can result from an extreme situation, such as combat, rape, hostage situations, or even serious accident. It can also result from long term (chronic) exposure to a severe stressor, for example soldiers who endure individual battles but cannot cope with continuous combat. Common symptoms include flashbacks, avoidant behaviors, and depression.

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

EXAMPLES

In order that the invention described herein may be more fully understood, the following examples are set forth. The synthetic and biological examples described in this application are offered to illustrate the compounds, pharmaceutical compositions and methods provided herein and are not to be construed in any way as limiting their scope.

Materials and Methods

The compounds provided herein can be prepared from readily available starting materials using the following general methods and procedures. For example, synthesis of starting materials may be described in WO2014/169831 and WO2015/027227. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in T. W. Greene and P. G. M. Wuts, *Protecting Groups in Organic Synthesis*, Second Edition, Wiley, New York, 1991, and references cited therein.

The compounds provided herein may be isolated and purified by known standard procedures. Such procedures include (but are not limited to) recrystallization, column chromatography, HPLC, or supercritical fluid chromatography (SFC). The following schemes are presented with details as to the preparation of representative heteroaryls and heterocyclyls that have been listed herein. The compounds provided herein may be prepared from known or commercially available starting materials and reagents by one skilled in the art of organic synthesis. Exemplary chiral columns available for use in the separation/purification of the enantiomers/diastereomers provided herein include, but are not limited to, CHIRALPAK® AD-10, CHIRALCEL® OB, CHIRALCEL® OB—H, CHIRALCEL® OD, CHIRALCEL® OD-H, CHIRALCEL® OF, CHIRALCEL® OG, CHIRALCEL® OJ and CHIRALCEL® OK.

$^1$H-NMR reported herein (e.g., for intermediates) may be a partial representation of the full NMR spectrum of a compound, e.g., a compound described herein. For example, the reported $^1$H NMR may exclude or partially represent the region between δ (ppm) of about 1 to about 2.5 ppm. For example, the reported $^1$H NMR may include an overestimated count of protons due to the presence of residual solvent or water.

Exemplary general method for preparative HPLC: Column: Waters RBridge prep 10 μm C18, 19*250 mm. Mobile phase: acetonitrile, water (NH$_4$HCO$_3$) (30 L water, 24 g NH$_4$HCO$_3$, 30 mL NH$_3$.H$_2$O). Flow rate: 25 mL/min Exemplary general method for LCMS: Gradient 10-80AB 2MIN (10% B at 0 min, 80% B at 0.9 min, 80% B at 1.5 min, 10% B at 1.51 min, 10% B at 2 min) on a Xtimate C18 2.1*30 mm, 3 um with A: water(4 L)+TFA(1.5 mL) and B: acetonitrile(4 L)+TFA(0.75 mL). Flow rate: 1.2 mL/min, wavelength UV 220 nm, oven temp 50° C. MS ionization MSI, Detector PDA, ELSD. Gradient 5-95AB 1.5MIN (5% B at 0 min, 95% B at 0.7 min, 95% B at 1.1 min, 5% B at 1.11 min, 5% B at 1.5 min) on a MERCK, RP-18e 25-2 mm column with A: water(4 L)+TFA(1.5 mL) and B: acetonitrile(4 L)+TFA(0.75 mL). Flow rate: 1.5 mL/min, wavelength UV 220 nm, oven temp 50° C. MS ionization ESI.

Exemplary general method for analytical HPLC: Mobile phase: A: water (10 mM NH$_4$HCO$_3$), B: acetonitrile, Gradient: 5%-95% B in 1.6 or 2 min Flow rate: 1.8 or 2 mL/min; Column: XBridge C18, 4.6*50 mm, 3.5 μm at 45 C.

Abbreviaton List

THF: tetrahydrofuran; PE: petroleum ether; DCM: dichloromethane; EtOAc: ethylacetate; PCC: pyridinium chlorochromate; t-BuOK: potassium tert-butoxide; TBAF: tetra-n-butylammonium fluoride; TBSCl: tert-Butyl(chloro) dimethylsilane; DMP: Dess-Martin periodinane; (i-PrO)$_4$Ti: titanium tetraisopropoxide; LAH: lithium aluminium hydride; MAD: methyl aluminum bis(2,6-di-t-butyl-4-methylphenoxide); BHT: 2,6-di-t-butyl-p-cresol (butylated hydroxytoluene); DIEA: diisopropylethylamine; NCS: N-chlorosuccinimide.

Synthetic Methods

Example 1. Synthesis of Compounds 1 and 2

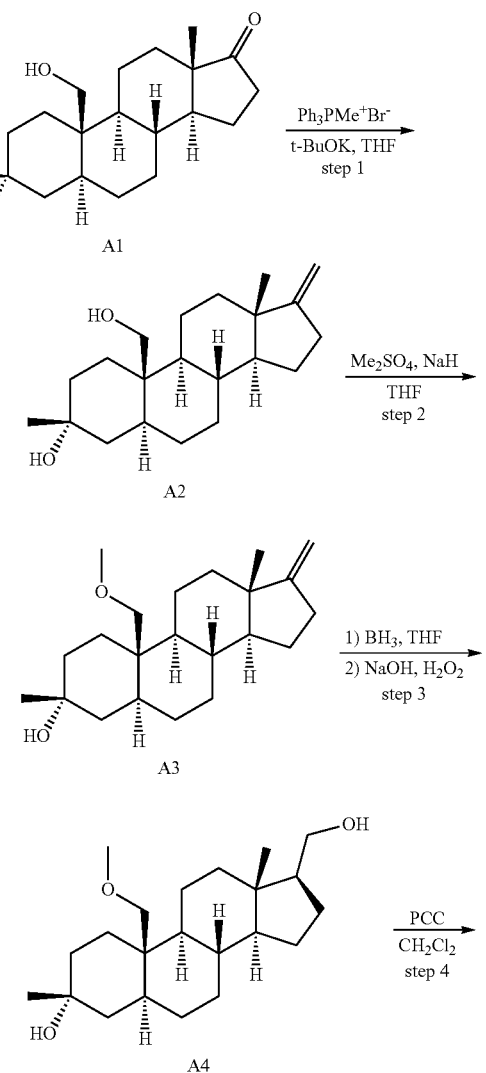

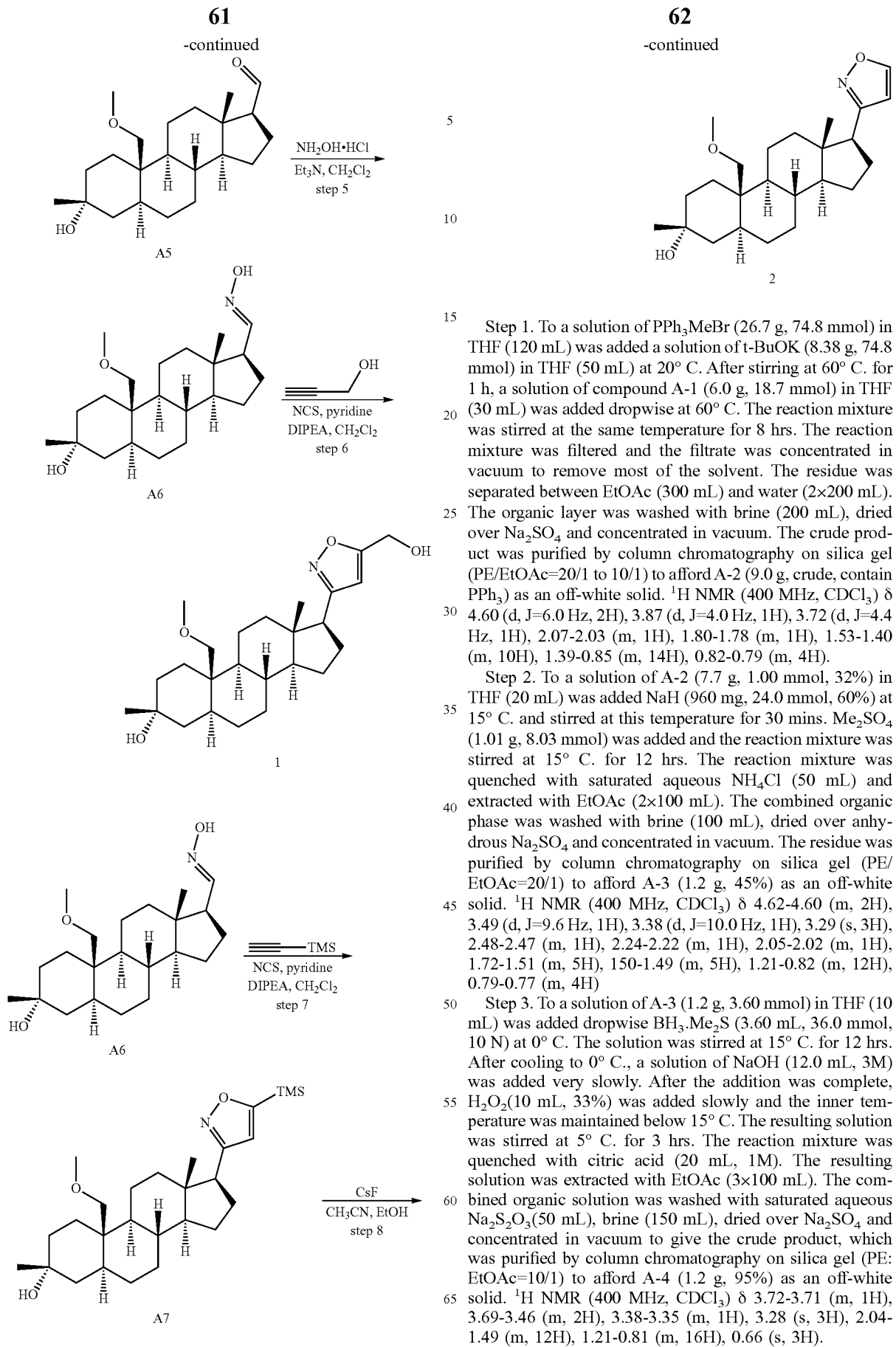

Step 1. To a solution of PPh₃MeBr (26.7 g, 74.8 mmol) in THF (120 mL) was added a solution of t-BuOK (8.38 g, 74.8 mmol) in THF (50 mL) at 20° C. After stirring at 60° C. for 1 h, a solution of compound A-1 (6.0 g, 18.7 mmol) in THF (30 mL) was added dropwise at 60° C. The reaction mixture was stirred at the same temperature for 8 hrs. The reaction mixture was filtered and the filtrate was concentrated in vacuum to remove most of the solvent. The residue was separated between EtOAc (300 mL) and water (2×200 mL). The organic layer was washed with brine (200 mL), dried over Na₂SO₄ and concentrated in vacuum. The crude product was purified by column chromatography on silica gel (PE/EtOAc=20/1 to 10/1) to afford A-2 (9.0 g, crude, contain PPh₃) as an off-white solid. $^1$H NMR (400 MHz, CDCl₃) δ 4.60 (d, J=6.0 Hz, 2H), 3.87 (d, J=4.0 Hz, 1H), 3.72 (d, J=4.4 Hz, 1H), 2.07-2.03 (m, 1H), 1.80-1.78 (m, 1H), 1.53-1.40 (m, 10H), 1.39-0.85 (m, 14H), 0.82-0.79 (m, 4H).

Step 2. To a solution of A-2 (7.7 g, 1.00 mmol, 32%) in THF (20 mL) was added NaH (960 mg, 24.0 mmol, 60%) at 15° C. and stirred at this temperature for 30 mins. Me₂SO₄ (1.01 g, 8.03 mmol) was added and the reaction mixture stirred at 15° C. for 12 hrs. The reaction mixture was quenched with saturated aqueous NH₄Cl (50 mL) and extracted with EtOAc (2×100 mL). The combined organic phase was washed with brine (100 mL), dried over anhydrous Na₂SO₄ and concentrated in vacuum. The residue was purified by column chromatography on silica gel (PE/EtOAc=20/1) to afford A-3 (1.2 g, 45%) as an off-white solid. $^1$H NMR (400 MHz, CDCl₃) δ 4.62-4.60 (m, 2H), 3.49 (d, J=9.6 Hz, 1H), 3.38 (d, J=10.0 Hz, 1H), 3.29 (s, 3H), 2.48-2.47 (m, 1H), 2.24-2.22 (m, 1H), 2.05-2.02 (m, 1H), 1.72-1.51 (m, 5H), 150-1.49 (m, 5H), 1.21-0.82 (m, 12H), 0.79-0.77 (m, 4H)

Step 3. To a solution of A-3 (1.2 g, 3.60 mmol) in THF (10 mL) was added dropwise BH₃.Me₂S (3.60 mL, 36.0 mmol, 10 N) at 0° C. The solution was stirred at 15° C. for 12 hrs. After cooling to 0° C., a solution of NaOH (12.0 mL, 3M) was added very slowly. After the addition was complete, H₂O₂ (10 mL, 33%) was added slowly and the inner temperature was maintained below 15° C. The resulting solution was stirred at 5° C. for 3 hrs. The reaction mixture was quenched with citric acid (20 mL, 1M). The resulting solution was extracted with EtOAc (3×100 mL). The combined organic solution was washed with saturated aqueous Na₂S₂O₃ (50 mL), brine (150 mL), dried over Na₂SO₄ and concentrated in vacuum to give the crude product, which was purified by column chromatography on silica gel (PE:EtOAc=10/1) to afford A-4 (1.2 g, 95%) as an off-white solid. $^1$H NMR (400 MHz, CDCl₃) δ 3.72-3.71 (m, 1H), 3.69-3.46 (m, 2H), 3.38-3.35 (m, 1H), 3.28 (s, 3H), 2.04-1.49 (m, 12H), 1.21-0.81 (m, 16H), 0.66 (s, 3H).

Step 4. To a solution of A-4 (1.1 g. 3.13 mmol) in DCM (20 mL) was added PCC (1.34 g, 6.26 mmol) at 15°. The mixture was stirred at 15° C. for 1 h. The reaction mixture was filtered and the filtrate was concentrated in vacuum. The residue was purified by column chromatography on silica gel (PE/EtOAc=10/1) to afford A-5 (1.2 g) as light yellow solid. $^1$H NMR (400 MHz, CDCl$_3$) δ 9.76 (s, 1H), 3.47 (d, J=10.8 Hz, 1H), 3.36 (d, J=10.0 Hz, 1H), 3.28 (s, 3H), 2.29-1.48 (m, 10H), 1.25-0.73 (m, 20H).

Step 5. To a solution of A-5 (1.2 g, 3.44 mmol) in DCM (10 ml) was added Et$_3$N (695 mg, 6.88 mmol) and NH$_2$OH.HCl (355 mg, 5.15 mmol) at 15° C. The mixture was stirred at 15° C. for 12 hrs. The reaction mixture was treated with water (30 mL), extracted with CH$_2$Cl$_2$ (50 mL×2). The combined organic phase was washed with brine (50 mL), dried over anhydrous Na$_2$SO$_4$, concentrated in vacuum to give A-6 (900 mg, crude) as an off-white solid. $^1$H NMR (400 MHz, CDCl$_3$) δ 7.40-7.37 (m, 1H), 3.47 (d, J=9.6 Hz, 1H), 3.36 (d, J=10.0 Hz, 1H), 3.28 (s, 3H), 2.16-1.49 (m, 12H), 1.2-0.70 (m, 19H).

Step 6. To a solution of A-6 (200 mg, 0.55 mmol) in 3 mL of DCM was added pyridine (86.1 mg, 1.09 mmol) and NCS (87.6 mg, 0.659 mmol). After stirring for 50 min, the reaction was treated with prop-2-yn-1-ol (302 mg, 5.39 mmol) followed by DIEA (140 mg, 1.09 mmol). The reaction mixture was stirred at 15° C. for 12 hrs. The reaction mixture was treated with water (20 mL), extracted with CH$_2$Cl$_2$ (2×30 mL). The combined organic phase was washed with brine (30 mL), dried over anhydrous Na$_2$SO$_4$, concentrated in vacuum to afford the crude product, which was purified by preparative HPLC to afford 1 (84 mg, 37%) as an off-white solid. $^1$H NMR (400 MHz, CDCl$_3$) δ 6.09 (s, 1H), 4.73 (s, 2H), 3.47 (d, J=10.4 Hz, 1H), 3.37 (d, J=10.0 Hz, 1H), 3.27 (s, 3H), 2.72-2.69 (m, 1H), 2.03-1.78 (m, 4H), 1.75-1.57 (m, 9H), 1.53-0.85 (m, 14H), 0.58 (s, 3H) LCMS Rt=0.86 min in 1.5 min chromatography, 5-95 AB, MS ESI calcd. for C$_{25}$H$_{40}$NO$_4$ [M+H]$^+$ 418, found 418.

Step 7. To a solution of A-6 (200 mg, 550 μmol) in 3 mL of DCM was added pyridine (86.1 mg, 1.09 mmol) and NCS (87.6 mg 659 μmol). After stirring for 50 mins, the reaction was treated with ethynyltrimethylsilane (270 mg, 2.75 mmol), followed by DIEA (140 mg, 1.09 mmol). The reaction mixture was stirred at 15° C. for 12 hrs. The reaction mixture was treated with water (20 mL), extracted with DCM (30 mL×2). The combined organic phase was washed with brine (30 mL), dried over anhydrous Na$_2$SO$_4$ and concentrated in vacuum to afford A-7 (300 mg, crude) as light yellow oil. LCMS Rt=1.104 min in 1.5 min chromatography, 5-95 AB, MS ESI calcd. for C$_{27}$H$_{46}$NO$_3$Si [M+H]$^+$ 460, found 460.

Step 8. To a solution of A-7 (200 mg, 435 μmol) in CH$_3$CN (6 mL) and EtOH (3 mL) was added CsF (72.6 mg, 478 μmol) at 15° C. and stirred for 12 hrs. The reaction mixture was filtered and the filtrate was concentrated in vacuum. The residue was purified by preparative HPLC to afford 2 (71.8 mg, 43%) as an off-white solid. $^1$H NMR (400 MHz, CDCl$_3$) δ 8.30 (s, 1H), 6.17 (s, 1H), 3.47 (d, J=10.0 Hz, 1H), 3.37 (d, J=10.0 Hz, 1H), 3.26 (s, 3H), 2.76-2.72 (m, 1H), 2.04-1.78 (m, 3H), 1.75-1.57 (m, 7H), 1.53-1.46 (m, 6H), 1.34-0.86 (m, 10H), 0.56 (s, 3H) LCMS Rt =0.950 min in 1.5 min chromatography, 5-95 AB, MS ESI calcd. for C$_{24}$H$_{38}$NO$_3$ [M+H]$^+$ 388, found 388.

Example 2. Synthesis of Compound 3

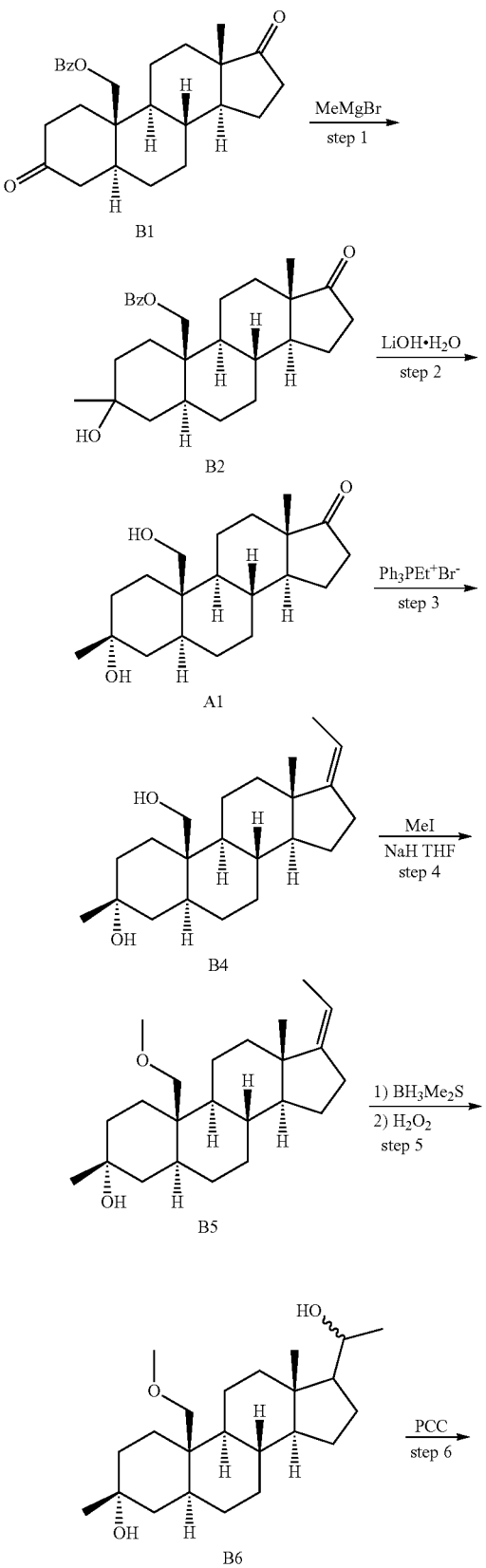

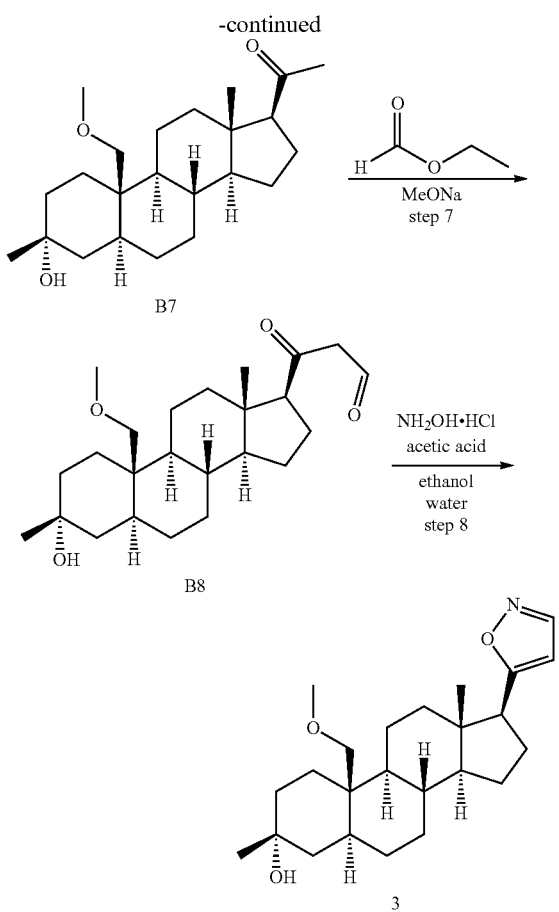

Step 1. To a solution of B-1 (53.75 g, 131.1 mmol) in THF (500 mL) was added MeMgBr (131 mL, 3M in ether, 393 mmol) dropwise to keep inner temperature below −70° C. The mixture was stirred at −78° C. for 4 hrs. To the mixture was added saturated aqueous NH$_4$Cl (262 mL) and the inner temperature was raised to −20° C. Saturated aqueous citric acid (131 mL) was added at −20° C. The mixture was warmed to 20° C. The organic layer was separated and extracted with EtOAc (3×300 mL). The combined organic layer was dried over Na$_2$SO$_4$, concentrated under vacuum to give B-2 (78.1 g, crude) as an off-white solid.

Step 2. To a mixture of B-2 (145 g, 341 mmol) in THF (300 mL) and MeOH (200 mL) was added a solution of LiOH (57.0 g, 1.36 mol) in water (100 mL). The mixture was stirred at 35° C. for 40 hrs. The mixture was extracted with EtOAc (3×1500 mL). The organic layer was dried over Na$_2$SO$_4$, concentrated under vacuum to give a residue, which was purified by column chromatography on silica gel (PE:EtOAc=5:1 to 3:1) to give A-1 (25 g pure and 129 g impure) as an off-white solid. $^1$H NMR (400 MHz, CDCl$_3$) δ 3.99-3.66 (m, 2H), 2.44 (dd, J=8.5, 19.1 Hz, 1H), 2.22-1.42 (m, 13H), 1.39-0.97 (m, 12H), 0.95-0.78 (m, 4H)

Step 3. To a suspension of PPh$_3$EtBr (34.7 g, 93.5 mmol) in THF (150 mL) was added t-BuOK (10.4 g, 93.5 mmol) at 25° C. under N$_2$. The resulting mixture was stirred at 65° C. for 1 hour. A-1 (10 g, 31.2 mmol) in THF (50 mL) was added at 65° C. The mixture was stirred at 65° C. for 16 hrs. Water (200 mL) was added at 25° C. The resulting mixture was extracted with EtOAc (3×150 mL). The combined organic phase was washed with water (200 mL), brine (200 mL), and concentrated under vacuum to give a residue, which was purified by chromatography on silica gel (PE:EtOAc=6/1) to afford B-4 (8.6 g, 83%) as an off-white solid $^1$H NMR (400 MHz, CDCl$_3$) δ 5.35-5.02 (m, 1H), 3.98-3.63 (m, 2H), 2.42-1.99 (m, 4H), 1.83-1.69 (m, 2H), 1.67-1.42 (m, 11H), 1.32 (d, J=13.1 Hz, 1H), 1.26-0.94 (m, 11H), 0.91 (s, 3H), 0.87-0.72 (m, 1H).

Step 4. To a suspension of B-4 (3.5 g, 10.5 mmol) in THF (40 mL) was added NaH (1.66 g, 60% w/w in mineral oil, 42.0 mmol) at 0° C. under N$_2$ atmosphere. The mixture was stirred at 45° C. for 1 h. MeI (1.63 g, 11.5 mmol) was added in portions at 45° C. during 6 hrs. The reaction mixture was quenched by water (40 mL) at 0° C. The mixture was extracted with DCM (3×120 mL). The combined organic phase was washed with brine (100 mL), dried over Na$_2$SO$_4$, filtered, and the filtrate was concentrated under vacuum to give a residue. The residue was purified by chromatography on silica gel (PE/EtOAc=6/1) to afford B-5 (1.2 g, 33%) as an off-white solid.

Step 5. To a solution of B-5 (1.3 g, 3.75 mmol) in THF (15 mL) was added dropwise a solution of BH$_3$.Me$_2$S (3.75 mL, 10 M, 37.5 mmol) at 0° C. The solution was stirred at 25° C. for 16 hrs. After cooling to 0° C., aqueous NaOH (12.4 mL, 3.0 M, 37.5 mmol) was added very slowly. H$_2$O$_2$(3.84 g, 33% w/w in water, 37.5 mmol) was added slowly and the inner temperature was maintained below 10° C. The resulting mixture was stirred at 25° C. for 2 hrs and extracted with EtOAc (3×100 mL). The combined organic phase was washed with saturated aqueous Na$_2$S$_2$O$_3$ (100 mL), brine (100 mL), dried over Na$_2$SO$_4$, filtered and concentrated in vacuum to give B-6 (1.42 g, crude) as an off-white solid, which was used in the next reaction directly.

Step 6. A mixture of B-6 (1.2 g, 75%, 2.46 mmol), PCC (793 mg, 3.68 mmol) and silica gel (880 mg) in DCM (50 mL) was stirred at 25° C. for 3 hrs. The reaction mixture was filtered and the filtered cake was washed with DCM (3×30 mL). The combined filtrate was concentrated in vacuum to give a residue, which was purified by chromatography on silica gel (PE:EtOAc=5/1) to give B7 (600 mg, 67%) as yellow solid. $^1$H NMR (400 MHz, CDCl$_3$) δ 3.51-3.33 (m, 2H), 3.28 (s, 3H), 2.54 (t, J=8.8 Hz, 1H), 2.26-2.13 (m, 1H), 2.11 (s, 3H), 2.07-1.95 (m, 2H), 1.76-1.44 (m, 8H), 1.40-1.28 (m, 2H), 1.26-0.68 (m, 13H), 0.63 (s, 3H).

Step 7. To solution of B-7 (600 mg, 1.65 mmol) in ethyl formate (10 mL) was added NaOMe (266 mg, 4.94 mmol) at 25° C. The resulting mixture was stirred at 25° C. for 4 hrs. The reaction mixture was concentrated under vacuum to give B-8 (850 mg, crude) as yellow solid, which was used in the next reaction directly.

Step 8. To a suspension of B-8 (550 mg, 60% percent weight, 876 μmol) and hydroxylamine hydrochloride (303 mg, 4.37 mmol) in EtOH (25 mL) was added AcOH (2 mL), followed by water (1 mL). The resulting mixture was stirred at 80° C. for 4 hrs. The reaction mixture was concentrated under vacuum to give an off-white solid, which was purified by preparative HPLC (0.05% ammonia additive) to afford 3 (80.1 mg, 24%) as an off-white solid. $^1$H NMR (400 MHz, CDCl$_3$) δ 8.14 (d, J=1.5 Hz, 1H), 5.96 (s, 1H), 3.50-3.32 (m, 2H), 3.26 (s, 3H), 2.80 (t, J=9.8 Hz, 1H), 2.15-1.96 (m, 3H), 1.95-1.85 (m, 1H), 1.84-1.42 (m, 8H), 1.41-0.92 (m, 13H), 0.91-0.77 (m, 1H), 0.54 (s, 3H) LCMS Rt=1.29 min in 2.0 min chromatography, 10-80AB, MS ESI calcd. for C$_{24}$H$_{38}$NO$_3$ [M+H]$^+$ 388, found 388.

Example 3. Synthesis of Compound 4

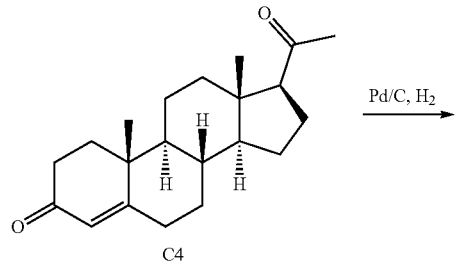
C4

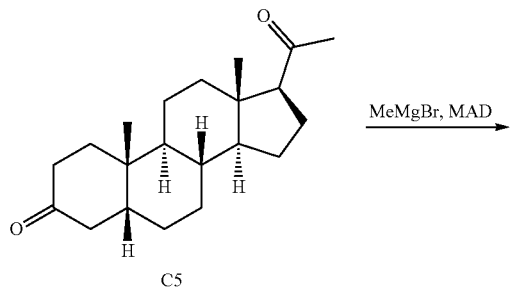
C5

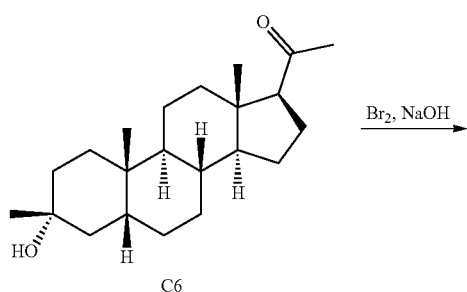
C6

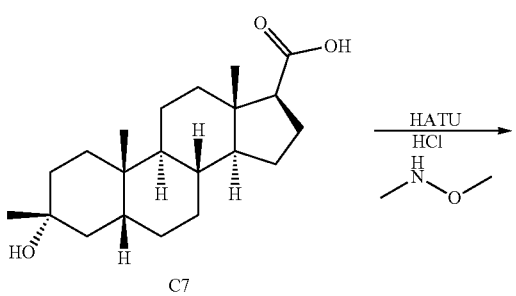
C7

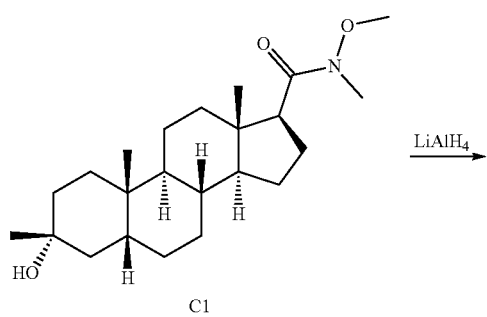
C1

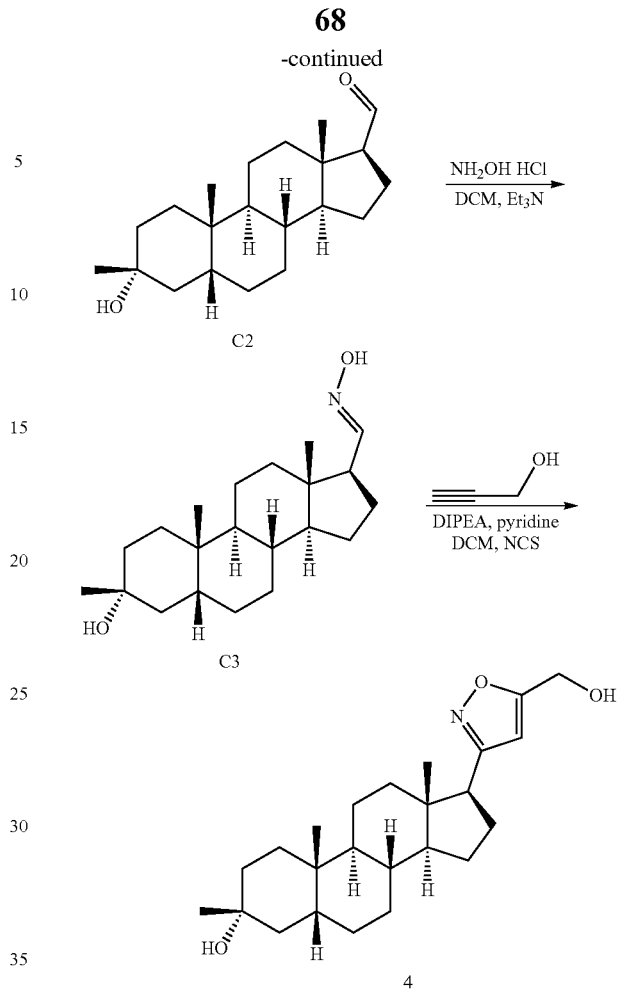

Step 1. A mixture of C4 (40 g, 127 mmol) and Pd/C (4 g) in EtOAc (200 mL) and THF (200 mL) was stirred at 25° C. under $H_2$ (15 psi) for 4 hrs. The reaction mixture was filtrated through a pad of celite and the filter cake was washed with EtOAc (5×40 mL). The combined organic phase was concentrated under vacuum to give C5 (41 g, crude) as an off white solid. $^1$H NMR (400 MHz, $CDCl_3$) δ 2.69 (t, J=14.0 Hz, 1H), 2.61-2.48 (m, 1H), 2.43-2.25 (m, 1H), 2.24-1.96 (m, 8H), 1.95-1.78 (m, 2H), 1.75-1.07 (m, 13H), 1.03 (s, 3H), 0.64 (s, 3H).

Step 2. To a solution of BHT (170 g, 774 mmol) in toluene (150 mL) was added $AlMe_3$ (193 mL, 387 mmol, 2.0 M in toluene) drop-wise blew 25° C. under $N_2$ atmosphere. The resulting mixture was stirred at 25° C. for 1 hour. C5 (41 g, 129 mmol) in toluene (50 mL) was added at −78° C. Then the mixture was stirred at −78° C. for 1 hour. MeMgBr (129 mL, 387 mmol, 3.0 M in diethyl ether) was added at −78° C. The reaction mixture was stirred at −78° C. for 4 hours. The mixture was quenched by saturated aqueous $NH_4Cl$ (20 mL), extracted with ethyl acetate (2×150 mL). The combined organic phase was washed with brine (150 mL), dried over anhydrous $Na_2SO_4$. The ethyl acetate solvent was evaporated to afford a crude solid, which was purified by chromatography on silica gel (PE/EtOAc=7/1) to afford product C6 (36 g, impure) as a light yellow solid. $^1$H NMR (400 MHz, $CDCl_3$) δ 2.58-2.46 (m, 1H), 2.22-2.09 (m, 4H), 2.06-1.79 (m, 3H), 1.78-0.99 (m, 22H), 0.94 (s, 3H), 0.59 (s, 3H).

Step 3. Liquid bromine (5.76 g, 36.0 mmol) was added slowly to a vigorously stirred aqueous solution of NaOH (48.0 mL, 3 M, 144 mmol) at 0° C. When all the bromine had dissolved, the mixture was diluted with cold dioxane (10 mL) and the ice-cold hypobromite solution was added slowly to a stirring solution of C6 (4 g, 12.0 mmol) in dioxane (15 mL) and water (10 mL). The homogeneous yellow solution slowly became colorless and a white precipitate formed. The reaction mixture was stirred at 25° C. for 16 hours. The remaining oxidizing agent was destroyed by aqueous Na$_2$S$_2$O$_3$ (30 mL) and the mixture was then heated at 80° C. until the solid material dissolved. Acidification of the solution to pH=6 with hydrochloric acid (3 N) furnished a white precipitate, which was collected by filtration, washed with water (3×100 mL) and dried under vacuum to afford C7 (4.01 g, 100%) as an off white solid.

$^1$H NMR (400 MHz, DMSO-d$_6$) δ 11.90 (s, 1H), 4.24 (s, 1H), 2.28 (t, J=8.8 Hz, 1H), 2.01-1.54 (m, 8H), 1.50-1.28 (m, 5H), 1.26-0.92 (m, 12H), 0.91 (s, 3H), 0.61 (s, 3H).

Step 4. To a suspension of C7 (4.01 g, 11.9 mmol) and N,O-dimethylhydroxylamine hydrochloride (4.64 g, 47.6 mmol) in DMF (40 mL) was added HATU (9.04 g, 23.8 mmol) at 25° C. Then DIPEA (15.3 g, 119 mmol) was added to the resulting mixture. The reaction mixture was stirred at 25° C. for 2 hours. Water (500 mL) was added to the reaction mixture at 25° C. A precipitate in the mixture was filtrated to give a light yellow solid, which was washed with water (3×40 mL) and dried under vacuum to afford C1 (4.31 g, 96%) as light yellow solid.

$^1$H NMR (400 MHz, DMSO-d$_6$) δ 4.23 (s, 1H), 3.61 (s, 3H), 3.09 (br. s., 3H), 2.77-2.74 (m, 1H), 2.07-1.93 (m, 1H), 1.91-1.53 (m, 5H), 1.51-1.27 (m, 7H), 1.26-0.93 (m, 12H), 0.90 (s, 3H), 0.61 (s, 3H).

Step 5. To a stirred solution of C-1 (100 mg, 264 µmol) in 3 mL of THF was added LiAlH$_4$ (20 mg, 0.528 mmol) in 2 mL of THF dropwise at −45° C. The reaction mixture was quenched with aqueous NH$_4$Cl (20 mL), extracted with EtOAc (2×50 mL), washed with brine (2×30 mL), dried over Na$_2$SO$_4$, filtered, and evaporated to give crude product (90 mg) as a yellow oil.

Step 6. To a stirred solution of C-2 (90 mg, 282 µmol) in 3 mL of DCM was added hydroxylamine hydrochloride (29.3 mg, 0.423 mmol) and triethylamine (154 µL, 1.12 mmol) at 25° C. The reaction mixture was poured into ice-cold water and extracted with EtOAc (2×50 mL), washed with brine (2×30 mL), dried over Na$_2$SO$_4$, filtered and evaporated to give crude product (100 mg) as yellow oil.

Step 7. To a solution of C-3 (100 mg, 299 µmol) in DCM (3 mL) was added pyridine (0.1 mL) and 1-chloropyrrolidine-2,5-dione (39.7 mg, 299 µmol) at 25° C. The mixture was stirred at 25° C. for 1 h. The reaction was treated with neat prop-2-yn-1-ol (50.2 mg, 897 µmol) followed by DIEA (0.1 mL). After stirring 3 hrs, the residue was purified by preparative HPLC separation (column: Phenomenex Synergi C18 150*30 mm*4 um, gradient: 52-82% B (A=0.05% HCl-ACN, B=acetonitrile), flow rate: 30 mL/min) to obtain 4 (19 mg, 17%) as an off-white solid.

1H NMR (CDCl$_3$, 400 MHz): δ=6.09 (s, 1H), 4.74 (s, 2H), 2.71 (t, J=9.8 Hz, 1H), 1.90-2.19 (m, 4H), 1.66-1.88 (m, 4H), 1.37-1.63 (m, 10H), 1.21-1.29 (m, 7H), 1.16 (d, J=13.6 Hz, 1H), 1.05 (td, J=14.4, 3.8 Hz, 1H), 0.95 (s, 3H), 0.55 (s, 3H)

LCMS R$_t$=2.656 min in 4 min chromatography, 10-80AB, MS ESI calcd. for C$_{24}$H$_{38}$NO$_3$ [M+H]$^+$ 388, found 388.

Example 4. Synthesis of Compound 5

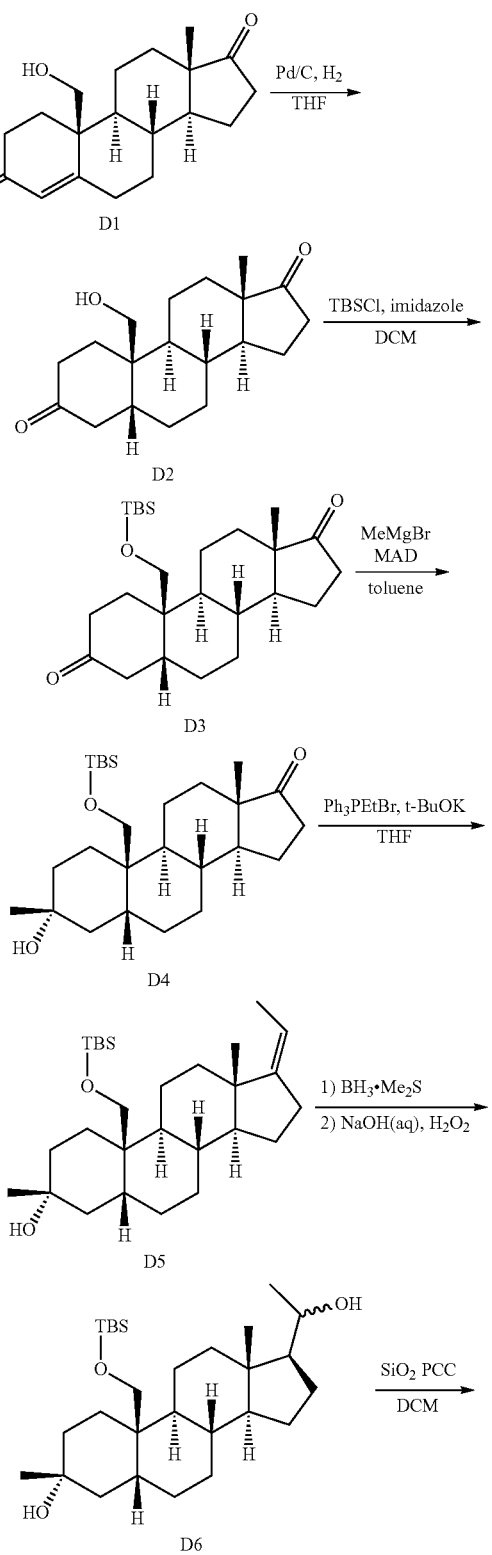

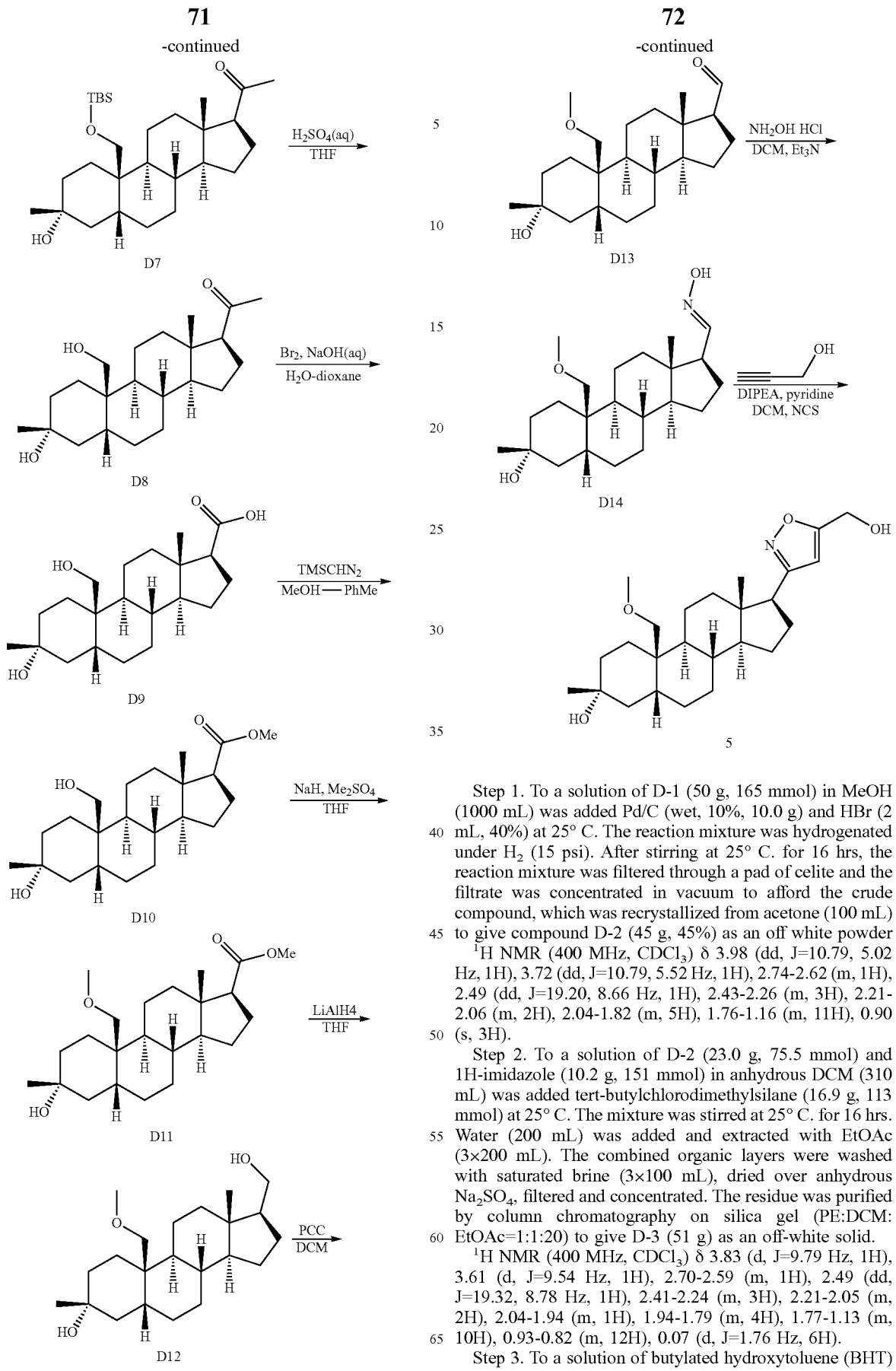

Step 1. To a solution of D-1 (50 g, 165 mmol) in MeOH (1000 mL) was added Pd/C (wet, 10%, 10.0 g) and HBr (2 mL, 40%) at 25° C. The reaction mixture was hydrogenated under $H_2$ (15 psi). After stirring at 25° C. for 16 hrs, the reaction mixture was filtered through a pad of celite and the filtrate was concentrated in vacuum to afford the crude compound, which was recrystallized from acetone (100 mL) to give compound D-2 (45 g, 45%) as an off white powder $^1$H NMR (400 MHz, $CDCl_3$) δ 3.98 (dd, J=10.79, 5.02 Hz, 1H), 3.72 (dd, J=10.79, 5.52 Hz, 1H), 2.74-2.62 (m, 1H), 2.49 (dd, J=19.20, 8.66 Hz, 1H), 2.43-2.26 (m, 3H), 2.21-2.06 (m, 2H), 2.04-1.82 (m, 5H), 1.76-1.16 (m, 11H), 0.90 (s, 3H).

Step 2. To a solution of D-2 (23.0 g, 75.5 mmol) and 1H-imidazole (10.2 g, 151 mmol) in anhydrous DCM (310 mL) was added tert-butylchlorodimethylsilane (16.9 g, 113 mmol) at 25° C. The mixture was stirred at 25° C. for 16 hrs. Water (200 mL) was added and extracted with EtOAc (3×200 mL). The combined organic layers were washed with saturated brine (3×100 mL), dried over anhydrous $Na_2SO_4$, filtered and concentrated. The residue was purified by column chromatography on silica gel (PE:DCM:EtOAc=1:1:20) to give D-3 (51 g) as an off-white solid.

$^1$H NMR (400 MHz, $CDCl_3$) δ 3.83 (d, J=9.79 Hz, 1H), 3.61 (d, J=9.54 Hz, 1H), 2.70-2.59 (m, 1H), 2.49 (dd, J=19.32, 8.78 Hz, 1H), 2.41-2.24 (m, 3H), 2.21-2.05 (m, 2H), 2.04-1.94 (m, 1H), 1.94-1.79 (m, 4H), 1.77-1.13 (m, 10H), 0.93-0.82 (m, 12H), 0.07 (d, J=1.76 Hz, 6H).

Step 3. To a solution of butylated hydroxytoluene (BHT) (157 g, 714 mmol) in anhydrous toluene (500 mL) was added AlMe$_3$ (178 mL, 2 M in toluene, 357 mmol) dropwise at 10° C. under N$_2$. The mixture was stirred at 25° C. for 1 h. To the mixture was added a solution of D-3 (50 g, 119 mmol) in anhydrous toluene (100 mL) dropwise at −70° C. under N$_2$. The mixture was stirred at −70° C. for 1 hour. A solution of MeMgBr (102 mL, 3 M in ether, 309 mmol) was added dropwise at −70° C. The mixture was stirred at −70° C. for another 3 hrs under N$_2$. To the mixture was added saturated citric acid solution (100 mL) dropwise. The mixture was extracted with EtOAc (3×800 mL). The combined organic layers were washed with brine (3×800 mL), dried over anhydrous Na$_2$SO$_4$, filtered and concentrated in vacuum. The residue was purified by column chromatography on silica gel (PE:EtOAc=10:1-3:1) to give D-4 (50 g).
$^1$H NMR (400 MHz, CDCl$_3$) δ 3.77 (d, J=9.54 Hz, 1H), 3.41 (d, J=9.54 Hz, 1H), 2.44 (dd, J=19.20, 8.66 Hz, 1H), 2.08 (dt, J=18.82, 9.16 Hz, 1H), 2.01-1.72 (m, 5H), 1.66-1.39 (m, 10H), 1.34-1.14 (m, 9H), 0.93-0.82 (m, 12H), 0.05 (d, J=3.01 Hz, 6H).

Step 4. To a solution of PPh$_3$PEtBr (138.35 g, 345 mmol) in anhydrous THF (100 mL) at 25° C. was added t-BuOK (38.64 g, 345 mmol) dropwise under N$_2$. After stirring at 60° C. for 1 h, D-4 (30 g, 69.0 mmol) in anhydrous THF (100 mL) was added to the above mixture dropwise. The mixture was stirred at 60° C. for 12 hrs. The reaction mixture was quenched with saturated NH$_4$Cl (30 mL) and extracted with EtOAc (3×150 mL). The combined organic layers were washed with brine (3×200 mL), dried over anhydrous Na$_2$SO$_4$, filtered and concentrated. The residue was purified by column chromatography on silica gel (PE:EtOAc=10:1) to give D-5 (45 g, impure) as an off-white solid.
$^1$H NMR (400 MHz, CDCl$_3$) δ 5.13 (d, J=6.78 Hz, 1H), 3.94-3.70 (m, 2H), 3.50-3.34 (m, 1H), 2.49-2.11 (m, 3H), 2.06-1.72 (m, 4H), 1.71-1.38 (m, 11H), 1.35-1.07 (m, 10H), 1.01-0.81 (m, 12H), 0.07 (s, 6H).

Step 5. To a solution of D-5 (44.6 g, 99.9 mmol) in THF (300 mL) was added dropwise a solution of BH$_3$-Me$_2$S (100 mL, 1000 mmol) at 0° C. The solution was stirred 25° C. for 3 hrs. After cooling to 0° C., a solution of NaOH (403 mL, 3M) was added very slowly. After the addition, H$_2$O$_2$ (123 g, 33%) was added slowly and the inner temperature was maintained below 10° C. The resulting solution was stirred at 25° C. for 2 hrs. The resulting solution was extracted with EtOAc (3×300 mL). The combined organic solution was washed with saturated aqueous Na$_2$S$_2$O$_3$ (3×100 mL), brine (100 mL), dried over Na$_2$SO$_4$ and concentrated in vacuum to give the crude product (70 g) as a solid. The crude product was used for the next step without further purification.

Step 6. A mixture of D-6 (70 g, crude), PCC (32.4 g, 150 mmol) and silica gel (35.7 g, w/w=1/1.1) in DCM (500 mL) was stirred at 25° C. for 12 hrs. The solution was filtered and the filtered cake was washed with DCM. The combined filtrate was concentrated in vacuum. The residue was purified by silica gel column eluted with PE/EtOAc=15/1 to 8:1 to give D-7 (31 g, impure) as an off-white solid.

Step 7. To a solution of D-7 (30.0 g, 64.8 mmol) in anhydrous THF (150 mL) was added H$_2$SO$_4$ (64.5 mL, 129 mmol, 2M in H$_2$O) at 10° C. dropwise. After stirring at 50° C. for 27 hrs, the reaction mixture was quenched with saturated NH$_4$Cl (20 mL) and extracted with EtOAc (3×25 mL). The combined organic layers were washed with saturated brine (3×20 mL), dried over anhydrous Na$_2$SO$_4$, filtered and concentrated. The residue was purified by column chromatography on silica gel (PE:EtOAc=10:1-2:1) to give D-8 (16 g) as an off white solid.

$^1$H NMR (400 MHz, CDCl$_3$) δ 3.95-3.83 (m, 1H), 3.51 (d, J=11.04 Hz, 1H), 2.51 (t, J=8.78 Hz, 1H), 2.20-2.07 (m, 4H), 2.06-1.84 (m, 4H), 1.83-1.34 (m, 11H), 1.32-1.05 (m, 11H), 0.62-0.53 (m, 3H).

Step 8. Br$_2$ (1.37 g, 8.58 mmol) was added slowly to a vigorously stirred solution of NaOH (11.4 mL, 3M in H$_2$O) in an ice bath. When all the bromine had dissolved, the mixture was diluted with 4 mL of cold dioxane and the ice-cold hypobromite solution was added slowly to a stirred solution of 1.0 g of D-8 in 6 mL of dioxane and 1 mL of water. The homogeneous yellow solution slowly became colorless and a white precipitate formed. After stirring for 15 hrs at 25° C., the remaining oxidizing agent was destroyed by the addition of excess Na$_2$S$_2$O$_3$ solution and the mixture was heated at 80° C. until the solid material dissolved. The mixture was acidified with concentrated HCl. The solid was collected, washed with water and dried to give 1.0 g of a brown solid (100% yield).
$^1$H NMR (400 MHz, CDCl$_3$) δ 3.65 (d, J=10.54 Hz, 1H), 3.22 (d, J=10.54 Hz, 1H), 2.27 (t, J=9.29 Hz, 1H), 0.99-2.04 (m, 28H), 0.59 (s, 3H).

Step 9. To a solution of D-9 (7.0 g, 19.9 mmol) in MeOH (28 mL) and toluene (7 mL) was added TMSCHN$_2$ (30 mL) at 0° C. The mixture was warmed to 15° C. and stirred at the same temperature for 12 hrs. The mixture was quenched with AcOH (25 mL). The resulting solution was extracted with EtOAc (3×150 mL). The combined organic layers was washed with saturated NaCl (100 mL), dried over anhydrous Na$_2$SO$_4$ and evaporated in vacuo to give crude product, which was purified by column chromatography on silica gel (PE/EtOAc=10/1-3:1) to afford D-10 (5.2 g) as an off-white solid.
$^1$H NMR (400 MHz, CDCl$_3$) δ 3.94-3.87 (m, 1H), 3.69-3.63 (m, 3H), 3.52 (d, J=11.04 Hz, 1H), 2.29-2.39 (m, 1H), 2.06-2.20 (m, 1H), 1.36-2.01 (m, 12H), 1.09-1.33 (m, 14H), 0.63 (s, 3H).

Step 10. To a solution of D-10 (2.0 g, 5.48 mmol) in THF (15 mL) was added NaH (0.76 g, 19.1 mmol). The mixture was stirred at 15° C. for 0.5 h. Me$_2$SO$_4$ (694 mg, 5.5 mmol) was added. The mixture was stirred at 15° C. for 15 hrs. To the reaction mixture was added water (50 mL) and extracted with EtOAc (3×20 mL). The combined organic layers were washed with saturated brine (3×20 mL), dried over anhydrous Na$_2$SO$_4$, filtered and concentrated. The residue was purified by column chromatography on silica gel (PE: EtOAc=10:1-4:1) to give D-11 (3.5 g) as an off-white solid.
$^1$H NMR (400 MHz, CDCl$_3$) δ 3.75-3.64 (m, 3H), 3.61-3.47 (m, 1H), 3.35 (s, 3H), 3.24-3.13 (m, 1H), 2.41-2.30 (m, 1H), 2.21-2.08 (m, 1H), 2.03-1.37 (m, apparent 17H, residual ethyl acetate), 1.32 (m, apparent 12H, residual ethyl acetate), 0.66 (s, 3H).

Step 11. To a solution of D-11 (580 mg, 1.53 mmol) in THF (8 mL) was added LiAlH$_4$ (174 mg, 4.59 mmol) at 0° C. The mixture was stirred at 15° C. for 0.5 h. To the reaction mixture was added water (1.8 mL), NaOH (5.4 mL, 10% aq) and water (1.8 mL). The mixture was extracted with EtOAc (3×35 mL). The combined organic layers were washed with saturated brine (3×10 mL), dried over anhydrous Na$_2$SO$_4$, filtered and concentrated. Crude D-12 (0.75 g) was used as is in the next step.

Step 12. A mixture of D-12 (750 mg, crude), PCC (915 mg, 4.26 mmol) and silica gel (1000 mg, w/w=1/1.1) in DCM (8 mL) was stirred at 15° C. for 12 hrs. The solution was filtered and the filtered cake was washed with DCM. The combined filtrate was concentrated in vacuum. The residue was purified by silica gel column eluted with PE/EtOAc=2:1 to give D-13 (740 mg) as an off-white solid.

Step 13. To a solution of D-13 (770 mg, 2.2 mmol) in anhydrous DCM (8 mL) was added hydroxylamine hydrochloride (229 mg, 3.3 mmol) and TEA (666 mg, 6.6 mmol) at 15° C. The mixture was stirred at 15° C. for 2 hrs. Water (10 mL) was added and extracted with EtOAc (3×20 mL). The combined organic layers were washed with saturated brine (3×10 mL), dried over anhydrous $Na_2SO_4$, filtered and concentrated. The residue was purified by column chromatography on silica gel (PE:EtOAc=1:1) to give D-14 (0.8 g) as an off-white solid.

Step 14. To a solution of D-14 (150 mg, 0.4 mmol) in anhydrous DCM (3 mL) was added pyridine (32 mg, 0.4 mmol) and NCS (55 mg, 0.4 mmol) at 15° C. The mixture was stirred at 15° C. for 1.5 hrs. DIEA (53 mg, 0.4 mmol) and prop-2-yn-1-ol (69 mg, 1.23 mmol) was added. Water (10 mL) was added and the mixture was extracted with EtOAc (3×20 mL). The combined organic layers were washed with saturated brine (3×10 mL), dried over anhydrous $Na_2SO_4$, filtered and concentrated. The residue was purified by preparative HPLC (0.5% HCl additive) to give 5 (18 mg, 10% yield) as an off-white solid.

$^1$H NMR (400 MHz, $CDCl_3$) δ 6.11 (s, 1H), 4.77 (s, 2H), 3.60 (d, J=9.03 Hz, 1H), 3.41-3.29 (m, 3H), 3.20 (d, J=9.03 Hz, 1H), 2.73 (t, J=9.66 Hz, 1H), 2.23-1.99 (m, 2H), 1.98-1.89 (m, 2H), 1.88-1.74 (m, 2H), 1.68-1.42 (m, 10H), 1.37-1.09 (m, 10H), 0.58 (s, 3H).

LCMS Rt=1.116 min in 2 min chromatography, 10-80AB, MS ESI calcd. for $C_{25}H_{39}NO_4$ [M+H]+ 418, found 418.

Example 5. Synthesis of Compounds 6 and 7

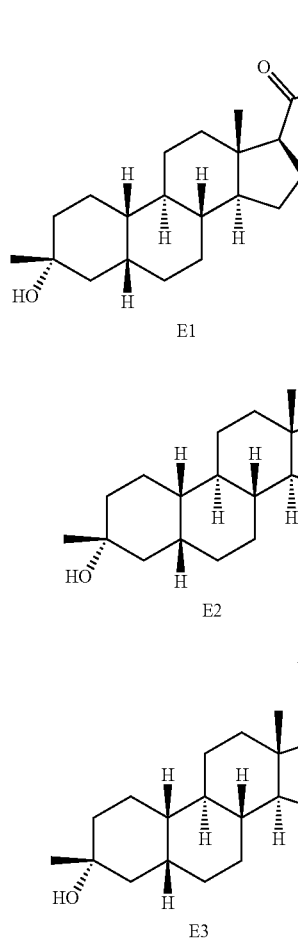

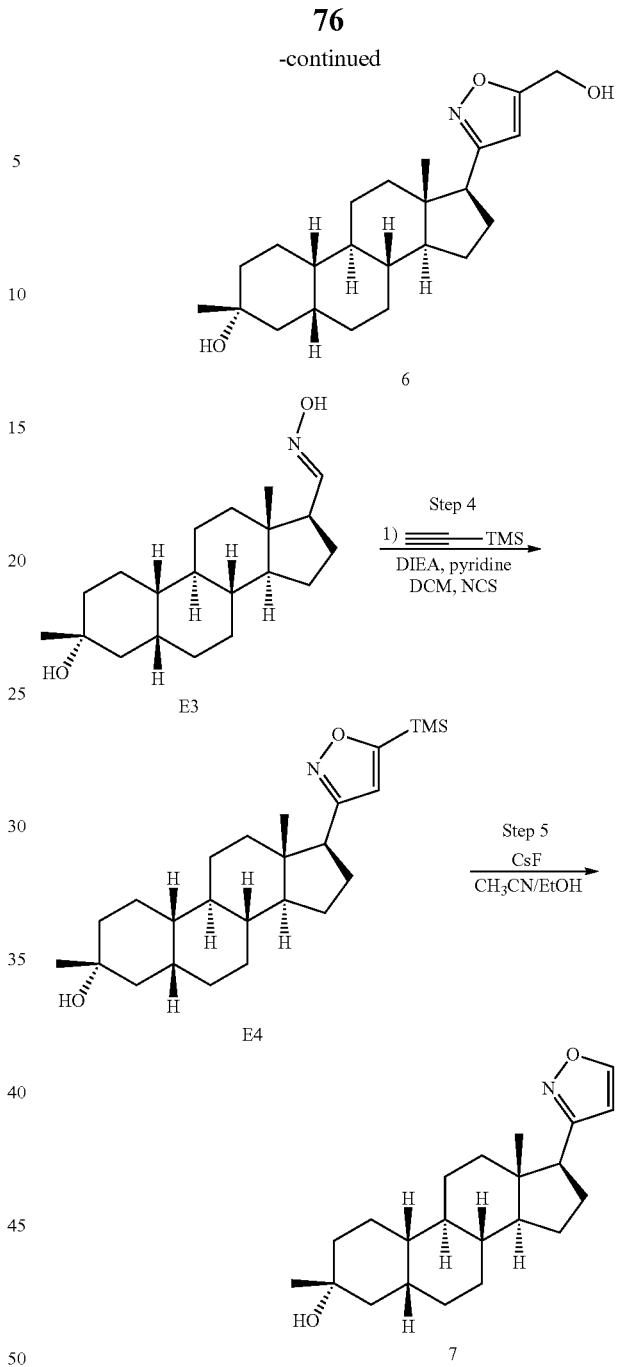

Step 1. To a solution of E-1 (400 mg, 1.1 mmol) in THF (5 mL) was added a solution LAH (83.6 mg, 2.2 mmol) in THF (3 mL) dropwise below −30° C. The solution was stirred at −30° C. for 3 hrs. The reaction was quenched by saturated aqueous $NH_4Cl$ (5 mL) at −30° C. The resulting mixture was extracted with EtOAc (2×30 mL). The combined organic layers were washed with brine (2×30 mL) and concentrated in vacuum to afford E-2 (380 mg, crude) as a light yellow solid.

Step 2. To a solution of E-2 (380 mg, 1.24 mmol) in DCM (8 mL) was added TEA (375 mg, 3.72 mmol) and hydroxylamine hydrochloride (172 mg, 2.48 mmol) at 25° C. The mixture was stirred at 25° C. for 16 hrs. The mixture was poured into water (50 mL) and extracted with DCM (2×50 mL). The combined organic layers were washed with brine (30 mL), dried over Na$_2$SO$_4$ and concentrated in vacuum to give E-3 (360 mg, crude) as an off-white solid.

Step 3. A solution of E-3 (180 mg, 563 umol) in DCM (5 mL) was added pyridine (0.2 mL) and 1-chloropyrrolidine-2,5-dione (75.1 mg, 563 μmol) at 25° C. The mixture was stirred at 25° C. for 20 mins. The reaction was treated with neat prop-2-yn-1-ol (94.1 mg, 1.68 mmol), followed by DIEA (0.2 mL). After stirring for 1 h, the reaction was concentrated in vacuum. The residue was purified by preparative HPLC to afford 6 (138.8 mg, 66%) as an off-white solid.

1H NMR (400 MHz, CDCl$_3$) δ 6.10 (s, 1H), 4.74 (s, 2H), 2.72 (t, J=9.7 Hz, 1H), 2.12-1.98 (m, 2H), 1.89-1.73 (m, 5H), 1.72-1.60 (m, 3H), 1.52-1.36 (m, 6H), 1.36-1.22 (m, 9H), 1.16-0.96 (m, 3H), 0.57 (s, 3H).

Step 4. A solution of E-3 (180 mg, 563 μmol) in DCM (8 mL) was added pyridine (0.2 mL) and 1-chloropyrrolidine-2,5-dione (75.1 mg, 563 μmol) at 25° C. The mixture was stirred at 25° C. for 1 h. The reaction was treated with neat ethynyltrimethylsilane (165 mg, 1.68 mmol) followed by neat DIEA (0.2 mL). After stirring for 16 hrs at 25° C., the reaction was poured into water (50 mL) and extracted with DCM (2×15 mL). The combined organic layers were washed with brine (30 mL), dried over Na$_2$SO$_4$ and concentrated in vacuum to give E-4 (200 mg, crude) as a light yellow solid.

Step 5. To a mixture of E-4 (200 mg, 481 μmol) in acetonitrile (6 mL) and EtOH (3 ml) was added CsF (80.3 mg, 529 μmol) at 25° C. The mixture was stirred at 25° C. for 16 hrs. The reaction was poured into water (30 mL) and extracted with DCM (2×30 mL). The combined organic layer was washed with brine (50 mL), dried over anhydrous Na$_2$SO$_4$, filtered and concentrated to afford the crude product. The residue was purified by preparative HPLC (0.5% HCl can additive) to afford 7 (40 mg, 24%) as an off-white solid.

1H NMR (400 MHz, CDCl$_3$) δ 8.34-8.28 (d, J=1.5 Hz, 1H), 6.18 (d, J=1.5 Hz, 1H), 2.82-2.72 (m, 1H), 2.20-1.99 (m, 2H), 1.90-1.75 (m, 5H), 1.73-1.59 (m, 2H), 1.50-1.38 (m, 6H), 1.35-1.27 (m, 9H), 1.21-0.95 (m, 3H), 0.56 (s, 3H).

LCMS R$_t$=1.111 min in 2 min chromatography, 30-90AB, MS ESI calcd. for C22H34NO2 [M+H] 344, found 344.

Example 6. Synthesis of 8

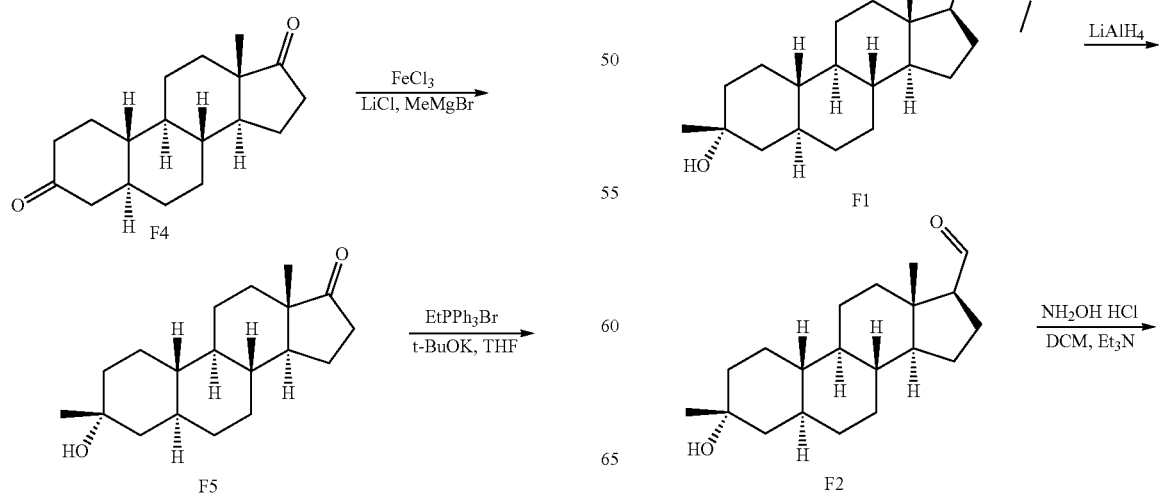

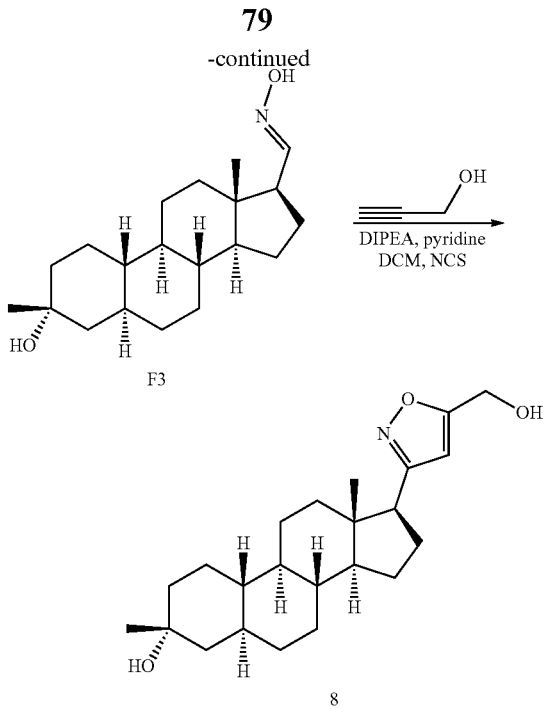

Step 1. Under nitrogen atmosphere, anhydrous THF (400 mL) was cooled to 10° C. and anhydrous LiCl (12.8 g, 304 mmol) was added in one portion. The mixture was stirred for 30 min after which a clear solution was obtained. To this mixture was added anhydrous FeCl₃ (25.7 g, 159 mmol) in one portion. The resulting mixture was stirred for additional 30 min. The reaction mixture was cooled to −35° C. and MeMgBr (3 M in diethyl ether, 193 mL, 580 mmol) was added dropwise maintaining the internal temperature between −35° C. and −30° C. The above mixture was stirred for 30 min at −30° C. F-4 (40 g, 145 mmol) was added in one portion. The internal temperature was allowed to −20° C. and held between −15° C. and −20° C. for 2 hours. The reaction mixture was quenched with aqueous HCl (2 M, 200 mL) and extracted with DCM (2×500 mL). The combined organic layer was washed with aqueous NaOH (10%, 2×300 mL) and brine (300 mL), dried over anhydrous Na₂SO₄, filtered and concentrated. The residue was triturated from EtOAc to give F-5 (25.0 g, 59%) as an off white solid. ¹H NMR (400 MHz, CDCl₃) δ 2.44-2.40 (m, 1H), 2.09-2.00 (m, 1H), 1.89-1.57 (m, 7H), 1.54-1.03 (m, 16H), 0.87 (s, 3H), 0.73-0.70 (m, 2H).

Step 2. To a solution of ethyltriphenylphosphonium bromide (152 g, 412 mmol) in THF (600 mL), was added a solution of t-BuOK (46.1 g, 412 mmol) at 25° C. The mixture was heated to 60° C. and stirred for 1 h and then F-5 (30.0 g, 103 mmol) was added. The mixture was stirred at 60° C. for 2 hrs. The mixture was poured into sat.aq NH₄Cl (500 mL), extracted with EtOAc (2×300 mL). The combined organic phase was washed with brine (300 mL), dried over anhydrous Na₂SO₄, filtered, concentrated. The residue was purified by silica gel column (PE/EtOAc=100/1) to afford F-6 (30 g, 96%) as an off white solid. ¹H NMR (400 MHz, CDCl₃) δ 5.12-5.09 (m, 1H), 2.34-2.21 (m, 3H), 1.86-1.58 (m, 8H), 1.56-0.99 (m, 17H), 0.87 (s, 3H), 0.75-0.68 (m, 2H).

Step 3. To a solution of F-6 (40.0, 132 mmol) in THF (300 mL) was added di-methylsulfide borane (132 mL, 1.32 mol) dropwise at 0° C. The mixture was stirred at 25° C. for 12 hrs. After cooling to 0° C., a solution of NaOH (220 mL, 3M) was added very slowly. After the addition was complete, H₂O₂(150 mL, 33%) was added slowly and the inner temperature was maintained below 10° C. The resulting solution was stirred at 25° C. for 2 hrs. The resulting solution was filtered, and the filtrate was extract with EtOAc (3×500 mL). The combined organic solution was washed with saturated aqueous Na₂S₂O₃ (2×500 mL), brine (500 mL), dried over Na₂SO₄ and concentrated in vacuum to give F-7 (40 g, crude) as a white solid. The crude product was used for the next step without further purification.

Step 4. To a solution of F-7 (40 g, 124 mmol) and silica gel (44 g) in DCM (400 mL) was added pyridinium chlorochromate (53.4 g, 248 mmol) at 25° C. The mixture was stirred at 25° C. for 2 hrs. The mixture was filtered and the filter cake was washed with DCM (2×200 mL). The combined filtrate was concentrated in vacuum. The residue was purified by silica gel column (eluted with PE/EtOAc=10/1 to 1/1) to afford F-8 (34 g, 86%) as an off white solid. ¹H NMR (400 MHz, CDCl₃) δ 2.55-2.51 (m, 1H), 2.20-2.10 (m, 4H), 2.00-1.64 (m, 4H), 1.60-0.99 (m, 20H), 0.75-0.69 (m, 3H), 0.60 (s, 3H).

Step 5. To a solution of F-8 (10.0 g, 31.3 mmol) in dioxane/H₂O (400 mL/120 mL) at 0° C. was added sodium hypobromide (1500 mL) [prepared from NaOH (163 g), dibromine (54.1 mL), dioxane (600 mL) and H₂O (800 mL)]. The resulting mixture was stirred at 25° C. for 24 hours. Sat.aq Na₂S₂O₃ (400 mL) was added followed by adding HCl (450 mL, IM). The mixture was adjusted to pH=6 and a white precipitate appeared. The precipitate was filtered and the filter cake was washed with water (2×300 mL), dried in vacuum to give F-9 (9.5 g, 95%) as a white solid.

¹H NMR (400 MHz, DMSO-d₆) δ 11.89 (br, 1H), 3.87 (s, 1H), 2.29-2.26 (m, 1H), 2.00-1.93 (m, 2H), 1.65-1.15 (m, 9H), 1.13-0.91 (m, 13H), 0.85-0.75 (m, 5H).

Step 6. A mixture of F-9 (12.2 g, 38.0 mmol), N,O-dimethylhydroxylamine hydrochloride (7.41 g, 76.0 mmol), HATU (17.3 g, 45.5 mmol) and Et₃N (21.0 mL, 152 mmol) in 300 mL anhydrous DCM was stirred for 18 hrs at 25° C. The mixture was treated with water (200 mL), extracted with DCM (2×300 mL). The combined organic phase was washed with aqueous HCl (200 mL, IM), saturated aqueous NaHCO₃ (200 mL), brine (300 mL), dried over anhydrous Na₂SO₄, filtered and concentrated in vacuum. The residue was purified by silica gel column (PE/EtOAc=5/1) to afford F-1 (13.0 g, 94%) as an off white solid. 1H NMR (400 MHz, CDCl₃) δ 3.64 (s, 3H), 3.20 (s, 3H), 2.80 (br, 1H), 2.25-2.15 (m, 1H), 1.81-1.57 (m, 8H), 1.33-1.00 (m, 16H), 0.74 (s, 3H), 0.69-0.60 (m, 2H).

Step 7. To a solution of F-1 (200 mg, 550 μmol) in THF (3 mL) was added LiAlH₄ (41.3 mg, 1.09 mmol) at −45° C. The mixture was stirred at 25° C. for 2 hrs. The mixture was quenched with NH₄Cl (20 mL) and extracted with EtOAc (2×30 mL). The combined organic layers were washed with brine (30 mL), dried over Na₂SO₄ and concentrated in vacuum to give F-2 (180 mg, crude) as an off-white solid.

Step 8. To a solution of F-2 (180 mg, 591 μmol) in DCM (3 mL) was added triethylamine (0.326 mL, 2.36 mmol) and hydroxylamine hydrochloride (61.5 mg, 886 mmol) at 25° C. The mixture was stirred at 25° C. for 12 hrs. The mixture was poured into water (50 mL) and extracted with DCM (2×30 mL). The combined organic layers were washed with brine (30 mL), dried over Na₂SO₄ and concentrated in vacuum to give F-3 (200 mg, crude) as an off-white solid.

Step 10. A solution of F-3 (200 mg, μmol) in DCM (3 mL) was added pyridine (0.1 mL) and 1-chloropyrrolidine-2,5-dione (83.2 mg, 626 μmol) at 25° C. The mixture was stirred at 25° C. for 1 h. The reaction was treated with prop-2-yn-1-ol (104 mg, 1.87 mmol), followed by DIEA (0.1 mL). After stirring for 3 hrs, the reaction was concentrated in vacuum. The residue was purified by preparative HPLC separation (column: Phenomenex Synergi C18 150*30 mm*4 um, gradient: 52-82% B (A=0.05% HCl-ACN, B=acetonitrile), flow rate: 30 mL/min) to obtain 8 (28 mg, 12%) as an off-white solid.

1H NMR (CDCl$_3$, 400 MHz): δ 6.10 (s, 1H), 4.74 (s, 2H), 2.72 (t, J=9.8 Hz, 1H), 2.21-1.88 (m, 3H), 1.82-1.73 (m, 4H), 1.72-1.62 (m, 3H), 1.54 (d, J=2.8 Hz, 2H), 1.39-1.23 (m, 5H), 1.20 (s, 3H), 1.16-0.93 (m, 6H), 0.80-0.65 (m, 2H), 0.58 (s, 3H).

LCMS R$_t$=0.984 min in 2 min chromatography, 30-90AB, MS ESI calcd. for C$_{23}$H$_{36}$NO$_3$ [M+H]$^+$ 374, found 374.

Example 7. Synthesis of Compound 9. PP-85,C3

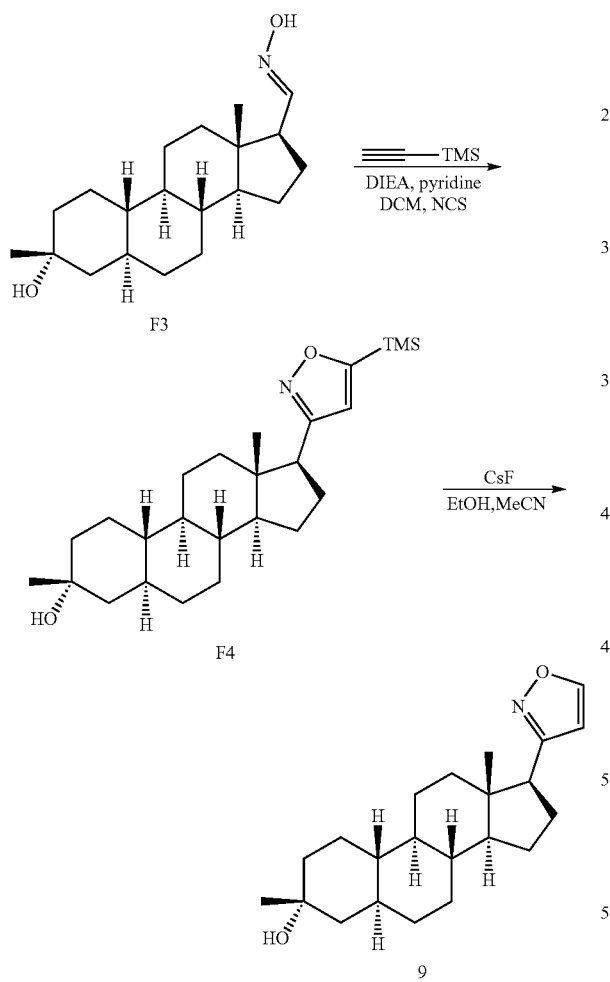

Step 1. To a solution of F-3 (300 mg, 0.939 mmol) in DCM (5 mL) was added pyridine (0.3 mL) and 1-chloropyrrolidine-2,5-dione (125 mg, 0.939 mmol) at 25° C. The mixture was stirred at 25° C. for 1 h. The reaction was treated with ethynyltrimethylsilane (275 mg, 2.81 mmol), followed by DIEA (0.3 mL). After stirring 2 hrs at 25° C., the reaction was poured into water (50 mL) and extracted with DCM (2×15 mL). The combined organic layers were washed with brine (30 mL), dried over Na$_2$SO$_4$ and concentrated in vacuum to give F-4 (250 mg, crude) as a light yellow solid.

Step 2. To a mixture of F-4 (250 mg, 601 μmol) in acetonitrile (6 mL) and EtOH (3 mL) was added CsF (100 mg, 661 μmol) at 25° C. The mixture was stirred at 25° C. for 2 hrs. The reaction was poured into water (30 mL) and extracted with DCM (2×30 mL). The combined organic layer was washed with brine (50 mL), dried over anhydrous Na$_2$SO$_4$, filtered and concentrated to afford the crude product. The residue was purified by preparative HPLC (column: Phenomenex Synergi C18 150*30 mm*4 um, gradient: 65-95% B (A=0.05% HCl-ACN, B=acetonitrile), flow rate: 30 mL/min) to afford 9 (42.1 mg, 20%) as an off-white solid.

1H NMR (CDCl$_3$, 400 MHz): δ 8.33 (s, 1H), 6.21 (d, J=1.4 Hz, 1H), 2.79 (t, J=9.8 Hz, 1H), 2.21-2.20 (m, 3H), 1.87-1.75 (m, 4H), 1.75-1.66 (m, 2H), 1.64-1.58 (m, 2H), 1.40-1.27 (m, 5H), 1.23 (s, 3H), 1.19-1.10 (m, 6H), 0.81-0.65 (m, 2H), 0.59 (s, 3H).

LCMS Rt=2.071 min in 3 min chromatography, 30-90AB, MS ESI calcd. for C$_{22}$H$_{34}$NO$_2$ [M+H]$^+$ 344.25, found 344.2.

Example 8. Synthesis of Compound 10

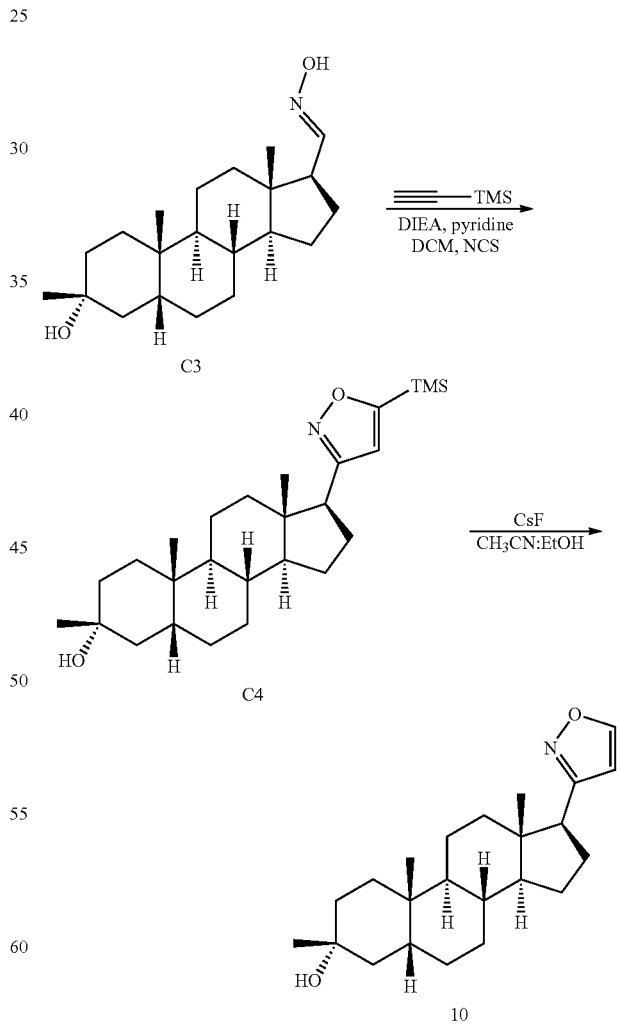

Step 1. To a solution of C-3 (260 mg, 0.779 mmol) in DCM (5 mL) was added pyridine (0.3 mL) and 1-chloropyrrolidine-2,5-dione (104 mg, 0.779 mmol) at 25° C. The mixture was stirred at 25° C. for 1 h. The reaction was treated with ethynyltrimethylsilane (228 mg, 2.33 mmol), followed by DIEA (0.3 mL). After stirring 2 hrs at 25° C., the reaction was poured into water (50 mL) and extracted with DCM (2×15 mL). The combined organic layers were washed with brine (30 mL), dried over $Na_2SO_4$ and concentrated in vacuum to give C-4 (250 mg, crude) as a light yellow solid.

Step 2. To a mixture of C-4 (250 mg, 581 μmol) in acetonitrile (6 mL) and EtOH (3 mL) was added CsF (97 mg, 639 μmol) at 25° C. The mixture was stirred at 25° C. for 2 hrs. The reaction was poured into water (30 mL) and extracted with DCM (2×30 mL). The combined organic layer was washed with brine (50 mL), dried over anhydrous $Na_2SO_4$, filtered and concentrated to afford crude product. The residue was purified by preparative HPLC (column: Phenomenex Synergi C18 150*30 μm*4 um, gradient: 65-95% B (A=0.05% HCl-ACN, B=acetonitrile), flow rate: 30 mL/min) to afford 10 (15.1 mg, 7%) as an off-white solid.

1H NMR (400 MHz, $CDCl_3$): δ 8.34 (s, 1H), 6.20 (d, J=1.4 Hz, 1H), 2.78 (t, J=9.8 Hz, 1H), 2.23-1.73 (m, 8H), 1.55-1.40 (m, 7H), 1.39-1.14 (m, 10H), 1.08 (td, J=14.4, 3.5 Hz, 1H), 0.97 (s, 3H), 0.56 (s, 3H).

LCMS $R_t$=1.980 min in 3 min chromatography, 30-90AB, MS ESI calcd. for $C_{23}H_{36}NO_2$ [M+H]+ 358.27, found 358.3.

Example 9. Synthesis of Compound 11

Step 1. To a solution of E-5 (CAS 162882-77-1; 0.4 g, 1.25 mmol) in ethyl formate (10 mL) was added NaOMe (337 mg, 6.25 mmol). The mixture was stirred at 15° C. for 30 mins. The mixture was heated at 50° C. for 16 hrs. The reaction solution was concentrated to give a residue (400 mg, crude), which was used in next step directly.

Step 2. To a solution of D-15 (0.4 g, 1.15 mmol) in EtOH (5 mL) and $H_2O$ (2 mL) was added $NH_2OH \cdot HCl$ (240 mg, 3.44 mmol) and AcOH (2 mL). The reaction solution was stirred at 15° C. for 10 mins and was stirred at 80° C. for 16 hrs. The mixture was concentrated to give a residue, which was purified by preparative HPLC to give 11 (107 mg, 27%) as an off-white solid.

$^1$H NMR (400 MHz, $CDCl_3$) δ 8.14 (s, 1H), 5.96 (s, 1H), 2.84-2.79 (m, 1H), 2.10-0.85 (m, 27H), 0.52 (s, 3H).

LCMS Rt=1.355 min in 2 min chromatography, 10-80AB, MS ESI calcd. for $C_{22}H_{32}NO$ $[M+H-H_2O]^+$ 326, found 326.

Example 10. Synthesis of Compound 12

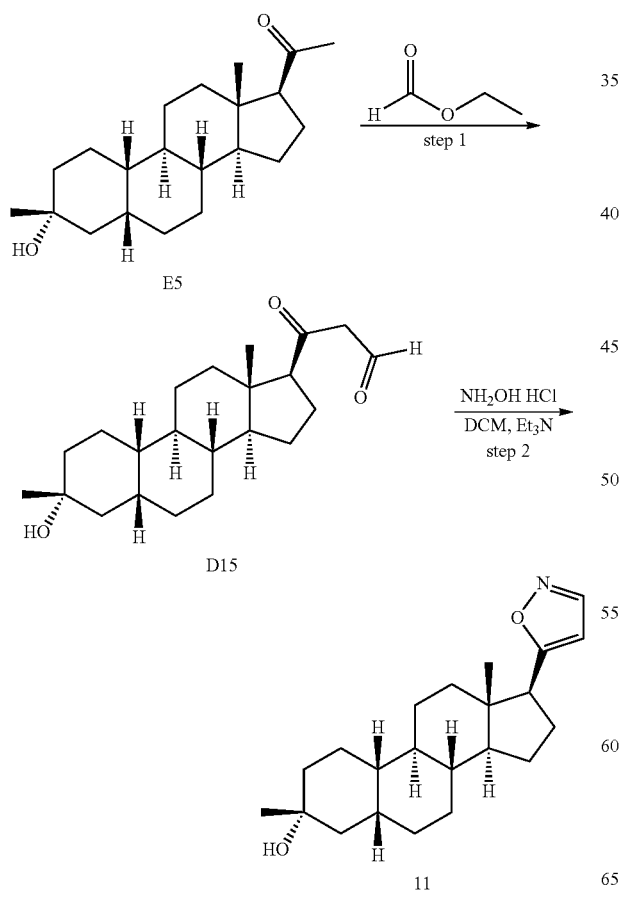

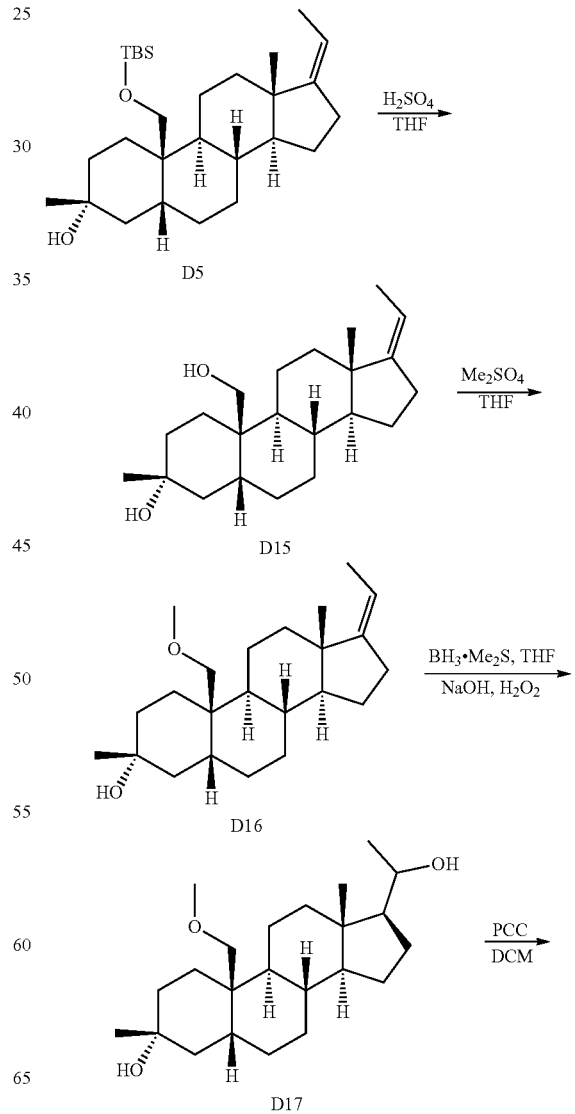

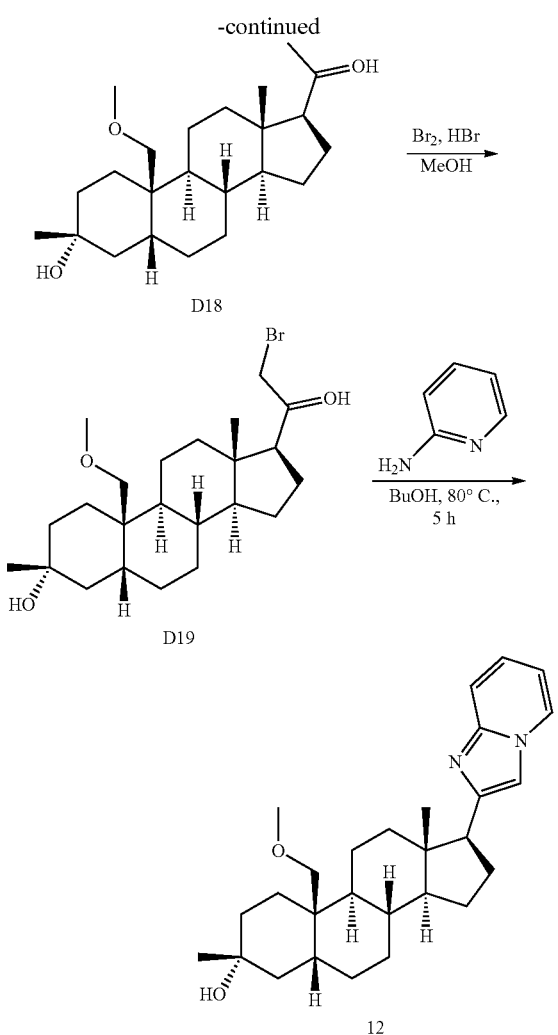

Step 1. To a solution of D-5 (16 g, 35.8 mmol) in THF (150 mL) was added aqueous sulfuric acid (2 M, 71.5 mL, 143 mmol). The mixture was stirred at 15° C. for 48 hrs. The reaction mixture was neutralized with aqueous sodium bicarbonate (250 mL), extracted with EtOAc (2×200 mL). The combined organic layers were washed with brine (200 mL), dried over anhydrous sodium sulfate, filtered and concentrated. The residue was purified by column chromatography on silica gel (PE:EtOAc=3:1) to give D-15 (9.5 g, 80%) as an off-white solid. $^1$H NMR (400 MHz, CDCl$_3$) δ 5.14-5.07 (m, 1H), 3.92 (d, J=10.8 Hz, 1H), 3.54 (d, J=10.4 Hz, 1H), 2.39-2.23 (m, 3H), 1.96-1.85 (m, 2H), 1.83-1.72 (m, 1H), 1.66-1.57 (m, 5H), 1.54-1.36 (m, 8H), 1.34-1.13 (m, 11H), 0.84 (s, 3H).

Step 2. To a solution of D-15 (5.0 g, 15.0 mmol) in THF (50 mL) was added NaH (1.80 g, 45.0 mmol, 60%) at 0° C. and stirred for 30 mins. Me$_2$SO$_4$ (1.87 g, 14.8 mmol) was added and the reaction mixture was stirred at 15° C. for 12 hrs. The reaction mixture was quenched with saturated aqueous NH$_4$Cl (100 mL) and extracted with EtOAc (2×100 mL). The combined organic phase was washed with brine (100 mL), dried over anhydrous Na$_2$SO$_4$, concentrated in vacuum. The residue was purified by column chromatography on silica gel (PE/EtOAc=20/1) to afford D-16 (3.2 g, 62%) as an off-white solid.

$^1$H NMR (400 MHz, CDCl$_3$) δ 5.11-5.07 (m, 1H), 3.57 (d, J=9.2 Hz, 1H), 3.33 (s, 3H), 3.19 (d, J=9.2 Hz, 1H), 2.32-2.22 (m, 3H), 1.92-1.51 (m, 12H), 1.47-1.19 (m, 14H), 0.85 (s, 3H).

Step 3. To a solution of D-16 (3.2 g, 9.23 mmol) in THF (50 mL) was added dropwise BH$_3$.Me$_2$S (9.22 mL, 92.3 mmol) at 0° C. The solution was stirred at 15° C. for 12 hrs. After cooling to 0° C., a solution of NaOH (40 mL) was added very slowly. After the addition was complete, H$_2$O$_2$ (30 mL, 33%) was added slowly and the inner temperature was maintained below 15° C. The resulting solution was stirred at 15° C. for 3 hrs. The reaction mixture was quenched with citric acid (20 mL, 1M) and the mixture was extracted with EtOAc (3×100 mL). The combined organic solution was washed with saturated aqueous Na$_2$S$_2$O$_3$ (50 mL), brine (150 mL), dried over Na$_2$SO$_4$ and concentrated in vacuum to give the crude product, which was purified by column chromatography on silica gel (PE: EtOAc=10/1) to afford crude D-17 (2.0 g, 60%) as an off-white solid.

Step 4. To a solution of D-17 (2.0 g, 5.48 mmol) in DCM (30 mL) was added PCC (2.34 g, 10.9 mmol) at 15° C. The mixture was stirred at 15° C. for 1 h and the reaction mixture was filtered and the filtrate was concentrated in vacuum. The residue was purified by column chromatography on silica gel (PE/EtOAc=10/1) to afford D-18 (1.8 g, 91%) as light yellow solid.

$^1$H NMR (400 MHz, CDCl$_3$) δ 3.54 (d, J=9.2 Hz, 1H), 3.33 (s, 3H), 3.18 (d, J=9.2 Hz, 1H), 2.54-2.52 (m, 1H), 2.13-1.91 (m, 7H), 1.66-1.27 (m, 13H), 1.25-1.18 (m, 9H), 0.59 (s, 3H).

Step 5. To a stirred solution of D-18 (500 mg, 1.37 mmol) in MeOH (5 mL) was added HBr (68.3 mg, 411 μmol, 48%), then Br$_2$ (100 L, 2.05 mmol) was added dropwise. The mixture was stirred at 15° C. for 5 hrs. The mixture was quenched by a saturated aqueous NaHCO$_3$ and adjusted to pH=7, extracted with DCM (2×20 mL). The combined organic phase was concentrated in vacuum to give D-19 (650 mg) as light yellow solid.

$^1$H NMR (400 MHz, CDCl$_3$) δ 3.90-3.89 (m, 2H), 3.53 (d, J=9.2 Hz, 1H), 3.32 (s, 3H), 3.18 (d, J=9.2 Hz, 1H), 2.82-2.81 (m, 1H), 2.18-2.15 (m, 1H), 1.92-1.23 (m, 25H), 0.62 (s, 3H).

Step 6. To a solution of D-19 (100 mg, 226 μmol) in t-BuOH (3 mL) was added pyridin-2-amine (25.5 mg, 271 umol) and K$_2$CO$_3$ (62.4 mg, 452 umol) at 15° C. The mixture was stirred at 80° C. for 5 hrs. The reaction mixture was extracted with EtOAc (2×30 mL). The combined organic phase was concentrated to give the crude product, which was purified by preparative HPLC to afford 12 (21.5 mg, 22%) as an off-white solid.

$^1$H NMR (400 MHz, CDCl$_3$) δ 8.06 (d, J=6.8 Hz, 1H), 7.65 (br, 1H), 7.35 (s, 1H), 7.16 (br, 1H), 6.77 (br, 1H), 3.59 (d, J=8.8 Hz, 1H), 3.33 (s, 3H), 3.16 (d, J=9.2 Hz, 1H), 2.86-2.84 (m, 1H), 2.16-2.10 (m, 1H), 1.96-1.55 (m, 8H), 1.53-1.20 (m, 17H), 0.53 (s, 3H).

LCMS Rt=0.760 min in 1.5 min chromatography, 5-95 AB, MS ESI calcd. for C$_{28}$H$_{41}$N$_2$O$_2$ [M+H]$^+$ 437, found 437.

Example 11. Synthesis of Compound 13

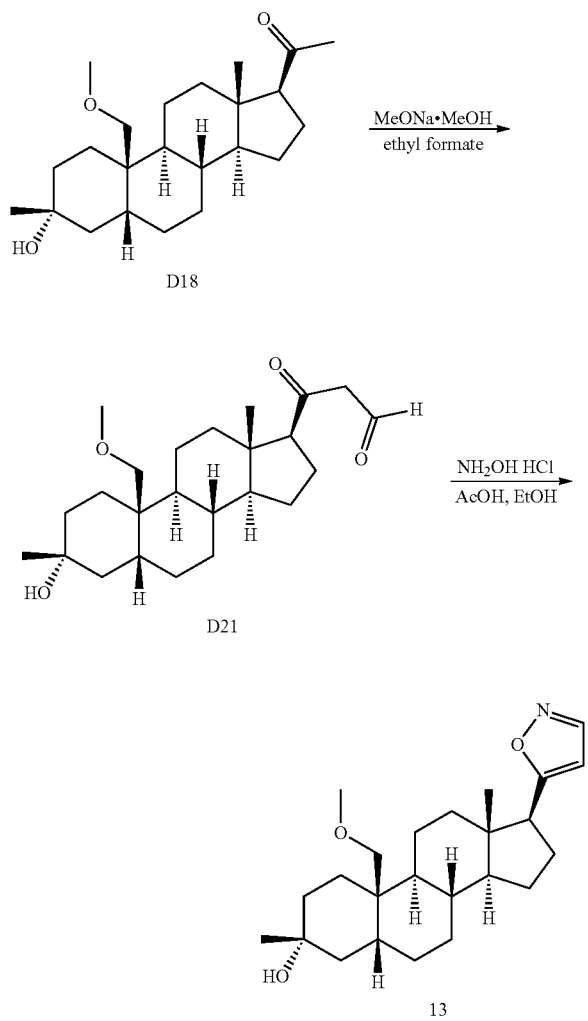

Example 12. Synthesis of Compound 14

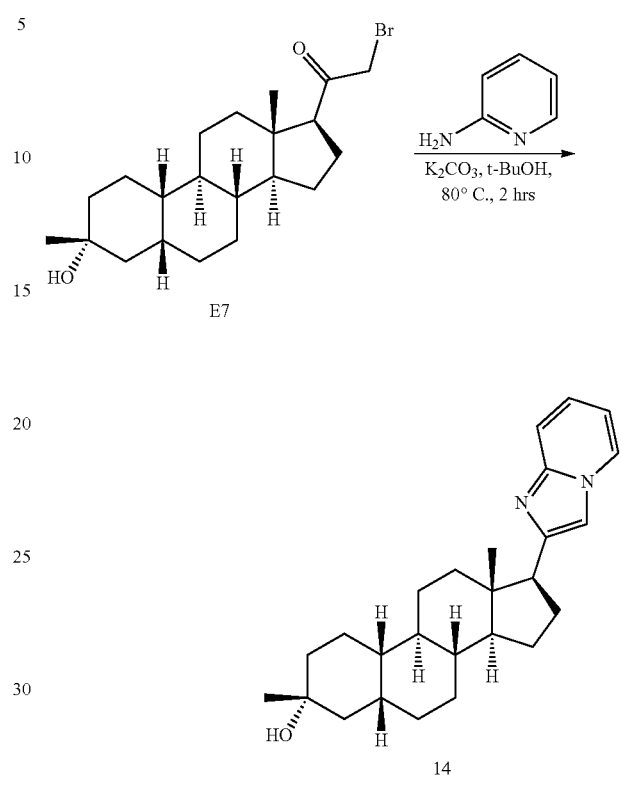

Step 1. To a suspension of D-18 (100 mg, 275 μmol) in ethyl formate (5 mL) was added NaOMe.MeOH (5 mL, 25%) at 15° C. The reaction was stirred at 50° C. for 12 hrs. The reaction mixture was concentrated to get the crude product D-21 (300 mg, crude) as yellow solid, which was used directly in next step without further purification.

Step 2. To a suspension of D-21 (100 mg, 256 μmol) and hydroxylamine hydrochloride (21.3 mg, 307 umol) in EtOH (5 mL) was added AcOH (2 mL), followed by water (10 mL) at 15° C. The resulting mixture was stirred at 80° C. for 4 hrs. The reaction mixture was concentrated to remove EtOH. The mixture was extracted with EtOAc (2×50 mL). The combined organic phase was washed with brine (50 ml) and concentrated in vacuum. The residue was purified by preparative HPLC to afford 13 (102.7 mg, 50% over two steps) as an off-white solid.

$^1$H NMR (400 MHz, CDCl$_3$) δ 8.14 (d, J=1.2 Hz, 1H), 5.96 (s, 1H), 3.56 (d, J=9.2 Hz, 1H), 3.31 (s, 3H), 3.16 (d, J=8.8 Hz, 1H), 2.81-2.77 (m, 1H), 2.01-1.91 (m, 5H), 1.85-1.19 (m, 21H), 0.49 (s, 3H).

LCMS Rt=0.914 min in 1.5 min chromatography, 5-95 AB, MS ESI calcd. for $_2C_{24}H_{36}NO_2$ [M+H−H$_2$O]$^+$370, found 370.

To a solution of E-7 (CAS 1430063-93-6; 100 mg, 251 μmol) in t-BuOH (5 mL) was added pyridin-2-amine (23.6 mg, 251 μmol) and K$_2$CO$_3$ (69.2 mg, 502 μmol) at 15° C. The mixture was stirred at 80° C. for 4 hrs. The mixture was diluted by DCM (15 mL) and filtered. The filtrate was concentrated to give the crude product, which was purified by preparative HPLC to afford 14 (25.3 mg, 26%).

$^1$H NMR (400 MHz, CDCl$_3$) 16.02 (br. s., 1H), 8.45 (d, J=7.8 Hz, 1H), 8.30 (br. s., 1H), 7.70 (br. s., 1H), 7.48 (br. s., 1H), 7.34-7.28 (m, 1H), 3.05 (br. s., 1H), 2.21 (br. s., 2H), 1.92-0.90 (m, 24H), 0.70-0.59 (m, 3H)

LCMS Rt=1.507 min in 3 min chromatography, 10-80AB, MS ESI calcd. for C$_{26}$H$_{37}$N$_2$O [M+H]$^+$ 393, found 393.

Example 13. Synthesis of Compound 15

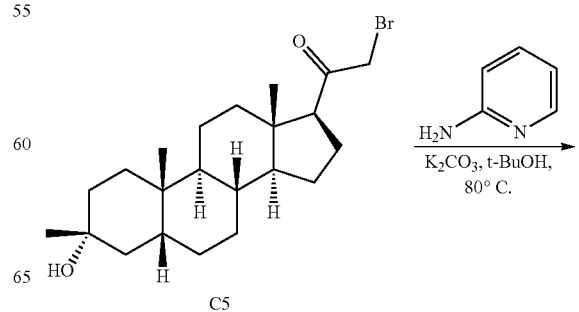

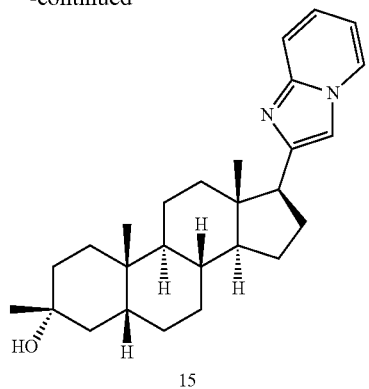

15

To a solution of C-5 (100 mg, 243 μmol) in t-BuOH (5 mL) was added pyridin-2-amine (22.8 mg, 243 μmol) and K₂CO₃ (67.0 mg, 486 μmol) at 15° C. The mixture was stirred at 80° C. for 4 hrs. The mixture was diluted by DCM (15 mL) and filtered. The filtrate was concentrated to get the crude product, which was purified by preparative HPLC to afford 15 (16.7 mg, 17%).

¹H NMR (400 MHz, CDCl₃) δ 16.14 (br. s., 1H), 8.44 (d, J=8.28 Hz, 1H), 8.29 (br. s., 1H), 7.70 (br. s., 1H), 7.47 (br. s., 1H), 3.04 (t, J=9.03 Hz, 1H), 2.20 (br. s., 2H), 1.99-1.82 (m, 5H), 1.81-1.42 (m, 12H), 1.25 (s, 3H), 1.24-1.01 (m, 2H), 0.93 (s, 3H), 6.64 (s, 3H). —LCMS Rt=1.542 min in 3 min chromatography, 10-80AB, MS ESI calcd. for C₂₇H₃₉N₂O [M+H]⁺ 407 found 407.

Example 14. Synthesis of Compound 16

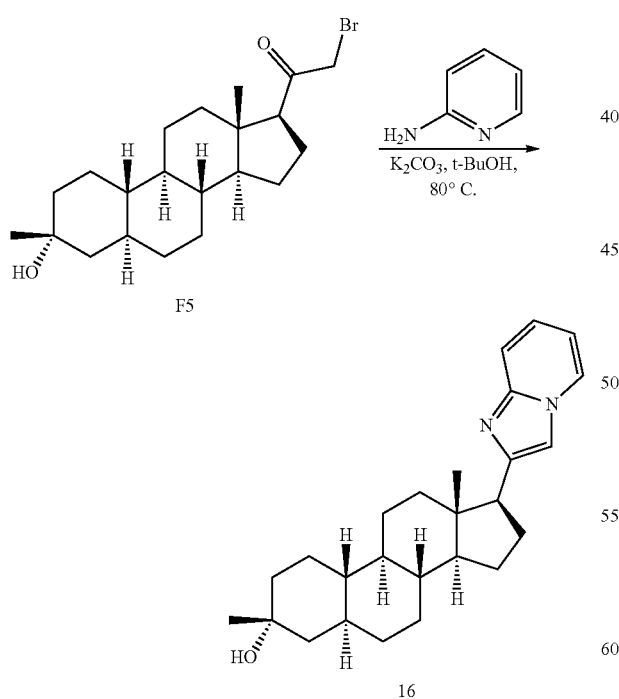

To a solution of F-5 (CAS 1430063-60-7; 150 mg, 377 μmol) in t-BuOH (5 mL) was added pyridin-2-amine (35.4 mg, 377 μmol) and K₂CO₃ (104 mg, 754 μmol) at 15° C. The mixture was stirred at 80° C. for 4 h. The mixture was diluted with DCM (15 mL), filtered. The filtrate was concentrated to afford the crude product, which was purified by preparative HPLC to give 16 (46.2 mg, yield 31%).

¹H NMR (400 MHz, CDCl₃) δ 16.05 (br. s., 1H), 8.40-8.35 (m, 2H), 7.69 (br s, 1H), 7.70 (br s, 1H), 7.52 (br s, 1H), 7.26 (br s under chloroform peak, 1H), 3.05-3.04 (m, 1H), 2.30-2.20 (m, 2H), 1.67-0.68 (multiple m, apparent 26H), 0.65 (m and s, 4H).LCMS Rt=1.511 min in 3 min chromatography, 10-80AB, MS ESI calcd. for C₂₆H₃₇N₂O [M+H]⁺ 393, found 393.

Example 15. Synthesis of Compound 17

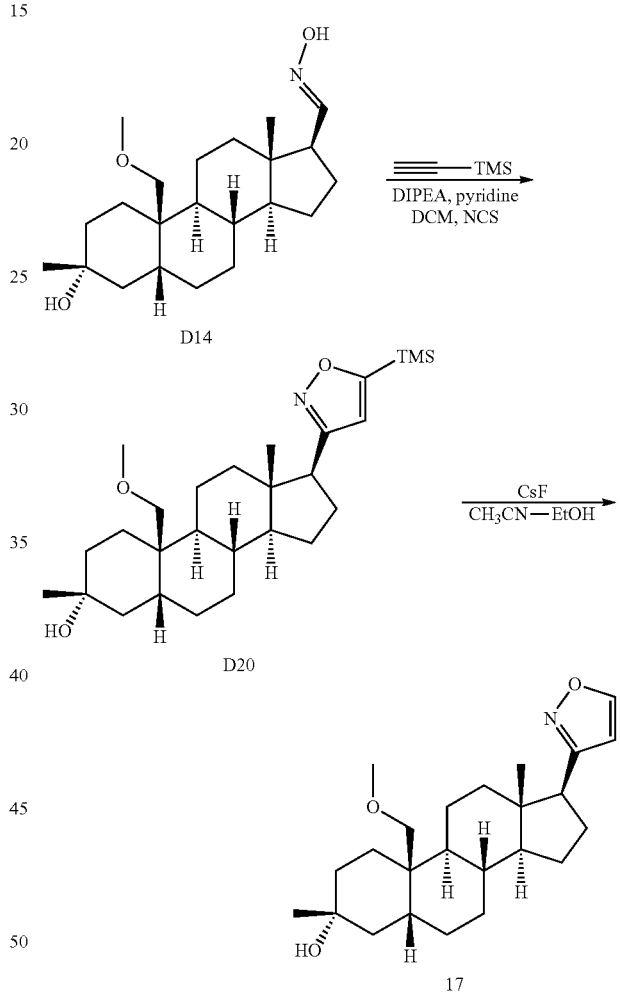

Step 1. To a solution of D-14 (250 mg, 0.69 mmol) in anhydrous DCM (3 mL) was added pyridine (53 mg, 0.69 mmol) and NCS (91 mg, 0.69 mmol) at 15° C. The mixture was stirred at 15° C. for 1.5 hrs. DIEA (89 mg, 0.69 mmol) and ethynyltrimethylsilane (202 mg, 2.06 mmol) was added. The mixture was stirred at 15° C. for 15 hrs. Water (10 mL) was added and the mixture was extracted with EtOAc (3×20 mL). The combined organic layers were washed with brine (3×10 mL), dried over anhydrous Na₂SO₄, filtered and concentrated. The residue was purified by column chromatography on silica gel (PE:EtOAc=1:1) to give D-15 (130 mg, impure) as an off-white solid.

Step 2. To a solution of D-20 (130 mg, 0.28 mmol) in anhydrous MeCN (2 mL) and EtOH (1 mL) was added CsF (47 mg, 0.31 mmol) at 15° C. The mixture was stirred at 15° C. for 15 hrs. Water (10 mL) was added and the mixture was extracted with EtOAc (3×20 mL). The combined organic layers were washed with saturated brine (3×10 mL), dried over anhydrous $Na_2SO_4$, filtered and concentrated. The residue was purified by preparative HPLC (0.5% $NH_4HCO_3$ additive) to give 17 (36 mg, 33%) as an off-white solid.

$^1$H NMR (400 MHz, $CDCl_3$) δ 8.32 (d, J=1.5 Hz, 1H), 6.18 (d, J=1.8 Hz, 1H), 3.57 (d, J=9.3 Hz, 1H), 3.33 (s, 3H), 3.23-3.13 (m, 1H), 2.76 (t, J=9.8 Hz, 1H), 2.22-1.88 (m, 4H), 1.85-1.70 (m, 3H), 1.67-1.40 (m, 9H), 1.35-1.07 (m, 10H), 0.54 (s, 3H).

LCMS Rt=0.914 min in 1.5 min chromatography, 5-95 AB, purity 97%, MS ESI calcd. for $C_{24}H_{36}NO_2$ $[M+H-H_2O]^+$ 370, found 370.

Example 16. Synthesis of Compound 18

Step 2. To a solution of C-8 (600 mg, 1.66 mmol) in EtOH (20 mL) and $H_2O$ (2 mL) was added hydroxylamine hydrochloride (345 mg, 4.97 mmol) and AcOH (3 mL). The reaction solution was stirred at 15° C. for 1 h and then stirred at 80° C. for 16 hrs. The mixture was concentrated to give a residue, which was purified by preparative HPLC and then purified by SFC to give 18 (17 mg, 3%) as an off-white solid.

$^1$H NMR (400 MHz, $CDCl_3$) δ 8.14 (d, J=1.5 Hz, 1H), 6.00-5.90 (m, 1H), 2.80 (t, J=9.8 Hz, 1H), 2.16-0.76 (m, 29H), 0.50 (s, 3H).

LCMS Rt=0.979 min in 1.5 min chromatography, 5-95AB, MS ESI calcd. for $C_{23}H_{34}NO$ $[M+H-H_2O]^+$ 340, found 340.

Example 17. Synthesis of Compound 19

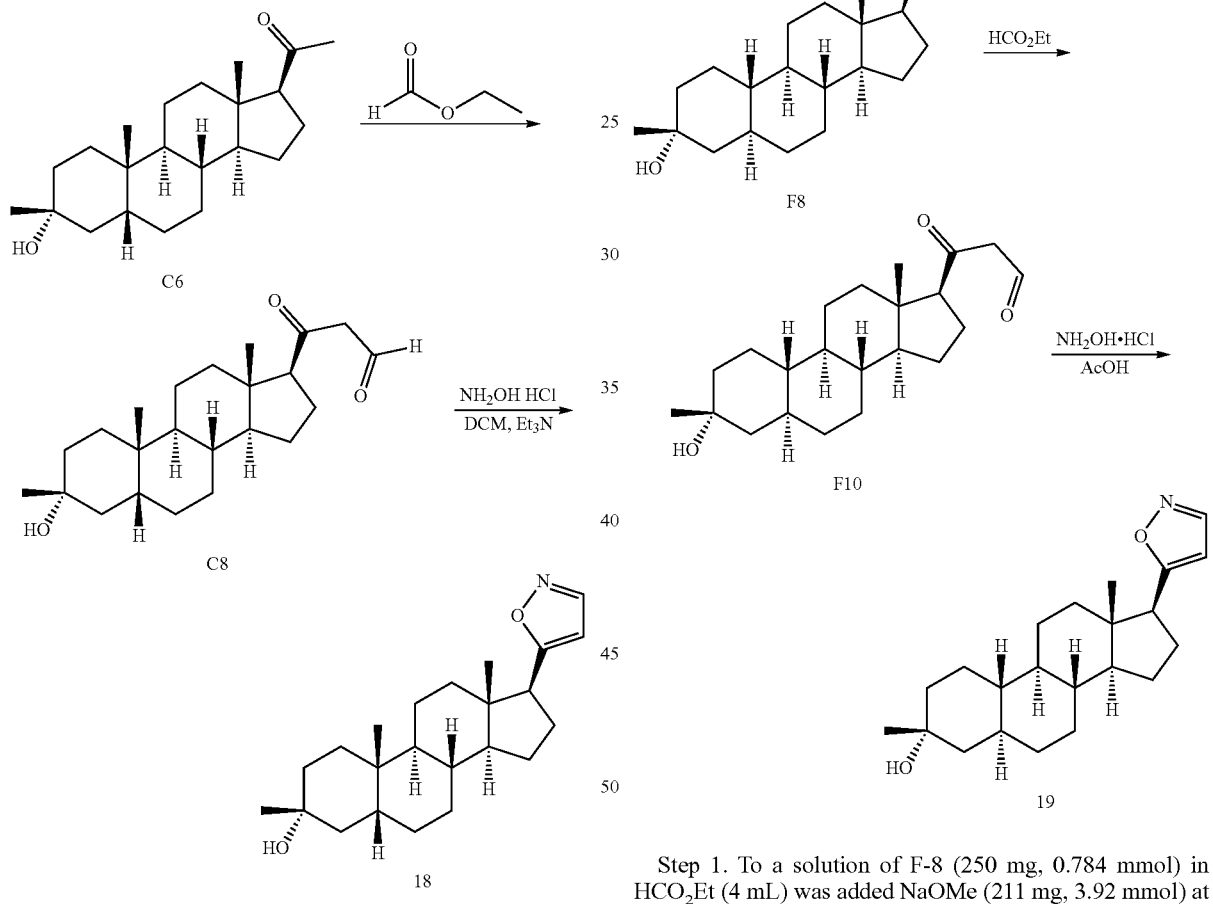

Step 1. To a solution of C-6 (580 mg, 1.74 mmol) in ethyl formate (50 mL, 618 mmol) was added $CH_3ONa$ (282 mg, 5.22 mmol) at 25° C. The reaction was stirred at 25° C. for 16 hrs. The reaction solution was concentrated in vacuum and the residue was added ethyl formate (20 mL, 247.2 mmol) and $CH_3ONa$ (640 mg, 11.85 mmol) at 25° C. The reaction was stirred at 60° C. for 16 hrs. The reaction solution was concentrated in vacuum to give crude C-8 (600 mg, crude), which was used for next step directly without further purification.

LCMS Rt=1.278 min in 2 min chromatography, 10-80AB, MS ESI calcd. For $C_{23}H_{37}O_3$ $[M+H]^+$ 361, found 361.

Step 1. To a solution of F-8 (250 mg, 0.784 mmol) in $HCO_2Et$ (4 mL) was added NaOMe (211 mg, 3.92 mmol) at 50° C. The mixture was stirred at 25° C. for 12 hrs. The reaction mixture was concentrated to get the crude product F-10 (800 mg, crude) as yellow solid, which was used directly in next step without further purification.

Step 2. To a suspension of F-10 (800 mg, 2.30 mmol) and hydroxylamine hydrochloride (175 mg, 2.53 mmol) in EtOH (2 mL) was added AcOH (5 mL), followed by water (8 mL). The resulting mixture was stirred at 80° C. for 4 hrs. The reaction mixture was concentrated to give an off-white solid, which was purified by preparative HPLC to afford 19 (60 mg, 8%) as an off-white solid.

$^1$H NMR (400 MHz, $CDCl_3$) δ 8.14 (s, 1H), 5.96 (s, 1H), 2.80 (t, J=8.8 Hz, 1H), 2.06-2.01 (m, 2H), 2.06-2.01 (m,

2H), 1.95-1.90 (m, 1H), 1.80-1.75 (m, 4H), 1.70-1.50 (m, 5H), 1.41-1.29 (m, 4H), 1.28-1.01 (m, 7H), 0.71-0.68 (m, 2H), 0.53 (s, 3H).

LCMS $R_t$=1.350 min in 2 min chromatography, 10-80 AB, MS ESI calcd. For $C_{22}H_{34}NO_2$ [M+H]$^+$ 344, found 344.

Example 18. Synthesis of Compound 20

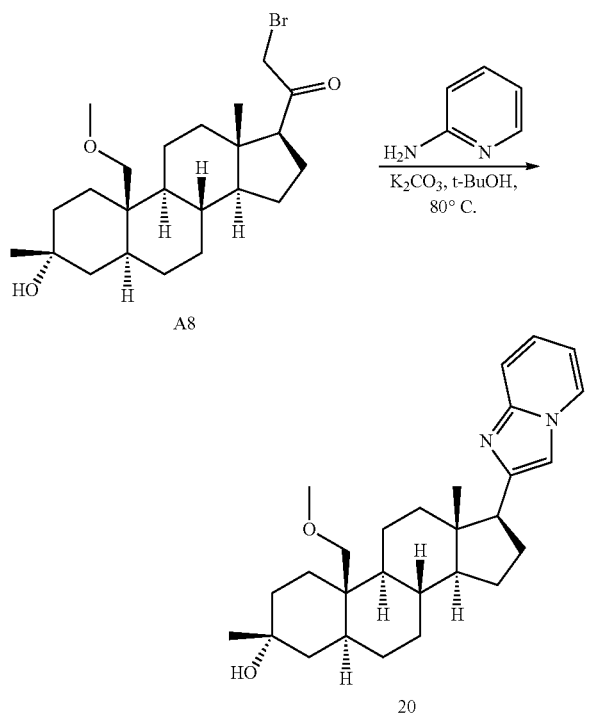

To a solution of A-8 (300 mg, 679 μmol) in t-BuOH (5 mL) was added pyridin-2-amine (63.9 mg, 679 μmol) and $K_2CO_3$ (186 mg, 1.35 mmol) at 15° C. The mixture was stirred at 80° C. for 4 hrs. The mixture was diluted by DCM (20 mL) and filtered, the filtrate was concentrated to get the crude product, which was purified by preparative HPLC to afford 20 (26 mg, 8%).

$^1$H NMR (400 MHz, CDCl$_3$) δ ppm 8.05 (d, J=6.52 Hz, 1H), 7.61 (br. s., 1H), 7.35 (s, 1H), 7.12 (br. s., 1H), 6.74 (br. s., 1H), 3.50-3.44 (m, 1H), 3.41-3.35 (m, 1H), 3.26 (s, 3H), 2.86 (t, J=9.79 Hz, 1H), 2.25-1.99 (m, 4H), 1.90-0.82 (m, 22H), 0.57 (s, 3H).

LCMS Rt=1.518 min in 3 min chromatography, 10-80AB, MS ESI calcd. for $C_{28}H_{41}N_2O_2$ [M+H]$^+$ 437, found 437.

Assay Methods

Compounds provided herein can be evaluated using various assays; examples of which are described below.

Steroid Inhibition of TBPS Binding

TBPS binding assays using rat brain cortical membranes in the presence of 5 μM GABA has been described (Gee et al, J. Pharmacol. Exp. Ther. 1987, 241, 346-353; Hawkinson et al, *Mol. Pharmacol.* 1994, 46, 977-985; Lewin, A. H et al., *Mol. Pharmacol.* 1989, 35, 189-194).

Briefly, cortices are rapidly removed following decapitation of carbon dioxide-anesthetized Sprague-Dawley rats (200-250 g). The cortices are homogenized in 10 volumes of ice-cold 0.32 M sucrose using a glass/teflon homogenizer and centrifuged at 1500×g for 10 min at 4° C. The resultant supernatants are centrifuged at 10,000×g for 20 min at 4° C. to obtain the P2 pellets. The P2 pellets are resuspended in 200 mM NaCl/50 mM Na—K phosphate pH 7.4 buffer and centrifuged at 10,000×g for 10 min at 4° C. This washing procedure is repeated twice and the pellets are resuspended in 10 volumes of buffer. Aliquots (100 μL) of the membrane suspensions are incubated with 3 nM [$^{35}$S]-TBPS and 5 μL aliquots of test drug dissolved in dimethyl sulfoxide (DMSO) (final 0.5%) in the presence of 5 μM GABA. The incubation is brought to a final volume of 1.0 mL with buffer. Nonspecific binding is determined in the presence of 2 μM unlabeled TBPS and ranged from 15 to 25%. Following a 90 min incubation at room temp, the assays are terminated by filtration through glass fiber filters (Schleicher and Schuell No. 32) using a cell harvester (Brandel) and rinsed three times with ice-cold buffer. Filter bound radioactivity is measured by liquid scintillation spectrometry. Non-linear curve fitting of the overall data for each drug averaged for each concentration is done using Prism (GraphPad). The data are fit to a partial instead of a full inhibition model if the sum of squares is significantly lower by F-test. Similarly, the data are fit to a two component instead of a one component inhibition model if the sum of squares is significantly lower by F-test. The concentration of test compound producing 50% inhibition (IC$_{50}$) of specific binding and the maximal extent of inhibition (I$_{max}$) are determined for the individual experiments with the same model used for the overall data and then the means±SEM.s of the individual experiments are calculated. Picrotoxin serves as the positive control for these studies as it has been demonstrated to robustly inhibit TBPS binding.

Various compounds are or can be screened to determine their potential as modulators of [$^{35}$S]-TBPS binding in vitro. These assays are or can be performed in accordance with the above discussed procedures.

For Table 1, "A" indicates an IC$_{50}$<20 nM, "B" indicates an IC$_{50}$ of 20 nM to 200 nM, "C" indicates an IC$_{50}$>200 nM to 500 nM, and "D" indicates IC$_{50}$>500 nM.

TABLE 1

| Compound | 35S-TBPS Radioligand Displacement (IC50) |
|---|---|
| 1 | B |
| 2 | A |
| 3 | C |
| 4 | B |
| 5 | B |
| 6 | B |
| 7 | B |
| 8 | C |
| 9 | C |
| 10 | B |
| 11 | B |
| 12 | D |
| 13 | B |
| 14 | D |
| 15 | D |
| 16 | D |
| 17 | B |
| 18 | B |
| 19 | D |
| 20 | D |

What is claimed is:

1. A compound of Formula (I-c):

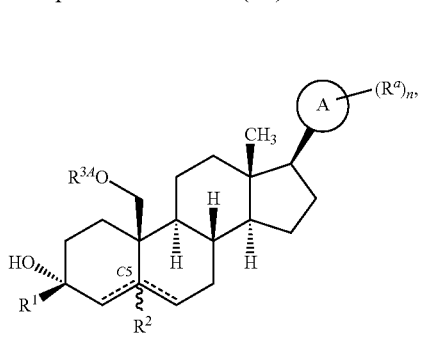
(I-c)

wherein:

n is 0, 1, 2, 3, 4, or 5;

Ring A is aryl or heteroaryl;

$R^{3A}$ is $C_{1-6}$ alkyl;

$R^1$ is hydrogen, $C_{1-3}$ alkyl, $C_{2-6}$ alkenyl, or $C_{3-6}$ carbocyclyl;

$R^2$ is absent or hydrogen;

$R^a$ is halogen, $C_1$-$C_6$ alkyl, $C_2$-$C_6$ alkenyl, $C_2$-$C_6$ alkynyl, carbocyclyl, heterocyclyl, aryl, heteroaryl, —C(O)$R^A$, —C(O)O$R^A$, —C(O)N$R^B R^c$, —S(O)$_2 R^D$, or —O$R^Y$, wherein $R^Y$ is hydrogen, $C_1$-$C_6$ alkyl, $C_2$-$C_6$ alkenyl, $C_2$-$C_6$ alkynyl, carbocyclyl, heterocyclyl, aryl, heteroaryl, —C(O)$R^A$, —C(O)O$R^A$, —C(O)N$R^B R^c$, or —S(O)$_2 R^D$;

$R^A$ is hydrogen, $C_1$-$C_6$ alkyl, carbocyclyl, heterocyclyl, aryl, or heteroaryl;

each of $R^B$ and $R^c$ is independently hydrogen, $C_1$-$C_6$ alkyl, carbocyclyl, heterocyclyl, aryl, heteroaryl, or taken together with the atom to which they are attached form a ring; and $R^D$ is hydrogen, $C_1$-$C_6$ alkyl, carbocyclyl, heterocyclyl, aryl, or heteroaryl.

2. The compound of claim 1, wherein the compound of Formula (I-c) is a compound of Formula (I-c-i), (I-c-ii), (I-c-iii), or (I-c-iv):

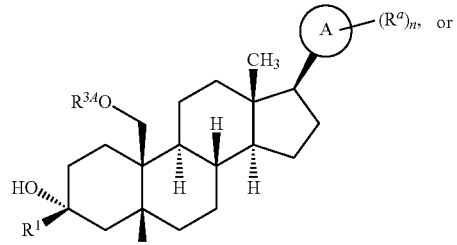
(I-c-i)

(I-c-ii)

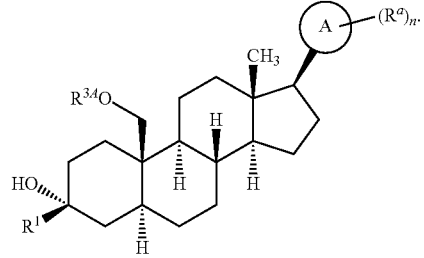
(I-c-iii) or (I-c-iv)

3. The compound of claim 2, wherein the compound of Formula (I-c) is selected from the group consisting of:

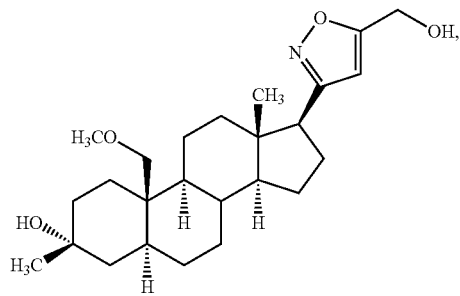

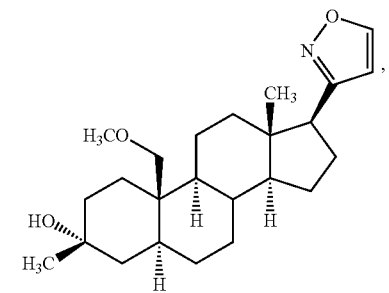

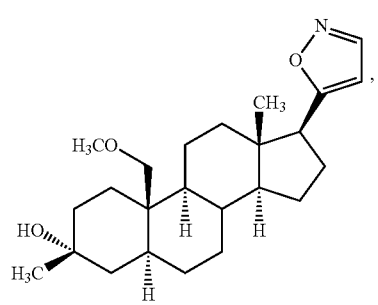

-continued

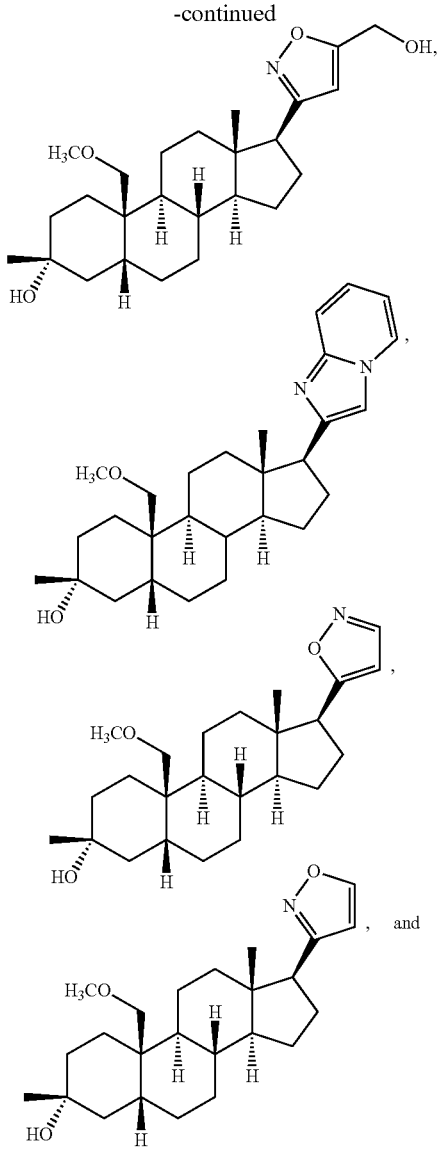

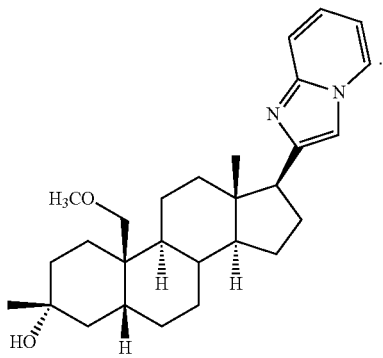

4. A pharmaceutical composition comprising a compound of claim 1 and a pharmaceutically acceptable excipient.

5. A method of inducing sedation and/or anesthesia in a human subject in need thereof, comprising administering to the human subject a therapeutically effective amount of a compound of claim 1, or a pharmaceutically acceptable salt thereof, wherein the human subject experiences sedation and/or anesthesia within two hours of administration.

6. The method of claim 5, wherein the subject experiences sedation and/or anesthesia within one hour of administration.

7. The method of claim 5, wherein the subject experiences sedation and/or anesthesia instantaneously.

8. The method of claim 5, wherein the compound is administered by intravenous administration.

9. The method of claim 5, wherein the compound is administered chronically.

10. The method of claim 5, wherein the compound is administered in combination with another therapeutic agent.

* * * * *